US009539373B2

(12) United States Patent
Jones et al.

(10) Patent No.: US 9,539,373 B2
(45) Date of Patent: Jan. 10, 2017

(54) METHODS, COMPOSITIONS AND APPARATUSES TO TREAT WOUNDS WITH PRESSURES ALTERED FROM ATMOSPHERIC

(75) Inventors: Curtis E. Jones, Savannah, GA (US); John P. Kennedy, Pooler, GA (US)

(73) Assignee: SOUTHEASTERN MEDICAL TECHNOLOGIES, LLC, Savannah, GA (US)

( * ) Notice: Subject to any disclaimer, the term of this patent is extended or adjusted under 35 U.S.C. 154(b) by 2349 days.

(21) Appl. No.: 12/439,120

(22) PCT Filed: Aug. 30, 2007

(86) PCT No.: PCT/US2007/019033
§ 371 (c)(1),
(2), (4) Date: Aug. 12, 2009

(87) PCT Pub. No.: WO2008/027449
PCT Pub. Date: Mar. 6, 2008

(65) Prior Publication Data
US 2010/0016767 A1    Jan. 21, 2010

Related U.S. Application Data

(60) Provisional application No. 60/841,152, filed on Aug. 30, 2006, provisional application No. 60/923,048, (Continued)

(51) Int. Cl.
*A61H 7/00*  (2006.01)
*A61F 13/00*  (2006.01)
(Continued)

(52) U.S. Cl.
CPC ............ *A61M 1/0031* (2013.01); *A61M 1/00* (2013.01); *A61M 1/0088* (2013.01); *A61M 25/00* (2013.01);
(Continued)

(58) Field of Classification Search
CPC ......................... A61M 1/0031; A61M 1/0076; A61M 1/0088; A61M 25/00; A61M 27/00; A61M 27/002; A61M 27/004; A61M 39/00; A61M 39/02; A61M 39/06; A61M 39/0613; A61M 2039/0673; A61F 2002/30677; A61F 2002/3068; A61F 2002/30691; A61F 2002/48; A61F 2002/484; A61F 2002/488
(Continued)

(56) References Cited

U.S. PATENT DOCUMENTS 5,636,643 A    6/1997  Argenta et al.
6,375,977 B1   4/2002  Auguste et al.
(Continued)

FOREIGN PATENT DOCUMENTS

| GB | 2 329 127 | 3/1999 |
| GB | 2 356 148 | 5/2001 |
| WO | WO 03/073970 | 9/2003 |

*Primary Examiner* — Alireza Nia
*Assistant Examiner* — Keri J Nelson
(74) *Attorney, Agent, or Firm* — Nixon & Vanderhye P.C.

(57) ABSTRACT

The invention disclosed comprises methods, apparatuses and compositions to treat acute and chronic wounds with pressures altered from atmospheric. The methods, apparatuses and compositions herein improve the performance of Altered Pressure wound therapy. The improvements also make the treatments more comfortable for the patient and the delivery of the treatment more convenient for clinicians. These improvements collectively result in improved efficacy, improved compliance, improved safety and improved clinical efficiency, while limiting clinical errors in treatment.

15 Claims, 43 Drawing Sheets

Related U.S. Application Data filed on Apr. 12, 2007, provisional application No. 60/931,271, filed on May 22, 2007, provisional application No. 60/958,897, filed on Jul. 10, 2007.

(51) Int. Cl.

| | | |
|---|---|---|
| *A61F 15/00* | (2006.01) | |
| *A61M 31/00* | (2006.01) | |
| *A61M 37/00* | (2006.01) | |
| *A61M 1/00* | (2006.01) | |
| *A61M 5/32* | (2006.01) | |
| *A61M 25/00* | (2006.01) | |
| *A61M 27/00* | (2006.01) | |
| *A61M 39/00* | (2006.01) | |
| *A61M 39/06* | (2006.01) | |
| *A61M 39/02* | (2006.01) | |

(52) U.S. Cl.
CPC .............. *A61M 27/00* (2013.01); *A61F 13/00* (2013.01); *A61M 1/0076* (2013.01); *A61M 39/00* (2013.01); *A61M 39/02* (2013.01); *A61M 39/06* (2013.01); *A61M 39/0613* (2013.01); *A61M 2039/0673* (2013.01)

(58) Field of Classification Search
USPC ... 602/41–43, 51, 53, 54, 57, 58; 604/93.01, 604/128, 129, 174, 176, 180, 268, 304, 604/305, 315–318, 327, 543; 601/6, 9, 11
See application file for complete search history.

(56) References Cited

U.S. PATENT DOCUMENTS

| | | | |
|---|---|---|---|
| 6,856,821 | B2 | 2/2005 | Johnson |
| 7,485,112 | B2 * | 2/2009 | Karpowicz et al. .......... 604/304 |
| 2005/0261642 | A1 | 11/2005 | Weston |
| 2006/0127437 | A1 | 6/2006 | Kennedy et al. |

* cited by examiner

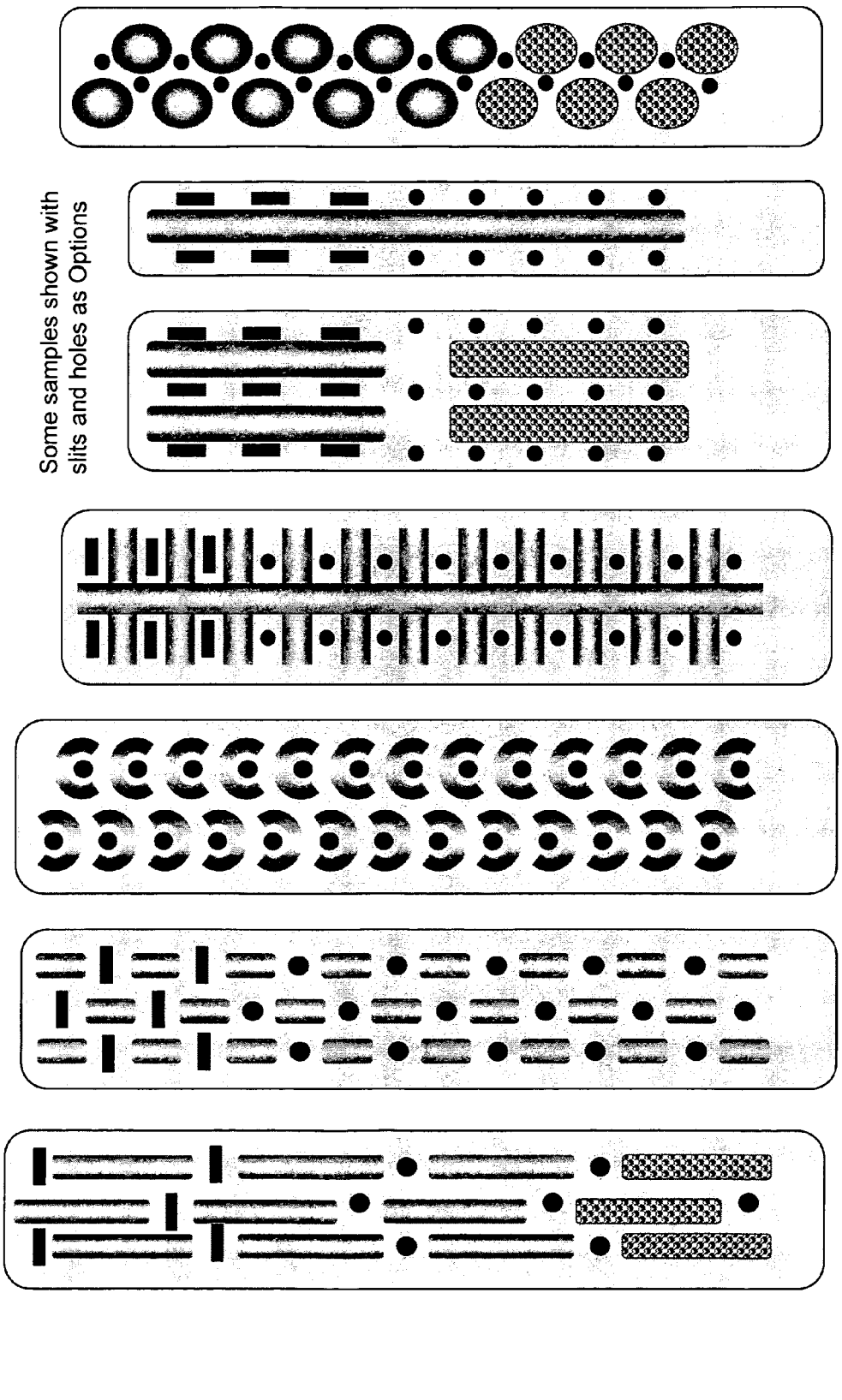

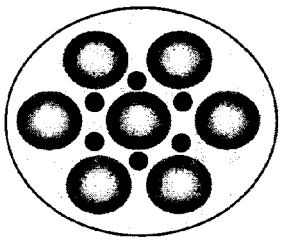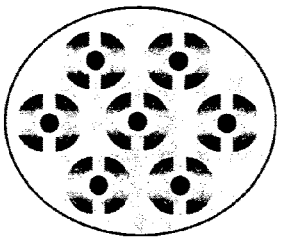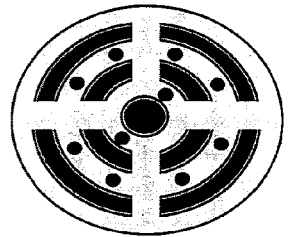

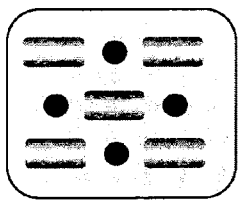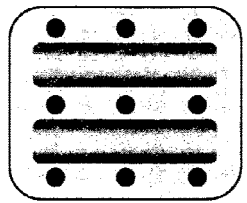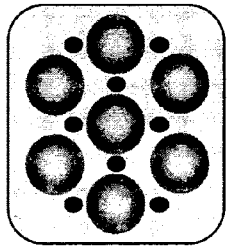

*Irregular or "Non-Planar" Surface Designs Continued*

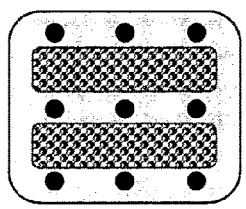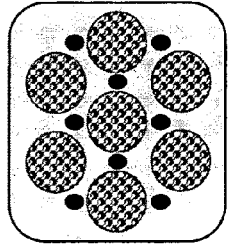

Examples of smaller devices intended for smaller or shorter wounds that have irregular shapes.

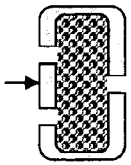

Option: interiors may be filled with porous matrix

Figure 13

Note: designs may be of a single unit or assembled, single or dual sided & side or top ported.

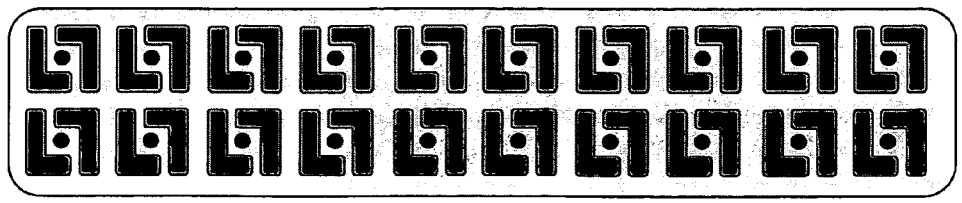

More examples of non-planar designs with passages located adjacent to crests, mounds and/or ridges.

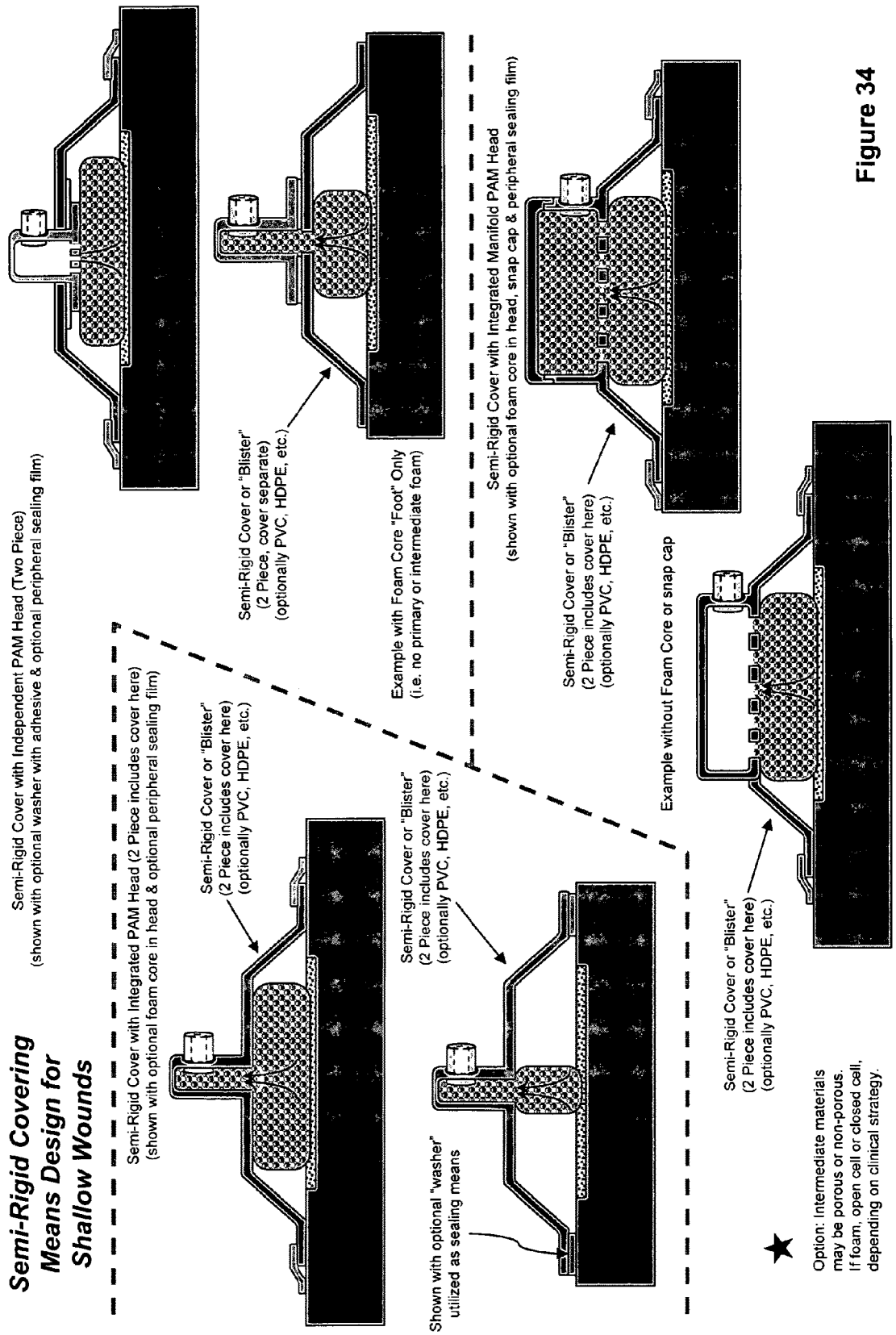

Illustrations of Flexible Cylindrical Foam "Rope"
(Secondary and Intermediate Materials for Wound Packing)

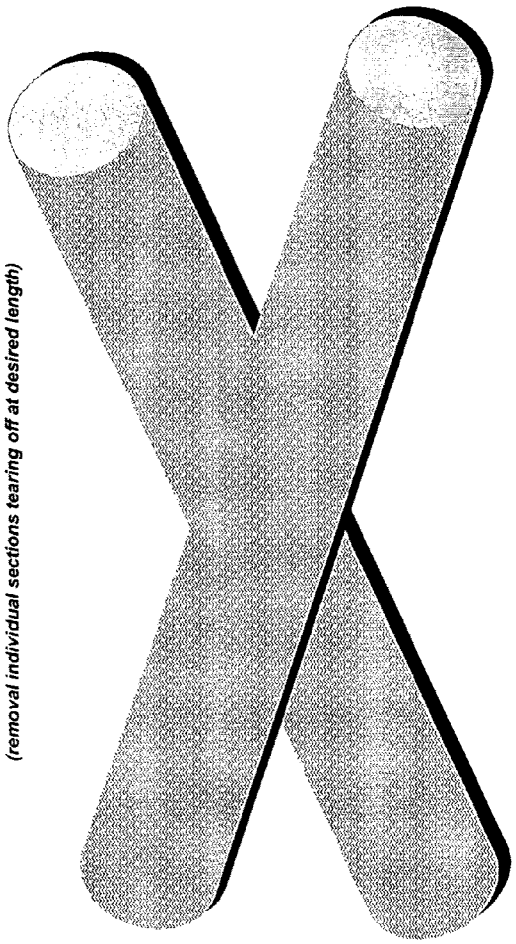

*After*
(removal individual sections tearing off at desired length)

★ Option: Intermediate materials may be porous or non-porous. If foam, open cell or closed cell, depending on clinical strategy.

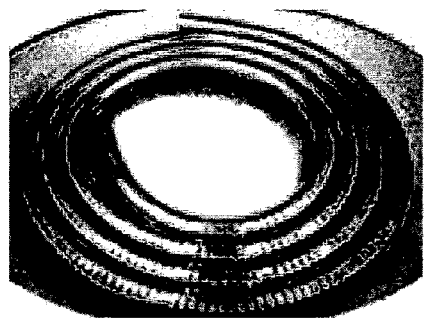

*Before*
(before unwinding or extending)
(examples of packaging configurations)

Figure 35

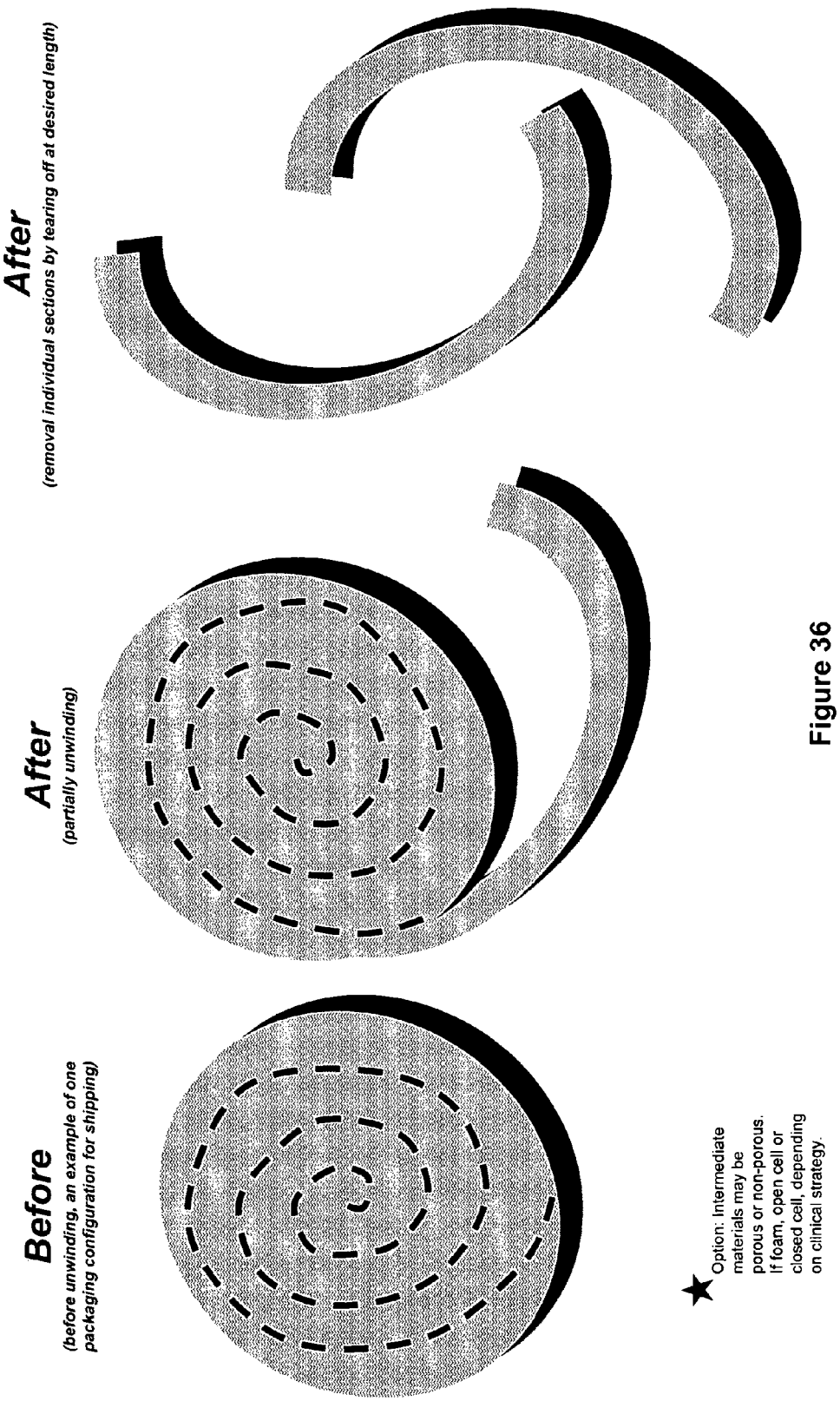

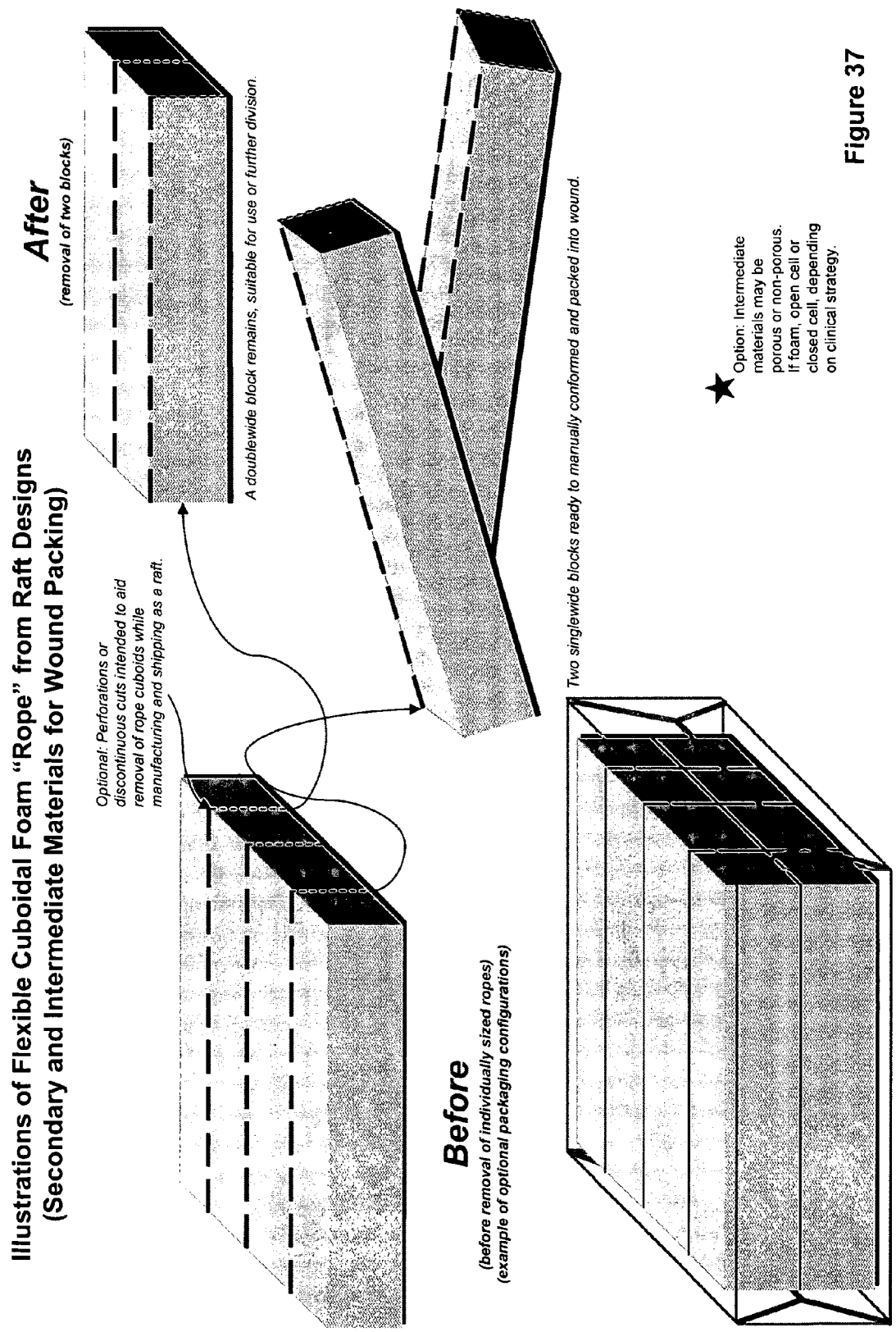

METHODS, COMPOSITIONS AND APPARATUSES TO TREAT WOUNDS WITH PRESSURES ALTERED FROM ATMOSPHERIC

This application is the U.S. national phase of International Application No. PCT/US2007/019033 filed 30 Aug. 2007 which designated the U.S. and claims priority to U.S. Provisional Patent Application Ser. No. 60/841,152 filed Aug. 30, 2006, Ser. No. 60/923,048 filed Apr. 12, 2007, Ser. No. 60/931,271 filed May 22, 2007, and Ser. No. 60/958,897 filed Jul. 10, 2007, the entire contents of each of which are hereby incorporated by reference.

BACKGROUND OF THE INVENTION

Field of the Invention

This invention relates to generally to wound healing. In particular, the invention relates to wound healing with pressures altered both positively and negatively from atmospheric.

More specifically this invention is directed at apparatuses and methods that utilize Altered Pressures which are more convenient, safe and efficient for the clinician, more comfortable and less painful for the patient, and result in improved efficacy versus those of the prior art.

Background of the Invention

The need to rapidly close acute and chronic wounds has been a focus of research since the dawn of medical practice. The background art is characterized by therapeutic strategies utilizing pressures altered from atmospheric conditions. Such strategies have been practiced by clinicians for both acute and chronic wounds for over a hundred years. Positive pressure strategies began expanded utilization least by the early 1800's, while negative pressure wound therapy began institutional practice at least as far back as the early 1980's.

Positive pressure wound therapy began by employing large chambers that encapsulated the entire patient. While more locally focused pressures have been attempted, they proved problematic for the relatively high pressures utilized. Conversely, to date negative pressure wound therapy has been developed as a local site methodology, specific to a peripheral zone around the wound bed. Likewise, the present invention limits its application to the local tissue of and around the wound; however, it utilizes both negative pressures and positive pressures.

The following core features are common among the negative pressure wound therapy configurations known in the art which employ a local site application methodology:
a covering means adapted to protect a wound from contamination and/or trauma;
a sealing means, optionally designed as a part of the covering means, for establishing intimate but reversible contact with the perimeter of said covering to surrounding skin surfaces of said wound, thereby creating an Encapsulated Space, including the wound bed under said covering;
the sealing means further providing a seal competent enough to provide treatment of the wound with pressures purposefully altered to those lower than atmospheric;
a pressure altering means for interfacing negative pressures from a source with the said Encapsulated Space to lower the pressure therein as desired, said pressure altering means working in combination with said covering and sealing means to maintain the so desired Encapsulated Space pressures;
the pressure altering means comprising a Proximal end, a Medial section and a Distal end;
a negative pressure source for delivering the initial pressure differential to the pressure altering means; and
optionally at least one of the following:
a. the pressure altering means further consisting of a Proximal end with direct physical access to the Encapsulated Space through an opening or conduit through said covering, and a Distal end connected to the Proximal end via a Medial section, such Distal end further adapted for connection to a negative pressure source; or
b. the pressure altering means further consisting of a Proximal end with direct physical access to the Encapsulated Space through a passage created between skin and sealing means of said covering, and a Distal end connected to the Proximal end via a Medial section, such Distal end further adapted for connection to a negative pressure source; or
c. the pressure altering means further consisting of a Proximal end with indirect access to the Encapsulated Space though a void or opening in said cover, and a Distal end connected to the Proximal end via a Medial section, such Distal end further adapted for connection to a negative pressure source; or
d. the pressure altering means further consisting of a Proximal end with indirect access to the Encapsulated Space through a passage created between skin and sealing means of said covering, and a Distal end connected to the Proximal end via a Medial section, such Distal end further adapted for connection to a negative pressure source.

The apparatus above generically encompasses the core features of the historical apparatuses in the literature and prior art.

Related Art

A search of the prior art did not disclose any patents that read directly on the claims of the instant invention; however, the following references were considered related.

Journal article "The vacuum effect in the surgical treatment of purulent wounds" by Kostiuchenok, I I; Kolker, V A Karlov V A, et al.: *Vestnik Khirurgii* 1986 describes an intermittent manual application of minimal negative pressure to reduce bacterial counts and heal stubborn wounds.

Journal article "Vacuum therapy of acute suppurative diseases of soft tissues and suppurative wounds" by Davydov IuA, Larichev A B, Smirnov A P: *Vestnik Khirurgii Imeni i—i.—Grekova* 1986 presents the retrospective results of over 100 patients presenting with purulent mastitis. The authors describes the techniques of intermittent application of various negative pressures and durations as used in their clinic since 1980, as well as efficacy results regarding these techniques.

Journal article "Active wound drainage" by Usupov, Y N; Yepifanov, M V: Vestnik Khirugii 1987 describes the authors methodology and results for determining apparent threshold and maximum negative pressures which attempt to project a therapeutic index for negative pressures from an animal model.

Journal article "Bacteriologic and cytologic evaluation of vacuum therapy of suppurative wounds" by Davydov IuA, Larichev A B, Men'kov K G: *Vestnik Khirurgii Imeni—i—Grekova* 1988 describes the techniques for intermittent application of various negative pressures and durations and demonstrates the faster progression through healing stages of these patients compared to controls.

Journal article "Effective management of incisional and cutaneous fistulae with closed suction wound drainage" by Chariker, M E; Jeter, K F, et al.: *Contemporary Surgery* 1989 authors describe specific dressings and treatment methodologies including drains, screens, packings and covers which are readily available to world wide clinicians and readily adaptable to negative pressure therapy. The authors report on the training and efficacy of these methodologies for a specific hard to heal surgical wounds, namely fistulae complicated wounds.

Journal article "Concepts for clinical biological management of the wound process in the treatment of purulent wounds using vacuum therapy" by Davydov, Y A; Larichev, A B, Abramov A Y, et al.: *Vestnik Khirugii* 1991 authors report on expansion of applications of negative pressure techniques to various acute and chronic wounds as well as patient populations as expanded since their previous publication. Authors also describe attributes of negative pressure therapy that may explain its efficacy.

U.S. Pat. No. 4,969,880 issued in the name of Zamierowski; David S. teaches the composition of a wound dressing designed for negative pressure treatment of a wound that includes a semi-permeable cover with an adhesive sealing means, an opening formed through the cover for the introduction of a PAM said PAM adapted for connection to a negative pressure source or a fluid source for introducing fluids and Intermediate Materials placed between the wound and the cover. A method of wound treatment with the teachings of the dressing is also disclosed.

U.S. Pat. No. 5,645,081 issued in the name of Argenta et al. teaches another method for wound treatment utilizing negative pressure, but utilizes an impermeable cover rather than semi-permeable, contrary to U.S. Pat. No. 4,969,880. The patent further teaches the use of Intermediate Materials with impermeable covers with the PAM contained within or underneath the Intermediate Materials.

U.S. Pat. No. 5,636,643 issued in the name of Argenta et al. teaches another method for wound treatment utilizing negative pressure, but utilizes an impermeable cover rather than semi-permeable, contrary to U.S. Pat. No. 4,969,880. The patent further teaches the use of negative pressure adapted to specific wound types and specific durations of therapy.

U.S. Pat. No. 6,135,116 issued in the name of Vogel et al. teaches a method and apparatus for combining intermittent pneumatic compression and negative pressure wound therapy.

U.S. Pat. No. 6,553,998 issued in the name of Heaton et al. teaches negative pressure wound therapy that utilizes the combination of a suction head and a cover. More specifically, the suction head is designed with projections on the bottom flange which prevent sealing or blockage of the suction head by providing flow channels for liquids to exit the wound via a PAM.

Consequently, a need has been demonstrated for the invention which provides methods, apparatuses and compositions that: (a) improve the performance of Altered Pressure wound therapy (b) make the treatments more comfortable for the patient, and (c) make the administration of the treatment more convenient for clinicians. These improvements collectively result in improved efficacy, improved compliance, improved safety and improved clinical efficiency, while limiting clinical errors in treatment.

SUMMARY OF THE INVENTION

The purpose of the invention is to provide apparatuses, or components thereof, devices and methods that improve the performance of Altered Pressure wound therapy, make the treatments more comfortable for the patient and the delivery of the treatment more convenient for the clinician. These combined benefits cascade to provide improved efficacy, improved patient compliance and improved efficiency, while limiting clinical errors in treatment.

A first aspect is an Altered Pressure apparatus and method for delivering Altered Pressure therapy to a wound. The apparatus and method comprises a PAM with at least a two piece Proximal end, further comprising at least a portion of at least one piece located within the Encapsulated Space, at least a portion of at least one piece located outside of the Encapsulated Space, and at least one portion of at least one piece passing through said covering, optionally with adhesive, support washers or heat welds for fixation and support.

In broad terms, a preferred embodiment of the apparatus is comprised of a tube located completely outside the Encapsulated Space, at least one internal piece and one external piece united in a male and female connection, and at least one piece passing through the covering further adapted to aid perforation or insertion through the covering.

One advantage of the invention is that the pieces may be rapidly assembled by the clinician at the time of use. Another advantage of the invention is that, when desired, it provides the clinician with a means to uniformly perforate the covering in a reproducible manner. Another advantage of the invention is that, when desirable, it allows the clinician to assemble at least some of the Proximal end of the PAM with the covering prior to application to the patient. This allows the clinician to assemble at least some of the Proximal end of the PAM with the covering prior to removal of the release liner of the covering, further aiding handling for the clinician. The invention also provides a means to secure the PAM to the covering and within the opening in said covering.

Another aspect is an Altered Pressure apparatus and method for delivering Altered Pressure therapy to a wound. The apparatus and method comprises a PAM with a Proximal end accessing the Encapsulated Space that is at least partially filled with a porous matrix.

In broad terms, in a preferred embodiment the section of the PAM that accesses the Encapsulated Space is at least partially filled with open-cell foam.

One advantage of the invention is that the wicking or capillary action of the porous matrix supplements the apparatus when negative pressures are used. Furthermore, the uptake of fluids under negative pressure is more evenly distributed for the length of the PAM when a porous matrix interior is provided. Likewise, when positive pressures are used, the porous matrix aids the even distribution of the any liquid or gas within the Encapsulated Space. The porous matrix may also serve as a means to limit the collapse of the PAM due to negative pressures.

Another aspect is an Altered Pressure apparatus and method for delivering Altered Pressure therapy to a wound. The apparatus and method comprises a PAM with a Proximal end accessing the Encapsulated Space that is further comprised of a prefabricated tubular ring or coil.

In broad terms, in a preferred embodiment the section of the PAM that accesses the Encapsulated Space is fabricated to maintain its shape without further measures taken by the clinician. Another preferred embodiment locates the perforations in the interior diameter of the ring or between the coils.

One advantage of the invention is that the rings and coils so fabricated will not open to a wider diameter within the Encapsulated Space thereby causing local trauma and pain.

The fabricated rings or coils are also faster for the clinician to apply. Since the fabricated rings and coils have an overall diameter, it is easy to alter the size to match the wound by eliminating some coils or using a smaller ring. Locating the perforations in the interior diameter of the ring or between the coils limits the ability of tissue to directly contact and block the openings as a source of trauma.

Another aspect is an Altered Pressure apparatus and method for delivering Altered Pressure therapy to a wound. The apparatus and method comprises a PAM with a Proximal end accessing the Encapsulated Space that is further comprised of an outer sheath or peripheral flap.

In broad terms, in a preferred embodiment the section of the PAM that accesses the Encapsulated Space is fabricated with an outer sheath or peripheral flap of a biocompatible material such as a silicone derivative. Another preferred embodiment utilizes the sheath or flap design in conjunction with a semisolid as they are particularly adapted to limit clogging by semisolids.

One advantage of the invention is that the sheath or flaps limit the ability of tissue to directly contact and block the openings as a source of trauma. Another advantage is that these designs allow the clinicians to utilize semi-solids within the Encapsulated Space with limited blockage of the openings in the PAM.

Another aspect is an Altered Pressure apparatus and method for delivering Altered Pressure therapy to a wound. The apparatus and method comprises a PAM with a Proximal end accessing the Encapsulated Space and further comprises an Intermediate Material between the tissue and the PAM, thereby reducing tissue trauma and pain created by direct contact between the PAM and tissue.

Another aspect is an Altered Pressure apparatus and method for delivering Altered Pressure therapy to a wound. The apparatus and method comprises a PAM with a Proximal end, located external of the Encapsulated Space, positioned or attached on Top of the covering relating to one or more openings in the covering, an Intermediate Material positioned at least partially between the tissue and covering means including any opening, thereby reducing pain and trauma from direct contact of the wound bed and the covering means or PAM.

Another aspect is an Altered Pressure apparatus and method for delivering Altered Pressure therapy to a wound. The apparatus and method comprises an anti-infective.

In broad terms, in a preferred embodiment the anti-infective is a semisolid. In another preferred embodiment the semisolid is a lipid. In another preferred embodiment the lipid is a fatty acid. In another preferred embodiment the lipid is a fatty acid ester.

One advantage of the invention is anti-infectives augment the ability of Altered Pressure wound therapy to control bacteria and biofilm formation. Semisolids, most preferably Hydrophobic, also provide the advantages of limited trauma upon dressing changes, anti-granulation infiltration, malleable void fillers and prevention of over drying the wound. Advantages of lipids include anti-infective utility, reduced pain upon dressing changes, low cost, low resistance, low sensitization, low toxicity and good biocompatibility.

Another aspect is to provide a device and method for connecting an Altered Pressure source to a PAM. The device and method comprises a means to control pressures in the PAM and controlling the pressures within the PAM from the source.

In broad terms, in a preferred embodiment the pressure source is the in-wall, in-house or another provided utility source for Altered Pressure located in a patients room, suite or location. In another preferred embodiment the means to control pressures comprises a pressure regulation means to maintain the pressure within the PAM to a value different from the source pressure, a shut off means to the pressure source, a relief means to return the PAM pressure to atmospheric, a means of logic control of all functions, a means of programmable logic, a means of determining duration of treatment related to compliance, a means for alarms to assist operator awareness of regimen stage, a means of alarms for malfunction, a means of alarms for maintenance and a means of alarms for leaks. In another preferred embodiment the means to control pressures comprises a tank, reservoir or bladder component in order to prevent significant deviations in pressure from the pressure source.

One advantage of the invention is that the in-house pressure source may be utilized as the driving force for Altered Pressure therapy. Another advantage is more space may be provided in the patience room. Furthermore, the device makes the in-house pressure source adaptable to treatment regimens and programmable treatment protocols. The device also provides for pressure changes caused by use of the in-house system in other locations.

Another aspect is to provide an apparatus and method for negative pressure wound therapy. The device and method comprises a covering means adapted to protect a wound from contamination and/or trauma; a sealing means for establishing intimate but reversible contact with the perimeter of said covering to surrounding skin surfaces of said wound, thereby creating an Encapsulated Space, including the wound bed under said covering; the sealing means further providing a seal competent enough to provide treatment of the wound with pressures purposefully altered from atmospheric, including higher and lower pressures; a pressure altering means for interfacing non-atmospheric pressures with the said Encapsulated Space, said pressure altering means working in combination with said covering and sealing means to maintain the so desired Encapsulated Space pressures; the pressure altering means comprising a Proximal end, a Medial section and a Distal end; the pressure altering means adapted to deliver negative pressures via venturi aspiration from Medial section of PAM, a reservoir means for holding a gas or liquid prior to flow through PAM; a bulk collection means for collection of discharge from PAM; a pump for delivering the initial pressure differential to the pressure altering means; and an order of configuration beginning at the reservoir, through Proximal end of the PAM, through the Medial section of the PAM within Encapsulated Space, through or by the pump and finally through the Distal end of the PAM into the bulk collection means.

In broad terms, in a preferred embodiment the lines providing the venturi aspiration also provide a means to alter wound bed temperature by regulation of the gas or liquid temperature providing the venturi aspiration. In another preferred embodiment the reservoir and collection means are connected by a conduit thereby adapting the reservoir for recirculation. In another preferred embodiment any liquid contained in the reservoir contains an anti-infective agent.

One advantage of the invention is that Altered Pressure therapy can be combined readily with thermal therapies. By recirculation of fluids or gases a quantity may be specified specific to the treatment duration. By incorporation of an anti-infective, the recirculation bio-burden is controlled.

Another aspect is an Altered Pressure apparatus and method for collecting bulk wound products and discharge. The apparatus and method comprises a collection means adapted for emptying the collected products without altering the pressures in the Encapsulated Space and without interrupting continuous collection of wound products into the collection means.

In broad terms, in a preferred embodiment the bulk collection means comprises multiple collection containers located downstream from a split junction and upstream from a union junction, and further comprises multiple valves. In another preferred embodiment a single valves that operates multiple paths is employed. In another preferred embodiment the containers are equipped with a top covering means adapted for penetration by at least a portion of the PAM. In another preferred embodiment the top covering means incorporates a means to attach the container to support structure of the bulk collection means. In another preferred embodiment the collection container or liner contains a means to control bacteria growth and odor.

One advantage of the invention is that the therapy does not need to be halted while the collected products are disposed of. Another advantage is the rapid change of the containers without intimate contact of the clinician's hands with the products. Furthermore, the control of bacteria growth limits the overall institutional burden and helps control unpleasant odors.

Another aspect is an Altered Pressure apparatus and method for allowing minimum pressure change while changing drainage collection or moving a patient. The apparatus and method comprises a shut off means for temporarily sealing the pressure altering means between the Distal and Proximal ends.

In broad terms, in a preferred embodiment the shut off means is comprised of a pressure closure, valve closure or self-sealing pierced membrane. In another preferred embodiment a means of disconnection of between the shut off means and the Altered Pressure source is also provided.

Another aspect is an Altered Pressure apparatus and method for increasing patient comfort and limiting tissue trauma. The apparatus and method comprises a cushioning means between the pressure altering means and the skin, specifically the peripheral skin surrounding the wound.

In broad terms, in a preferred embodiment the cushioning means is located within 1 cm to 10 cm (e.g., about 7.5 cm) from the beginning margin of the wound.

Another aspect is an Altered Pressure apparatus and method for supporting and reinforcing the opening in a covering. The apparatus and method comprises a reinforcing support washer for fixation to the periphery of the opening.

In broad terms, in a preferred embodiment the washer is adapted to be non-rigid. In another preferred embodiment the washer is composed of multiple layers to assist manufacturing. In another preferred embodiment the washer is composed of multiple layers held in place by adhesive. In another preferred embodiment the washer is composed of adhesive on at least the side opposite the covering. In another preferred embodiment the washer further providing a means for rapid adherence and fixation of a PAM to the Top of the cover directly over an opening through said cover. In another preferred embodiment the washer is adapted to accommodate a one or more release liners to aid handling, production and application.

One advantage of the invention is that the washer can provide a pressure fit, around the PAM to augment the seal. Another advantage is that the washer aids the prefabrication of covering for use with PAM designed to be inserted through the covering. Another advantage is that the washer provides the clinician the option of attaching the PAM after the cover has been applied to the patient when desirable.

Another aspect is an Altered Pressure apparatus and method for treating wounds. The apparatus and method comprises altering the pressure in the Encapsulated Space from atmospheric by a specified amount for a specified duration, thereby creating a single cycle of therapy.

In broad terms, in a preferred embodiment the pressure is between 1 and 140 mm Hg greater than atmospheric. In another preferred embodiment the pressure is between 1 and 140 mm Hg less than atmospheric.

One advantage of the invention is that the benefits of positive and negative pressure wound therapy may be used in cycles.

Another aspect is an Altered Pressure apparatus and method for treating wounds. The apparatus and method comprises the utilization of an anti-granulation in-growth adhesion material.

In broad terms, in a preferred embodiment the anti-granulation material is an irritant. In another preferred embodiment the anti-granulation material is a lipid.

One advantage of the invention is that the anti-granulation material will limit in-growth within dressings and therefore greatly reducing trauma and pain upon dressing change.

Another aspect is an Altered Pressure apparatus and method for treating wounds. The apparatus and method comprises the utilization of a rigid covering means for shallow wounds.

In broad terms, a preferred embodiment employs a semi rigid covering means that will resist collapse under negative pressure. Another preferred embodiment requires the addition of a headspace manifold in the crown of the blister.

One advantage of the invention is that the semi-rigid blister allows the use of Altered Pressure therapy over a shallow wound. Another advantage is that an Intermediate Material may still be used with the invention even though the wound is shallow. Another advantage is that the headspace manifold provides for the distribution of pressures and alternate paths when partial restrictions develop.

Another aspect is an Altered Pressure apparatus and method for treating wounds. The apparatus and method comprises the utilization of Intermediate Materials.

In broad terms, in preferred embodiments configurations utilizing porous Intermediates for wounds are described when desirable. In other preferred embodiments non-porous Intermediates for wounds are described when desirable, including the conversion of porous to non-porous by Hydrophobic semi-solids.

One advantage of the invention is that porous materials provide a capillary drive to aid collection by the PAM when using negative pressures. A second advantage is that non-porous materials direct the flow of fluids in limited volumes of space, thereby greatly increasing the velocity of the fluids at the tissue interface. A third advantage unique to non-porous material created by, or used with, Hydrophobic semisolids is the anti-adhesive and cushioning attributes which greatly reducing trauma and pain for patients.

Another aspect is an Altered Pressure apparatus and method for delivering Altered Pressure therapy to a wound that includes the use of biocompatible proteinaceous foams. The apparatus and method comprises a proteinaceous foam as a primary, secondary or Intermediate Material within the Encapsulated Space.

In broad terms, in a preferred embodiment the proteinaceous foam within the Encapsulated Space is manufactured from biocompatible proteins such as collagen, gelatin, lactoferrin or derivatives.

One advantage of the invention is that these foams are biodegradable and less of a risk if mistakenly left in the wound. Furthermore, many of these proteins stimulate tissue growth. Another advantage is that some of these foams may be manufactured into compositions that retard bacteria growth. In an open cell configuration the foams provide superior wicking. In a closed cell, or even a fenestrated closed cell configuration, the foams provide superior exudate velocity and turnover at the tissue surface.

Another aspect is an Altered Pressure apparatus and method for delivering Altered Pressure therapy to a wound that includes the use of foam dressings in the form of Rope coils and Rafts.

In broad terms, in a preferred embodiment the foam is processed into a foam Rope that can be readily cut or tom to provide the pRoper quantity for a specific wound.

One advantage of the invention is that the Rope is readily adapted to the shape most any wound without the need for custom fitting, making dressing changes more efficient. Furthermore, the Rope may be packaged in coils, windings or Rafts to aid packaging, shipping and dispensing.

Another aspect is a side by side (or dual Lumen) tubing or conduit that readily may be adapted to provide a feedback loop for pressure sensing and control.

In broad terms, in a preferred embodiment each passage remains independent for at least a portion of the PAM. Further, one passage is dedicated to the feedback loop while the other delivers the pressure differential to the Proximal end of the PAM.

One advantage of the invention is that side by side or dual Lumen configurations can be made relatively flat and flexible, both attributes that improve patent comfort. Furthermore, the flow requirement may be customize by sizing the passages independently.

Another aspect is an Altered Pressure apparatus and method for delivering Altered Pressure therapy to a wound. The apparatus and method comprises transport configurations which provide support, security, convenience and safety to patients.

In broad terms, in a preferred embodiment the system makes Altered Pressure wound therapy devices and components readily Portable in an organized and secure manner. In another preferred embodiment the invention provides a Cradle configuration, as defined herein, that can be readily separated from the pressure source and collection means of the systems. In another preferred embodiment the system provides a docking base removably fixable to a stable object including a bed. One advantage of the invention is the Cradle provides for the organization of the pressure source and collection means, including ancillary components, but the primary function of the Cradle is to secure the pressure source and collection means to prevent them from upset. Another advantage is the Cradle allows a Mobile pressure source to be transported and utilized with the collection means without fear of constant upset. Therefore, the Cradle provides the means to satisfy the needs of both the Portable and Mobile market segments with one pump allowing patients to train on only one device in the presence of professionals which improves compliance. Another advantage is the Cradle Bay provides a means to at least partially hide the wound exudate from public view. Even partially hiding the wound exudate provides a valuable function beyond elegance, as often laymen will faint at the sight of bodily fluids risking injury. Another advantage is the docking station is intended to merge with a Cradle configured system, rendering even greater stability to the same, while keeping the system out of the direct work area of the clinicians which is critical in medical emergencies.

In broad terms, in another preferred embodiment the system makes Altered Pressure wound therapy devices and components readily Mobile in an organized and secure manner. In another preferred embodiment the accessory provides for the organization of the pressure source and collection means, including ancillary components, but the primary function of the accessory is to allow transport by the patient without the use of any hand to secure the system.

One advantage of the invention is that many patients who are candidates for Altered Pressure therapy are elderly, often requiring aids and prosthetics to be able to walk independently. Therefore, the ability to transport the system without securing by hands provides the patent superior balance, security and safety beyond convenience. Another advantage is at least partially hiding the wound exudate from public view, the significance of which was clarified previously.

Embodiments of the invention also provide that any of the disclosed apparatus components, semi-solids or Intermediate Materials may further comprise a Therapeutic, including the following: a hemostasis or coagulation promoting agent; a vasoactive agent; a tissue growth stimulant or a healing promoter; an anti-infective agent; an anti-adhesive agent; a viscosity enhancer; an anesthetic; a solvent or co-solvent; an anti-inflammatory agent; a controlled-release component or composition; or any combination thereof.

In particular embodiments of a semisolid formulation, the Augmentative or Therapeutic agent or combinations thereof may be any of a hemostasis or coagulation promoting agent including a nitric oxide or a nitric oxide generating agent, a catecholamine such as epinephrine, a phospholipid, gelatin, collagen, chitosan, glucosamines such as n-acetylglucosamine, a blood product (such as platelets, prothrombin, thrombin, fibrin, fibrinogen, thromboplastin or a clotting factor), whole blood, blood plasma; a vasoactive agent including a nitric oxide or nitric oxide generating agent, a vasoconstrictor, a cholinomimetic agent, an anticholinergic agent, a cholinergic blocker, a sympathomimetic, an antiadrenergic agent, an adrenergic blocker; a tissue growth stimulant or a healing promoter including angiogenin, angiopoietin-1, a diacylglycerol, del-1, follistatin, an interleukin, a leptin, midkine, pleiotrophin, progranulin, proliferin, a transforming growth factor, a granulocyte colony-stimulating factor, a hepatocyte growth factor, a scatter factor, an epidermal growth factor, a nerve growth factor, a fibroblast growth factor, a keratinocyte growth factor, a placental growth factor, an endothelial cell growth factor, a platelet-derived growth factor, a tumor necrosis factor, vascular endothelial growth factor (VEGF), a vascular permeability factor, insulin-like growth factor, hydroxyapatite, demineralized bone, natural bone, a bone product, a bone morphogenetic protein, a chondrocyte, a calcium phosphate derivative, pepsin, papain, urea; an anti-infective agent including an antibiotic, an antifungal, an antiviral, nitric oxide, a nitric oxide generating agent, tea tree oil, peroxide, a fatty acid, a fatty acid ester; an anti-adhesive agent including a natural polymer, a synthetic polymer, a cellulosic polymer, a carboxymethylcellulose, a polyethylene glycol or a PEG derivative, a polyethylene oxide or PEO derivative, a fatty acid, a fatty acid ester, glycerin; a viscosity enhancer a hydrophilic ointment base, an oleaginous ointment base, an absorbent ointment base, an emulsion ointment base; an anesthetic including clove oil, eugenol, tea tree oil, benzocaine, lidocaine, dibucaine, pramoxine, dyclonine; a solvent or co-solvent; including dodecane, peroxide, phospholipids, a fatty acid, polyethylene glycol, a PEG derivative, polyethylene oxide, a PEO derivative, a biological fluid; an anti-oxidant including hydrophilic and lipophilic antioxidants; an anti-scarring or anti-inflammatory agent including a steroid, a non-steroidal anti-inflammatory drug; a controlled-release component or composition including a multiparticulate, a multiparticulate containing a Therapeutic, a poly(lactic-co-glycolide) (PLGA) multiparticulate, a polyanhydride multiparticulate, a proteinaceous multiparticulate; or any combination thereof.

Further aspects will become apparent from consideration of the drawings and the ensuing description of preferred embodiments of the invention. A person skilled in the art will realize that other embodiments of the invention are possible and that the details of the invention can be modified in a number of respects, all without departing from the inventive concept. Thus, the following drawings and description are to be regarded as illustrative in nature and not restrictive.

BRIEF DESCRIPTION OF THE DRAWINGS

The features of the invention will be better understood by reference to the accompanying drawings which illustrate presently preferred embodiments of the invention.

FIGS. 11 to 13 show cross-sectional and Top down views of various non-planar surface designs. The drawings further show design options including a porous matrix interior.

FIG. 34 depicts various rigid covering means designs especially adaptable to shallow wounds. The drawings further show design options including porous matrix interiors, washers for support or fixation and peripheral sealing adhesive films.

FIGS. 35-37 show foam Rope designs in a variety of packaging, shipping and dispensing configurations including coils and Rafts.

DESCRIPTION OF SPECIFIC EMBODIMENTS OF THE INVENTION

Figure 1:
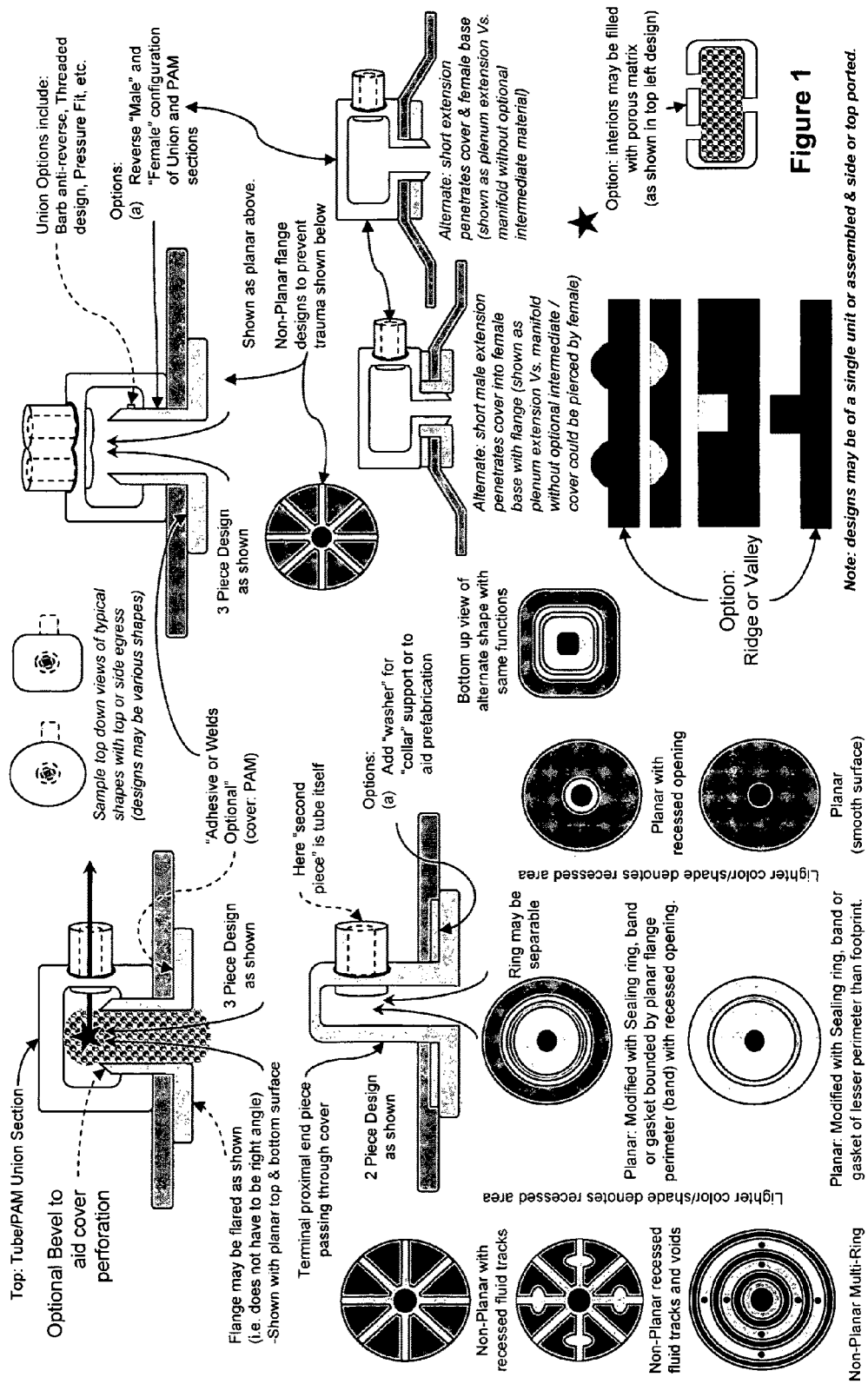
FIG. 1 shows a cross-sectional view of various minimum two piece Proximal end PAM designs. The configurations in the figure depict both two and three piece designs of internal flanges with open Plenums. The drawings further show samples of Top down views of typical shapes and design options including a porous matrix interior, non-planar flanges, washers for support or fixation, male/female connections and beveled elements to aid cover penetration.
Figure 2:
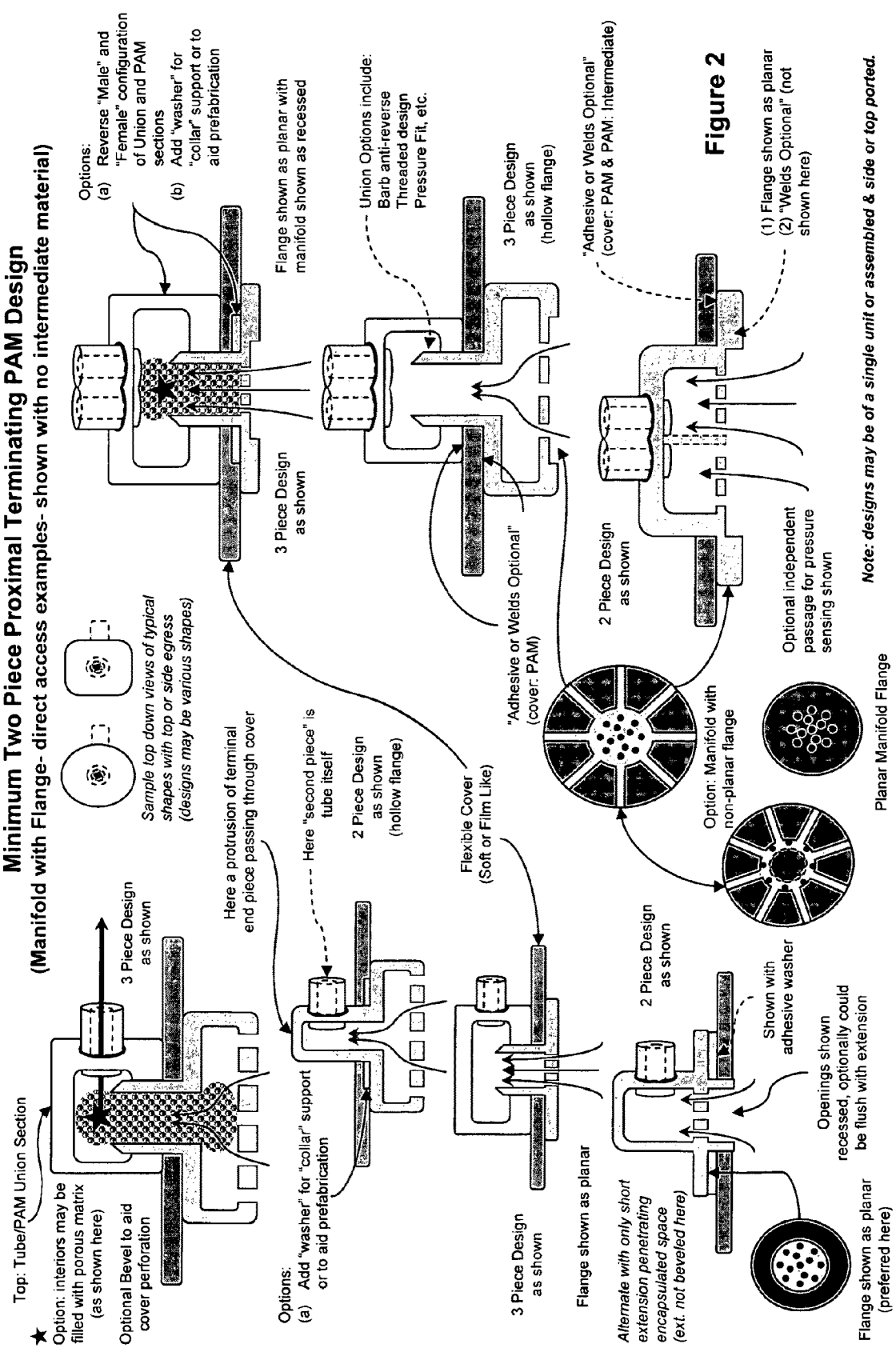
FIG. 2 shows a cross-sectional view of various minimum two piece Proximal end designs. The configurations in the figure depict both two and three piece designs of internal flanges with manifolds to distribute Altered Pressures. The drawings further show samples of Top down views of typical shapes and design options including examples of various opening patterns, porous matrix interiors, non-planar flanges, washers for support or fixation, male/female connections and beveled elements to aid cover penetration.
Figure 3:
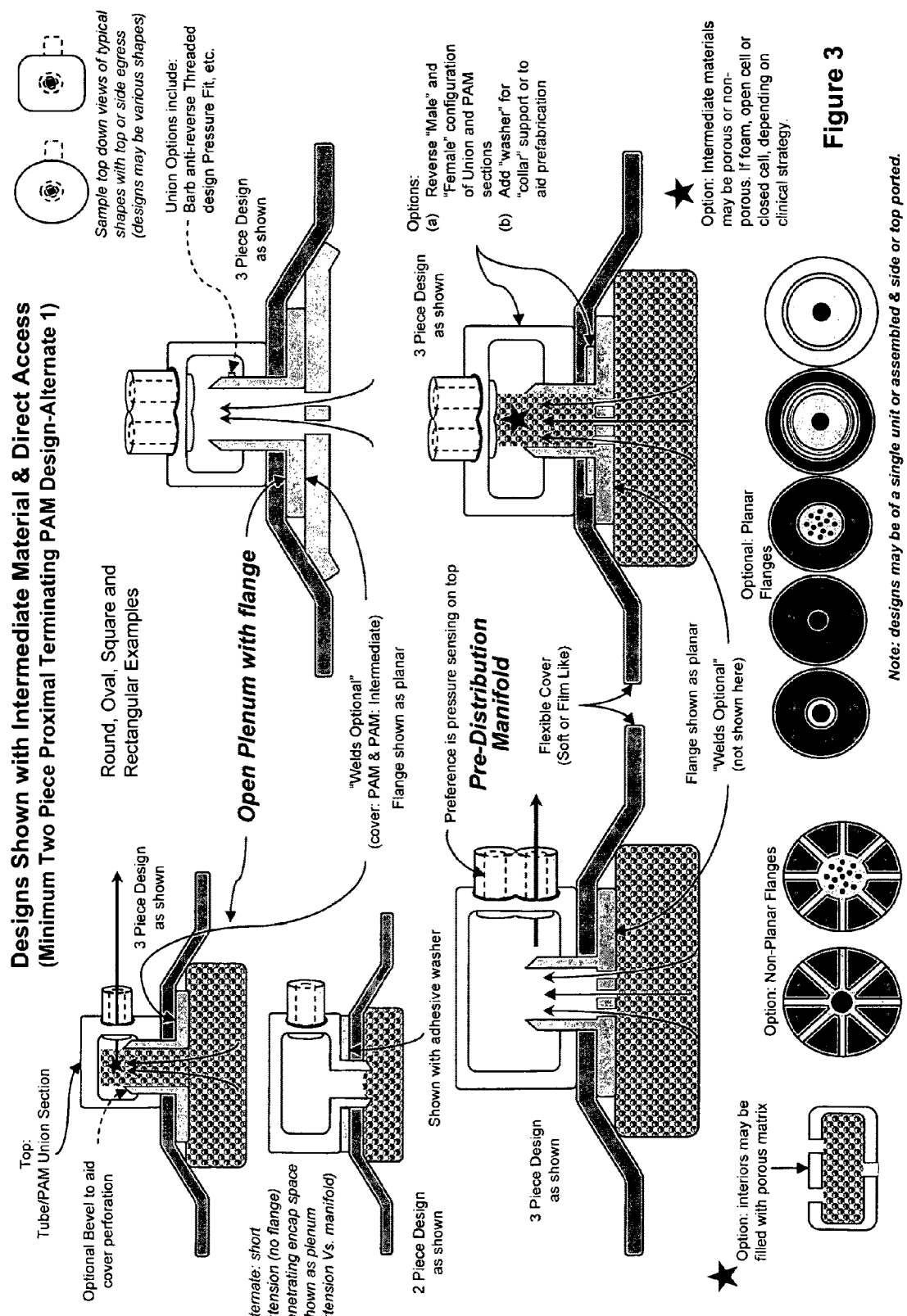
FIG. 3 shows a cross-sectional view of various minimum two piece Proximal end designs. The configurations in the figure depict three piece designs of internal flanges with manifolds or open Plenums which utilize male/female unions. The example configurations also employ an optional Intermediate Material. The drawings further show samples of Top down views of typical shapes and design options including examples of various opening patterns, porous matrix interiors, non-planar flanges, washers for support or fixation, male/female connections and beveled elements to aid cover penetration.

Definitions:

As used in this description and the accompanying claims, the following terms shall have the meanings indicated, unless the context otherwise requires:

"Liquid Crystal" as broadly defined and used herein, means any substance that exhibits a phase of matter that has pRoperties between those of a conventional liquid, and those of a solid crystal. By example, a Liquid Crystal may flow like a liquid, but have the molecules in the liquid arranged and oriented in a crystal-like way. The phases can be distinguished and verified by optical pRoperties and other methods. Examples of Liquid Crystal forming substances include amphiphilic molecules.

"Therapeutic" when used herein means having or exhibiting the ability to heal, treat or provide other benefits, including a substance or composition having or exhibiting the ability to heal, treat or generally provide a benefit. As used herein, Therapeutic agents encompass Augmentative agents, having or exhibiting the ability to enhance or provide a desired physical attribute or attributes of a system thereby impacting the performance of the system for the intended use. Examples of Augmentative agents are viscosity enhancers and swelling agents. "Therapeutic" when used herein as an adjective, means broadly having or exhibiting the ability to heal, treat or provide other benefits. Therapeutic when used herein as an adjective includes Augmentative. When used as a noun herein, Therapeutic or Therapeutic agent, shall mean a substance or composition having or exhibiting the ability to heal, treat or provide other benefits. When used herein as a noun, a Therapeutic or Therapeutic agent shall include an Augmentative agent. Examples of Therapeutics are astringents and irritants.

"Augmentative" when used herein as an adjective, means broadly having or exhibiting the ability to enhance or provide a desired physical attribute or attributes of a system which impacts the performance of the system for the intended use. Therefore, an "Augmentative agent" when used herein means a substance or composition having or exhibiting the ability enhance or provide at least one desired physical attribute which impact the performance of the composition for the intended use. Examples of Augmentative agents are viscosity enhancers and absorbing agents.

"Hemostatic" when used herein as an adjective, means broadly having or exhibiting the ability to significantly limit or arrest the flow of blood under the conditions referenced or apparent when the word is used. When used as a noun herein, or as the noun derivative "hemostat", the nouns mean any substance or composition having or exhibiting the ability to significantly limit or arrest the flow of blood. The noun derivative "hemostasis" as used herein, means having blood flow in the state of significantly limited flow or arrest. The definitions herein are intended as broad descriptors and are not limited to any specific mechanism of blood coagulation or other means of blood flow limitation or arrest.

"Plenum" when used herein, generally means any space or chamber, including partially open chambers, for moving gas, liquids, biological products and/or Therapeutics by a means of a pressure differential. One or more ducts or openings may be connected to a Plenum to provide a means for transportation in and/or out of said Plenum.

"Primary Material" when used herein shall mean any foreign material, any collection of foreign materials, or any composition of foreign materials inserted or incorporated into an Encapsulated Space of a wound bed that separates and prevents the direct contact of other foreign objects with the wound bed. Examples include a primary dressing separating the tissue bed from a specified foreign object.

"Secondary Material" when used herein shall mean any foreign material, collection of foreign materials or any composition of foreign materials inserted or incorporated into an Encapsulated Space of a wound bed that contacts at least a portion of an Intermediate Material. Examples include extra wound packing materials to eliminate adjoining dead space.

"Intermediate Material" when used herein shall mean any material inserted or incorporated into an Encapsulated Space of a wound bed that separates and prevents the direct contact of foreign objects with the wound bed or other foreign objects. Examples include: Primary Materials separating foreign objects from the tissue bed, any foreign materials separating two other objects, any collection of foreign materials separating objects and any composition of foreign materials separating objects.

"Encapsulated Space" when used herein shall mean the space bounded by the covering, sealing means and tissues with a perimeter of the sealing means. For the purposes herein, an imaginary line may be drawn on any breach of the space, in alignment with the midline of the covering or threshold of the peripheral sealing means, to generally indicate the descriptive boundary for the Encapsulated Space.

"Encapsulated Sub-Space" when used herein shall mean any space or compartment at least partially enclosed and adapted to maintain Altered Pressures, other than an Encapsulated Space, bounded by a secondary covering and sealing means with a perimeter of the secondary sealing means. For the purposes herein, an imaginary line may be drawn on any breach of the space, in alignment with the midline of the walls or threshold creating the space, to generally indicate the descriptive boundary for the Encapsulated Sub-Space.

"Top" when used herein in reference to orientation around a wound shall mean the side or position farthest from the patient's wound bed. For clarification a "Top" side would not contact the wound bed.

"Bottom" when used herein in reference to orientation around a wound shall mean the side or position closest to the patient's wound bed. For clarification a "Bottom" side could contact the wound bed provided an Intermediate Material (or primary) is not present.

When referring to a PAM, "Proximal" as used herein with the exception of Venturi designs, shall generally mean within ten inches of the end positioned at the wound, but short of any bulk collecting means. Venturi designs are configured typically with the collection means at the Proximal-Medial portion, but can be a continuous loop.

When referring to a PAM, "Distal" as used herein with the exception of Venturi designs, shall generally mean within ten inches of the end positioned at Altered Pressure source, but not including such source. Venturi designs are configured typically with the Altered Pressure source at the Medial-Distal portion, but can be a continuous loop.

When referring to a PAM, "Medial" as used herein with the exception of Venturi designs, shall generally mean the section of the PAM between the Proximal and Distal ends. Venturi designs are configured typically with the wound/Encapsulated Space at the Medial section, but can be a continuous loop.

"Altered Pressure" when used herein shall mean any pressure differing atmospheric pressure at the geographical location of patient either positively or negatively.

"PAM" when used herein shall be an abbreviation for "pressure altering means" as referenced as a component of the Altered Pressure Apparatus in these definitions.

"Lumen" when used herein shall mean an enclosed channel or passages. As used herein, Lumen is expressly not limited to tubular structures as the term is most commonly used in anatomical text, but also includes inanimate structures of non-tubular shapes. Both Lumens and lumina are acceptable plural versions.

"Rope" when used herein shall be used in the context of a wound dressing or wound packing material. Rope shall mean a slender and flexible shape of material, typically cubical or cylindrical, that may be turned on itself into a "U", serpentine or "coil" shape. As used herein, Rope is a material significantly longer in one dimension, unless broken into sections, making it adaptable to coil upon itself for packaging as well as for filling dead space in a wound of various shapes and sizes.

"Raft" when used herein shall be used in the context of a wound dressing or wound packing material. Raft shall mean segments of Rope located in a row, optionally with layers of rows, and at least partially held in place by lateral unions, surrounding packaging or both.

"Hydrophobic" when used herein shall mean any substance or composition lacking an affinity for water. For the purpose of this filing, any substance or component of a composition with an aqueous solubility less than 1 g solute per 1000 g of solvent, shall be considered Hydrophobic. For the purpose of this filing, any lipophilic or hydrocarbon rich substance or composition shall also be considered Hydrophobic.

"Portable" when used herein shall mean capable of being manually transported readily and comfortably by the average person for more than 50 meters.

"Mobile" when used herein shall mean capable of being transported by the average person as, or as a part of, an accessory worn on one's person unsupported by the hands. By way of example, small cellular phones that may be worn on the belt or carried easily in a clothing pocket are deemed to be Mobile. As defined herein, a typical lady's hand bag worn over the shoulder would qualify as a "Portable" accessory but not "Mobile" as it would be regularly supported by one or two hands during transportation. When used herein, no self contained pressure source shall be deemed "Mobile" if it's theoretical volume exceeds 1 liter or a mass of 2 kg. As used herein, as a minimum, the attribute of "hands free" transport capability must be preserved, excluding putting the accessory on and taking it off.

"Cradle" when used herein shall mean a base or foundation adapted to secure and transport devices that are removable from the Cradle. For clarity, said devices must be readily removable, without the requirement of Cradle disassembly, excluding any simple manual support or holding means. By way of example, though smaller scale, Mobile phones very often are supplied with cradles that are plugged into the wall outlet for battery charging. Any Cradle may be designed with a handle or handles to aid its transport with or without the removable devices in their respective bays. As used herein, the function to secure and transport, as a minimum, both the self contained pressure source and the collection means must be preserved. Potentially synonymous descriptors are caddies, crates and shuttles.

"Bay" when used herein shall mean a receptacle or well set off for the specific purpose of securing a removable device such as the pressure source or collection means.

"Altered Pressure Apparatus" when used herein shall mean an apparatus for treating wounds with the following features in combination:
- a covering means adapted to protect a wound from contamination and/or trauma;
- a sealing means, optionally designed as a part of the covering means, for establishing intimate but reversible contact with the perimeter of said covering to surrounding surfaces of said wound including skin, thereby creating an Encapsulated Space including the wound bed under the covering;
- the sealing means further providing a seal competent enough to provide treatment of the wound with pressures purposefully altered from atmospheric;
- a pressure altering means for communicating Altered Pressures from a source with the said Encapsulated Space to alter the pressure therein as desired, said pressure altering means working in combination with said covering and sealing means to maintain the so desired Encapsulated Space pressures;
- the pressure altering means comprising a Proximal end, a Medial section and a Distal end;
- an Altered Pressure source for delivering the initial pressure differential to the pressure altering means; and optionally at least one of the following:
  i. the pressure altering means further consisting of a Proximal end with direct physical access to the Encapsulated Space through an opening or conduit through said covering, and a Distal end connected to the Proximal end via a Medial section, the Distal end further adapted for direct or indirect connection to an Altered Pressure source; or
  ii. the pressure altering means further consisting of a Proximal end with direct physical access to the Encapsulated Space through a passage created between skin and sealing means of said covering, and a Distal end connected to the Proximal end via a Medial section, such Distal end further adapted for direct or indirect connection to an Altered Pressure source; or
  iii. the pressure altering means further consisting of a Proximal end with indirect access to the Encapsulated Space though a void or opening in said cover, and a Distal end connected to the Proximal end via a Medial section, such Distal end further adapted for direct or indirect connection to an Altered Pressure source; or
  iv. the pressure altering means further consisting of a Proximal end with indirect access to the Encapsulated Space through a passage created between skin and sealing means of said covering, and a Distal end connected to the Proximal end via a Medial section, such Distal end further adapted for direct or indirect connection to an Altered Pressure source.

The present invention includes apparatuses, devices and methods for the treatment of acute and chronic wounds. This invention is particularly useful for treatment of acute and chronic wound that require rapid closure to limit the potential for negative clinical progressions such as continued debilitation, pain and the development clinical or worsening of infection. The materials utilized for the covering means may be classified as impermeable, semi-permeable, permeable, non-occlusive, occlusive, partially occlusive or combinations thereof provided there permeability does not jeopardize the ability to alter pressures of the Encapsulated Space.

I. Multi-Piece PAM Design

In accordance with the present invention, and referring to FIGS. 1-4, 20-24 and 34 preferred embodiments are disclosed. Broadly a PAM is provided to increase patient comfort and clinician administration convenience. The PAM is composed of at least a two piece Proximal end, further comprising at least a portion of at least one piece located within the Encapsulated Space, at least a portion of at least one piece located outside of the Encapsulated Space, and at least one portion of at least one piece passing through said covering, optionally with adhesive, support washers or heat welds for fixation and support.

A best mode of the invention employs a two piece configuration, the second piece of a tubular means located totally outside the Encapsulated Space, optionally configured with a supporting washer, porous matrix interior and non-planar flange.

One method of the invention may be operated by removing any central releasing means, passing one piece through the covering and corresponding washer. Next, insert the porous matrix into the piece, remove any remaining release liner and apply all remaining to the patient. Finally the tubular means maybe connected, thereby adjoining a Medial section of the PAM.

A second best mode of the invention employs a three piece configuration, the second and third piece (a tubular means) located totally outside the Encapsulated Space, first or second piece further configured with a beveled edge to aid insertion or perforation through covering into a male/female union which is reversible pressure fit and optionally where either the male or female piece is significantly softer than the other to aid sealing of the union.

A second method of the invention may be operated by using applying one piece to the covering and subsequently applying to patient, then connecting the pieces through a male/female union into one piece with portions located on both sides of the covering. Finally the tubular means maybe connected thereby connecting all three pieces of the PAM.

The embodiments are further described by the following aspects:

1. An Altered Pressure Apparatus where the terminating PAM is comprised of at least a two piece Proximal end, further comprising: (a) at least a portion of at least one piece located within the Encapsulated Space, (b) at least a portion of at least one piece located outside of the Encapsulated Space, and (c) at least one portion of at least one piece passing through said covering, optionally with adhesive, support washers or heat welds for fixation and support.
2. The PAM of item 1 where at least one piece located at least partially within the Encapsulated Space is not tubing.
3. The PAM of item 1 where at least one piece located at least partially outside the Encapsulated Space is tubing.
4. The PAM of item 3 where the tubing is completely outside the Encapsulated Space.
5. The PAM of item 1 where the connection of pieces forms one passage into the Encapsulated Space through the PAM.
6. The PAM of item 1 where the connection of pieces forms multiple, independent or merged passages communicating with the Encapsulated Space through the PAM.

7. The PAM of item 6 where at least one passage functions as an independent feedback loop for monitoring the pressure at the Proximal end or directly in the Encapsulated Space, thereby providing input for a controlling means to regulate the pressure source to a specified pressure.
8. The PAM of item 7 where the pressure is determined by a pressure sensing means located at the Proximal or Medial end of the PAM; where the pressure value is transferred by a transmitter of electromagnetic radiation, including radio waves, to a receiver communicating with the controlling means.
9. The PAM of item 7 further comprising at least one part that is flexible tubing or flexible conduit, with multiple Lumens, providing or connecting independent passages directly or indirectly to the Encapsulated Space, thereby maintaining the independence of the passages for at least a portion of the PAM.
10. The PAM of item 9 where the tubing or conduit is comprised of two Lumen or dual Lumen: (a) one Lumen reserved for delivering the Altered Pressure directly or indirectly from the Altered Pressure source to the Encapsulated Space, and (b) the other Lumen for providing the feedback loop to control the pressure.
11. The PAM of item 9 where the PAM comprises at least one part that is flexible coax, providing or connecting independent passages to the Encapsulated Space, thereby maintaining the independence of the passages for at least a portion of the PAM.
12. The PAM of item 11 where one channel of the coax reserved for delivering the Altered Pressure directly or indirectly from the Altered Pressure source to the Encapsulated Space, and the other channel of the coax for providing the feedback loop to control the pressure.
13. The PAM of item 6 where the surface containing the multiple openings serves as a manifold to distribute the Altered Pressure directed at the Encapsulated Space at any point in time.
14. The PAM of item 1 where at least one internal piece and one external piece are united in a male and female connection optionally by reversible pressure fit and optionally where either the male or female piece is significantly softer than the other to aid sealing of the union.
15. The PAM of item 14 where the male-female union is created by at least one piece passing through the cover.
16. The PAM of items 1 and 14 where at least one piece passing through the covering is adapted to aid perforation or insertion through the covering.
17. The PAM of item 1 where the at least one Proximal piece forms a flange designed with a smooth planar surface on the Top and Bottom of the flange.
18. The PAM of item 1 where the at least one Proximal piece forms a flange designed with a non-planar surface on the Bottom of the flange.
19. A method of treating a wound with an Altered Pressure Apparatus utilizing a PAM as described in any of items 1-18.

II. Matrix Filled PAM Design

Referring to FIGS. 1-15, 17-27 and 34, preferred embodiments are disclosed. Broadly a PAM is provided to increase patient comfort and system efficacy by proving a PAM with a Proximal end accessing the Encapsulated Space that is at least partially filled with a porous matrix.

A best mode of the invention may employ one of the following configurations: at least a two piece design, a ring design, a coil design, a coaxial sheath design, a flap design, a non-planar surface design, a peripheral flange design, a peripheral protrusion design, a channel design, a manifold design, a Plenum design, an external PAM design or any design of tubular means.

One method of the invention may be operated by adding the porous matrix into the PAM at the time of application to the patent.

A second method of the invention may be operated by adding the porous matrix to the PAM as an integral step of prefabrication.

The embodiments are further described by the following aspects:
1. An Altered Pressure Apparatus with a terminating PAM comprising a Proximal interior at least partially filled of a porous matrix capable of wicking fluids from the exterior into the interior of the PAM.
2. The PAM of item 1 with the shape a polyhedronal shape bounded by squares, a polyhedronal shape bounded by rectangles, a polyhedronal shape bounded by a polygon, a 3-D round shape, a 3-D oval shape, a cylindrical shape, a tubular shape, any shape optionally closed ended and optionally with rounded right angles or edges.
3. The PAM of item 1 is a Plenum or a manifold configuration, either optionally with rounded right angles or edges.
4. The PAM of items 1-3 where the matrix is selected from the group of open-cell foam, a synthetic sponge, a natural sponge, a fibrotic compact, a fibrotic nest or any combination thereof.
5. The PAM of items 1-4 further comprising a Proximal end with a large percentage of open area to the Encapsulated Space, provided by increasing the length, size or count, individually or in combination, of the perforations within the PAM, thereby by providing ample alternative routes for gas and liquid influx while preventing prolonged intimate contact of opening interface with tissues and reducing resistance to flow.
6. A method of directing the movement from the Encapsulated Space into a PAM in an Altered Pressure Apparatus comprising at least partially filling the interior of a terminating PAM with a porous matrix capable of wicking fluids from the exterior into the interior of the PAM.
7. The method of item 6 further comprising the PAM of any of items 2-5.

III. Ring and Coil PAM Designs

Referring to FIGS. 5-8, preferred embodiments are disclosed. Broadly a PAM is provided to increase patient comfort, clinician administration convenience and system efficacy. The PAM comprises a Proximal end accessing the Encapsulated Space that is further comprised of a prefabricated tubular ring or coil.

A best mode of the invention employs a PAM fabricated to maintain its shape without further measures taken by the clinician. Another best mode locates the perforations in the interior diameter of the ring or between the coils to limit trauma and control extent of liquid removal.

One method of the invention may be operated by manually creating a ring PAM by the use of a "T" union insert forming the ring and a means to attach it to the Medial section of the PAM, further providing a ring that will maintain shape within the wound bed.

A second method of the invention may be operated by using thermal of other manufacturing means to create a memory in the coil, thereby providing a coil that will maintain shape within the wound bed.

The embodiments are further described by the following aspects:
1. An Altered Pressure Apparatus where the terminating PAM is a perforated tube ring at least partially contained within the Encapsulated Space.
2. The PAM of item 1 where the connection to the Medial section of the PAM is located, or emanates at least partially from, the inside diameter, outside diameter or Top of the ring.
3. The PAM of item 1 where the connection to the Medial section of the PAM emanates from more than one interface with the ring.
4. An Altered Pressure Apparatus where the terminating PAM is a perforated pig tail tube adapted to retain shape and size of coils, including manufacturing a memory or lower potential energy coil shape, at least partially contained within the Encapsulated Space.
5. An Altered Pressure Apparatus where the terminating PAM is a perforated pig tail tube adapted to retain shape and size of coils by application of flexible bands, ties or straps fixed to at least one coil at least partially contained within the Encapsulated Space.
6. An Altered Pressure Apparatus where the terminating PAM is a perforated pig tail tube adapted to retain shape and size of coils by application of a binding, tie, monofilament or small band transecting the coils at least partially contained within the Encapsulated Space.
7. A method of treating wound with an Altered Pressure Apparatus comprising fabricating a terminating PAM with a tubular means into a perforated tube ring and at least partially providing containment the ring within the Encapsulated Space.
8. The Altered Pressure Apparatus of item 7 comprising the PAM of any of items 1-6.

IV. Semisolid PAM Designs

Figure 14:
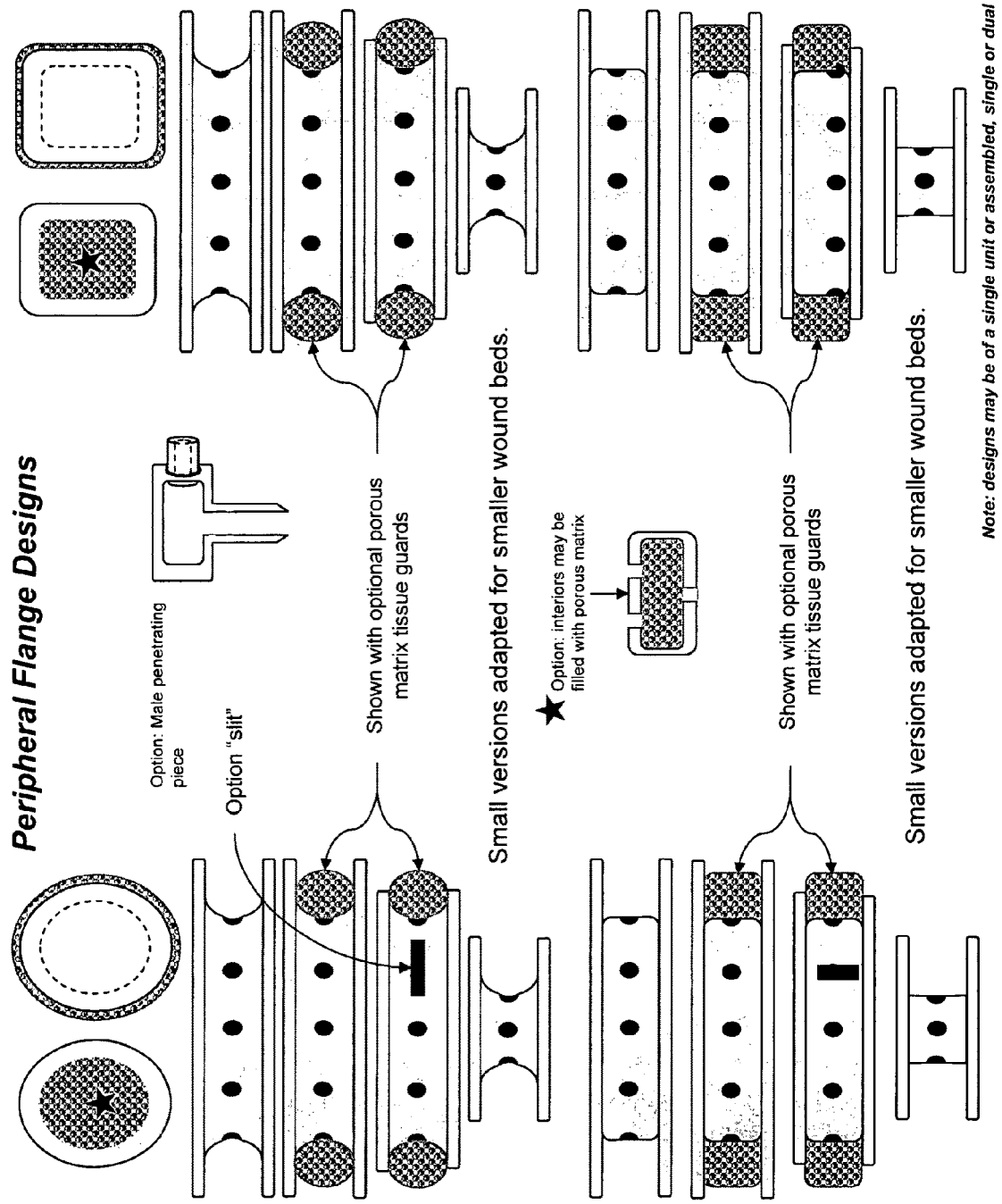
FIG. 14 shows cross-sectional views of various peripheral flange designs. The drawings further show design options including a porous matrix interior and matrix tissue guards.
Figure 15:
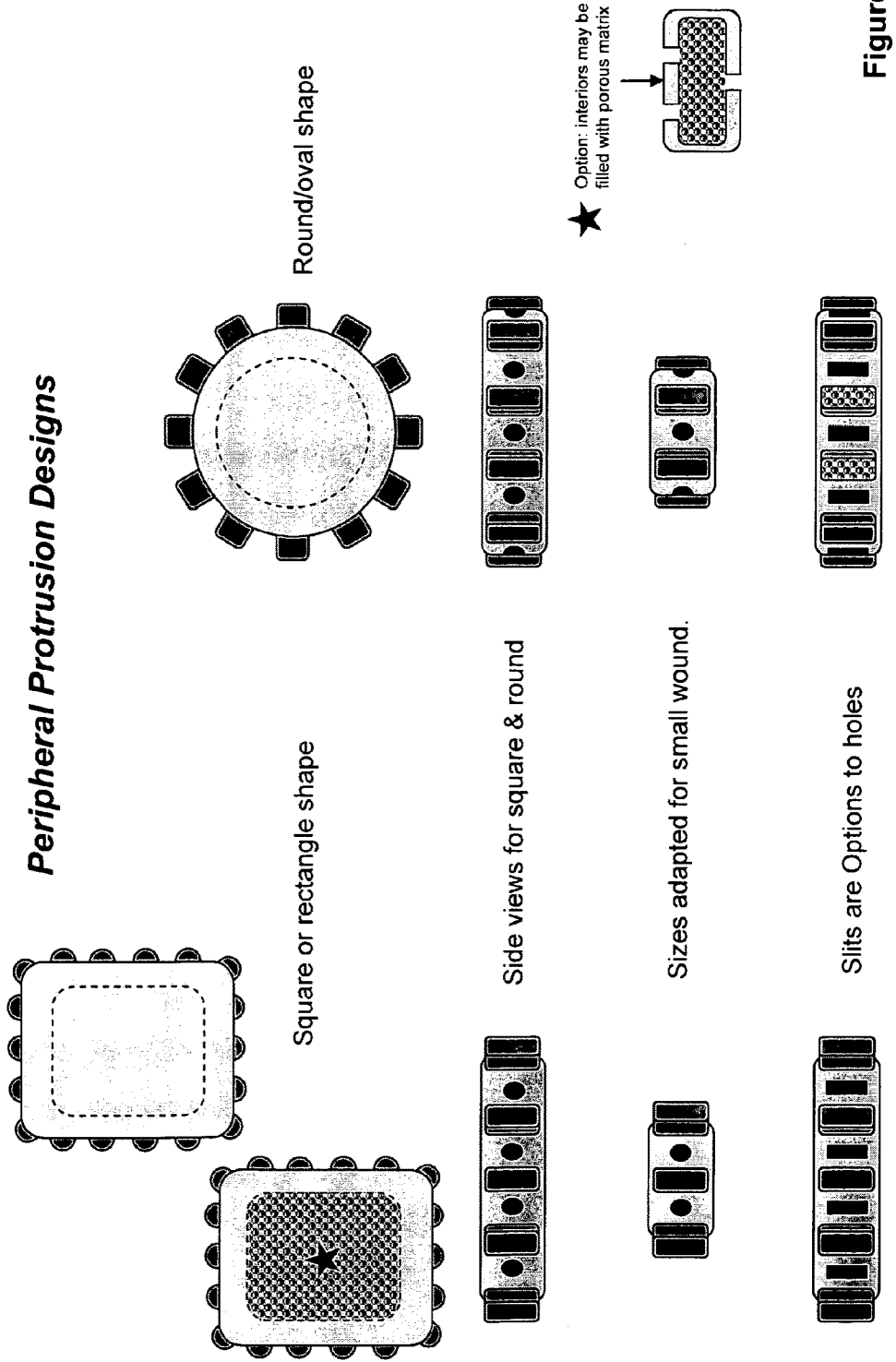
FIG. 15 shows Top down and side views of various peripheral protrusion designs. The drawings further show design options including a porous matrix interior.
Figure 16:
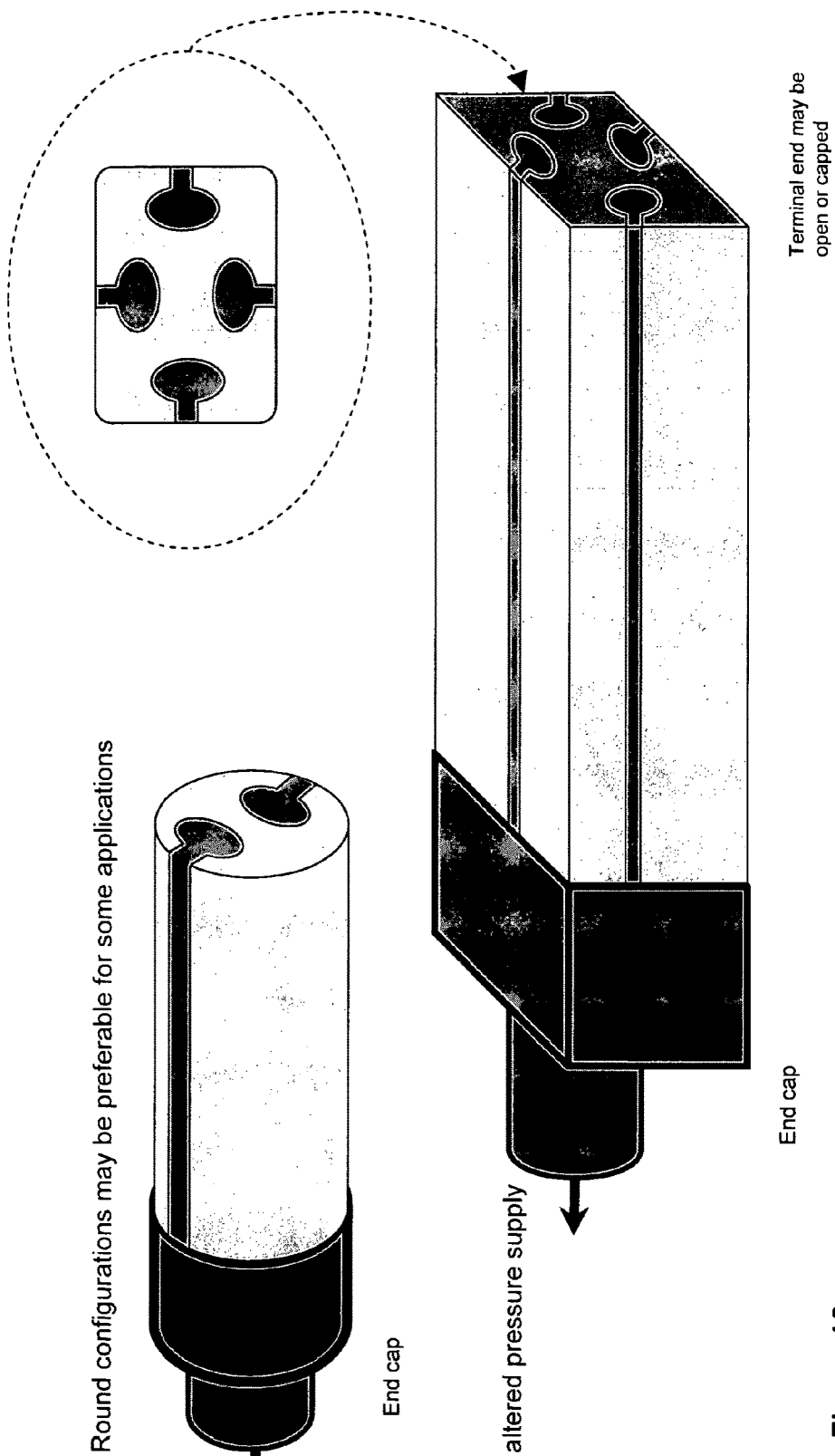
FIGS. 16 to 19 show cross-sectional and Top down views of various channel designs. The drawings further show design options including a porous matrix interior.
Figure 17:
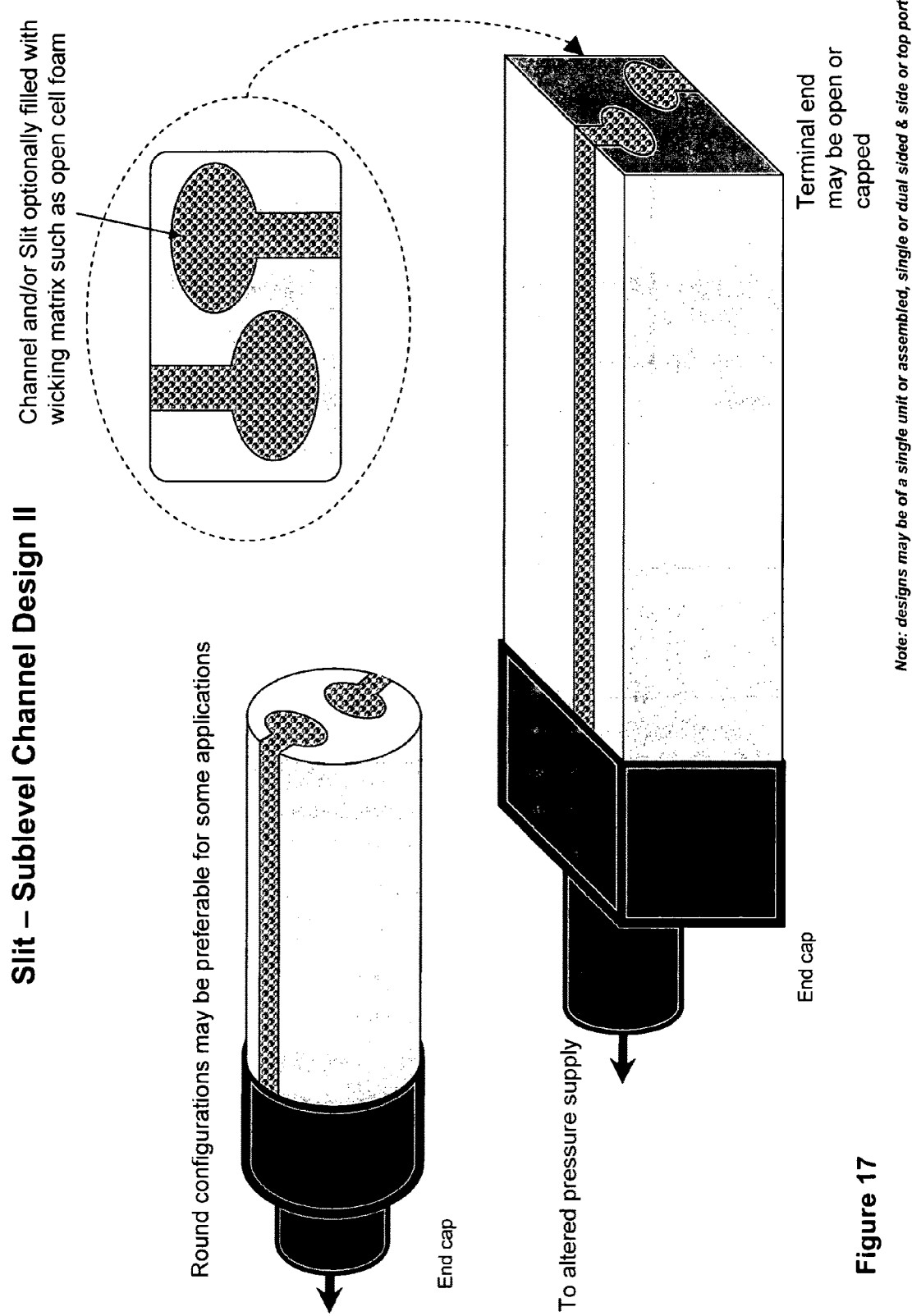
Figure 18:
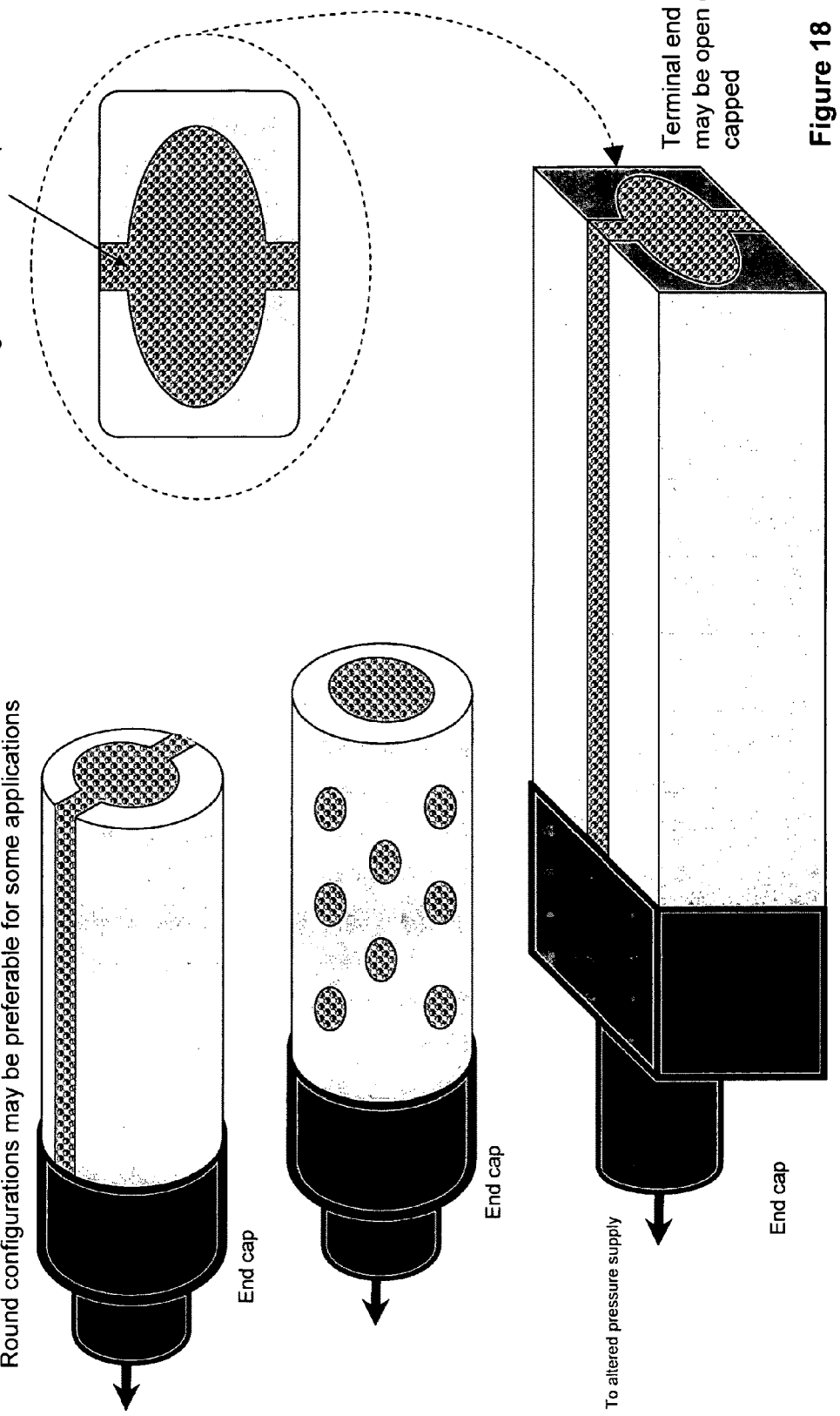
Figure 19:
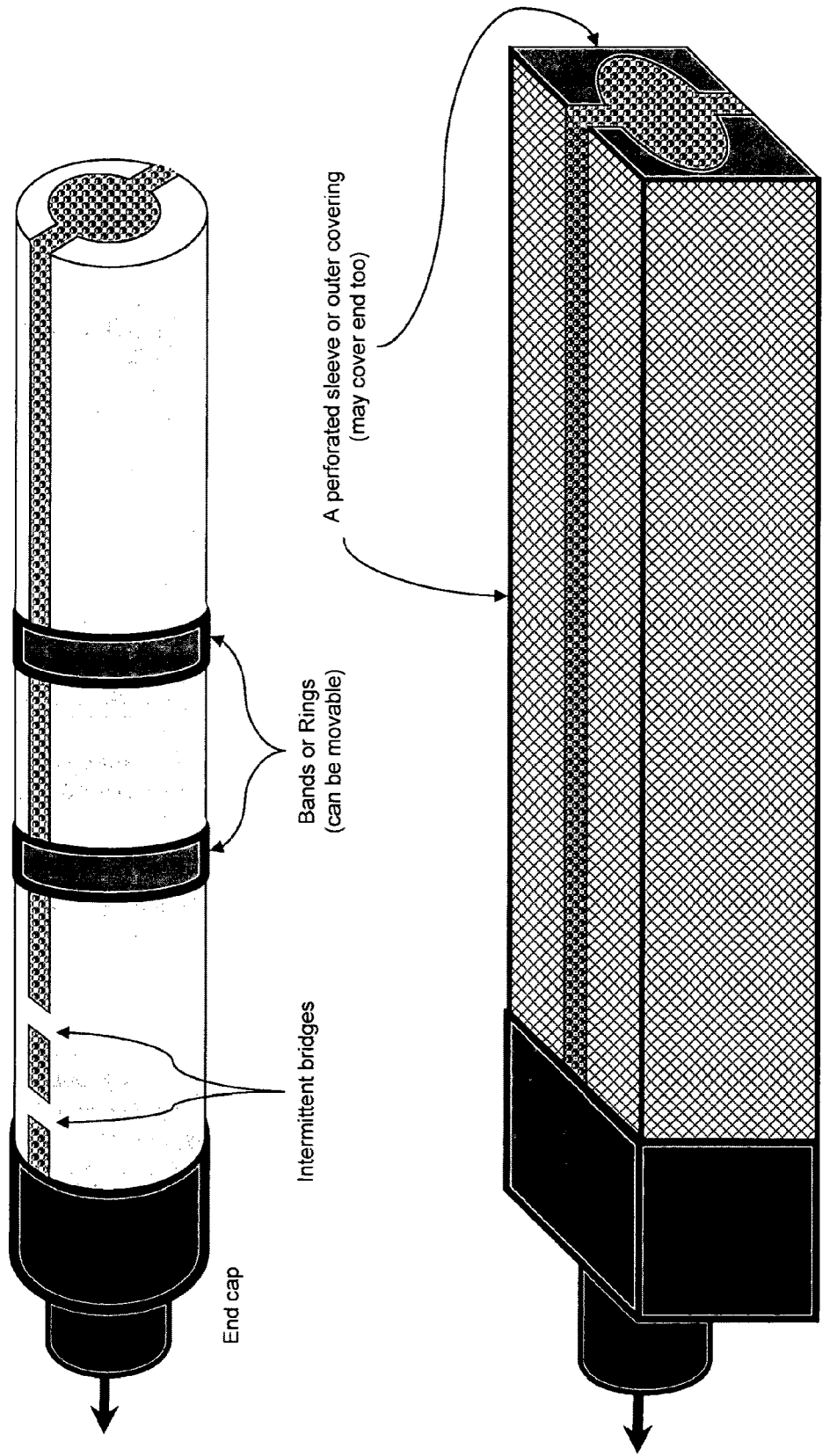
Figure 20:
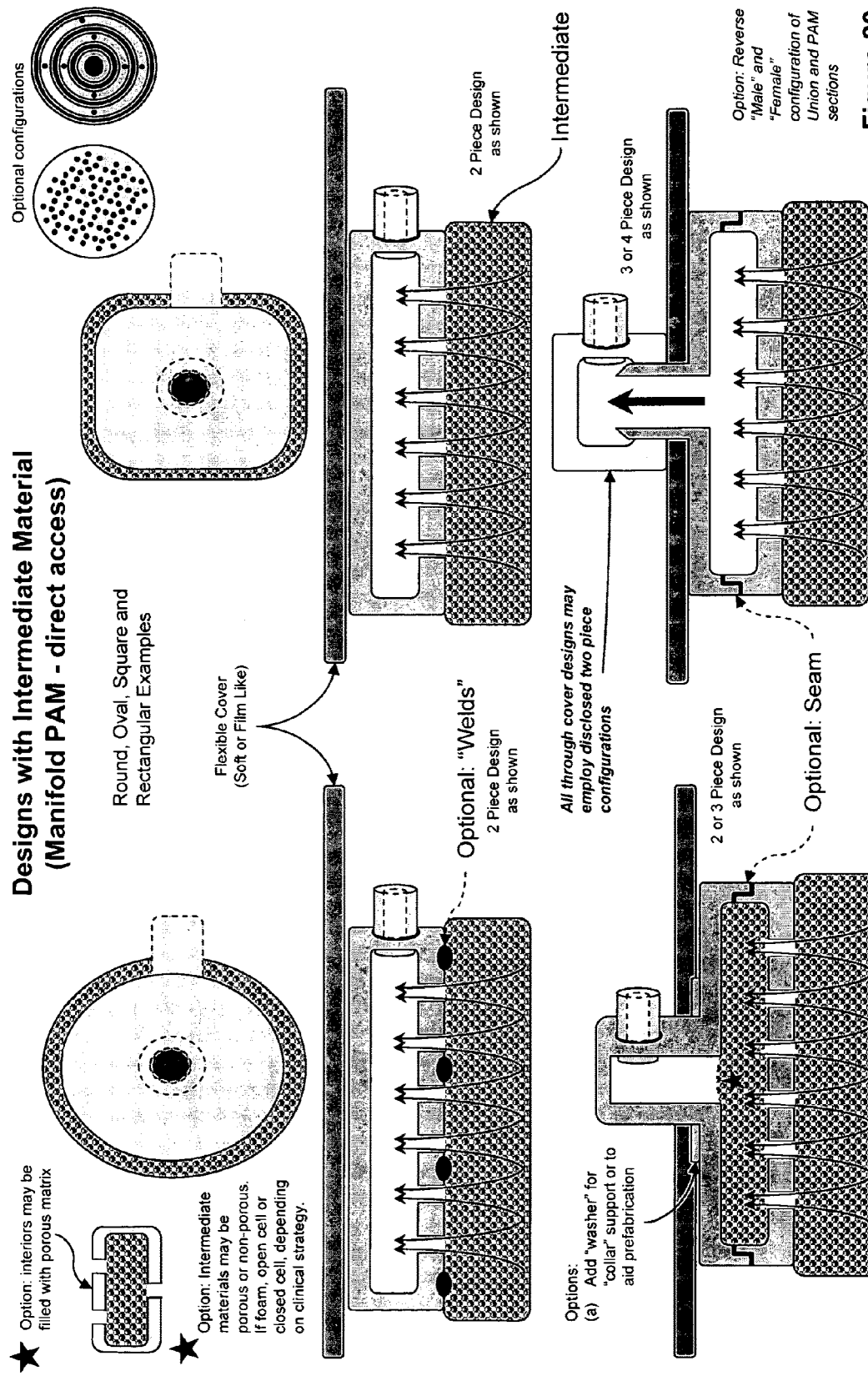
FIG. 20 shows a cross-sectional view of various manifold designs. These configurations also employ an optional Intermediate Material. The drawings further show samples of Top down views of typical shapes and design options including examples of various opening patterns, porous matrix interiors, washers for support or fixation, male/female connections and beveled elements to aid cover penetration.
Figure 21:
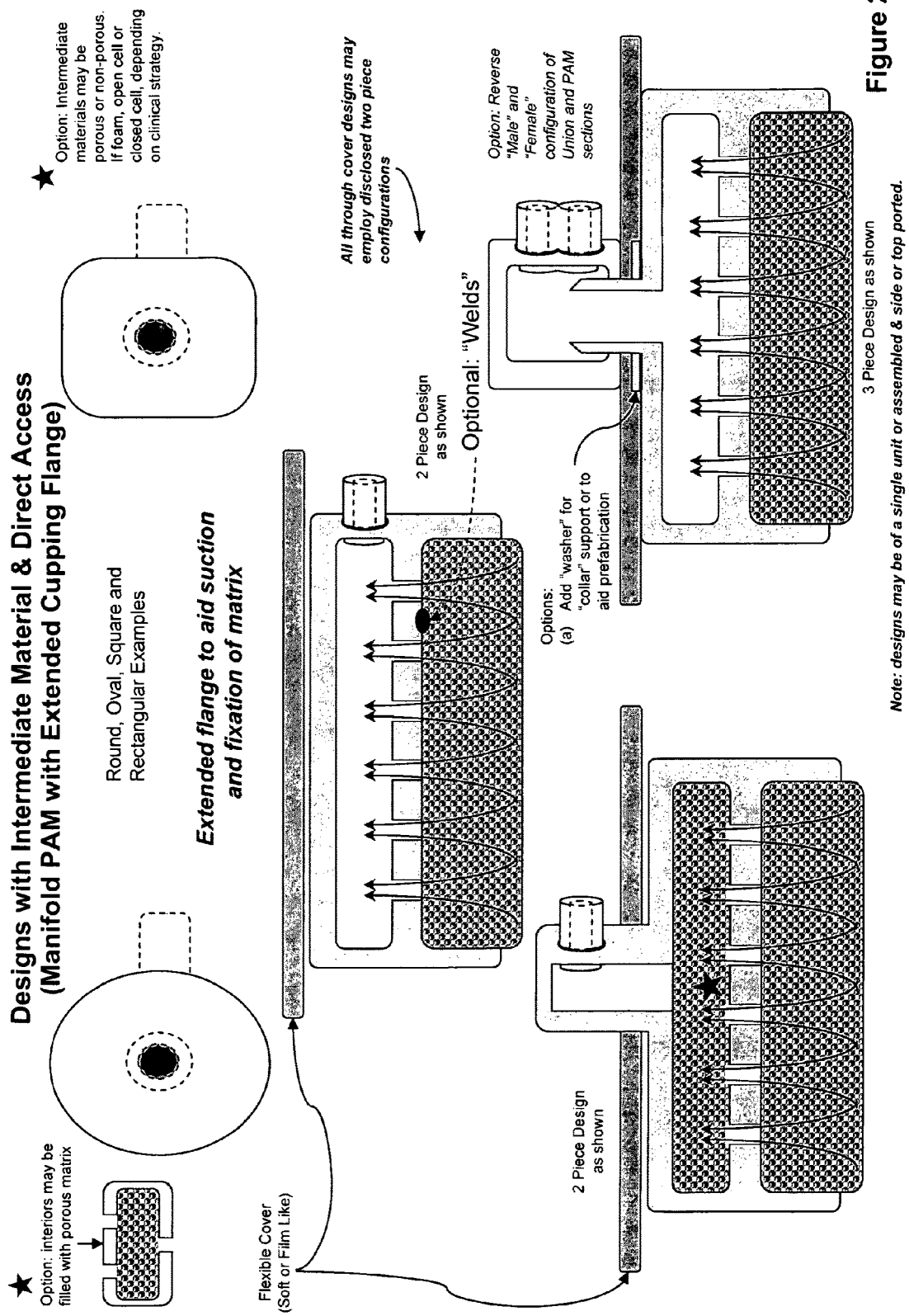
FIG. 21 shows a cross-sectional view of various manifold designs with an extended cupping flange. These configurations also employ an Intermediate Material. The drawings further show samples of Top down views of typical shapes and design options including porous matrix interiors, washers for support or fixation, male/female connections and beveled elements to aid cover penetration.
Figure 22:
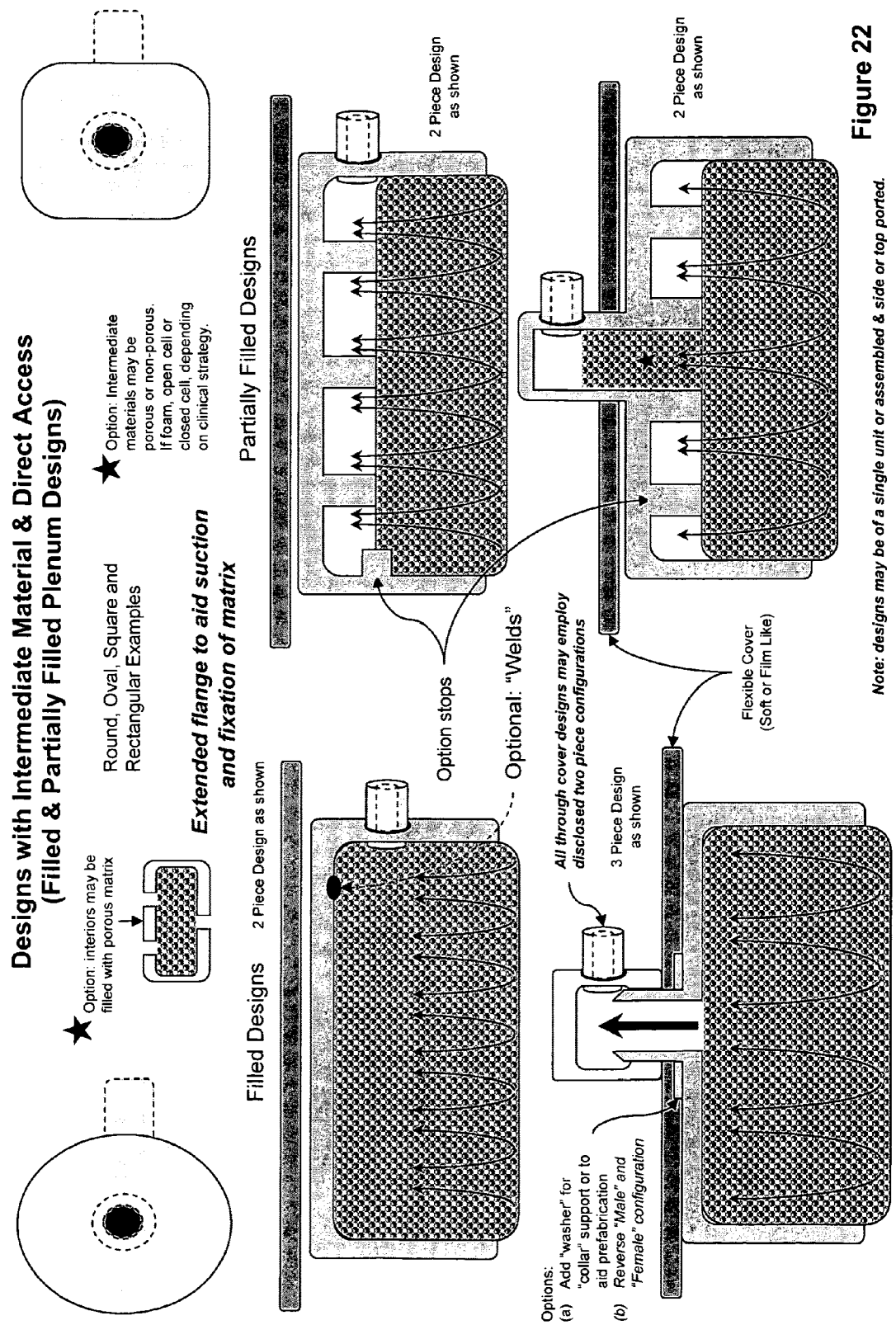
FIG. 22 shows a cross-sectional view of various filled Plenum designs. These configurations also employ an Intermediate Material. The drawings further show samples of Top down views of typical shapes and design options including porous matrix interiors, washers for support or fixation, male/female connections and beveled elements to aid cover penetration.
Figure 23:
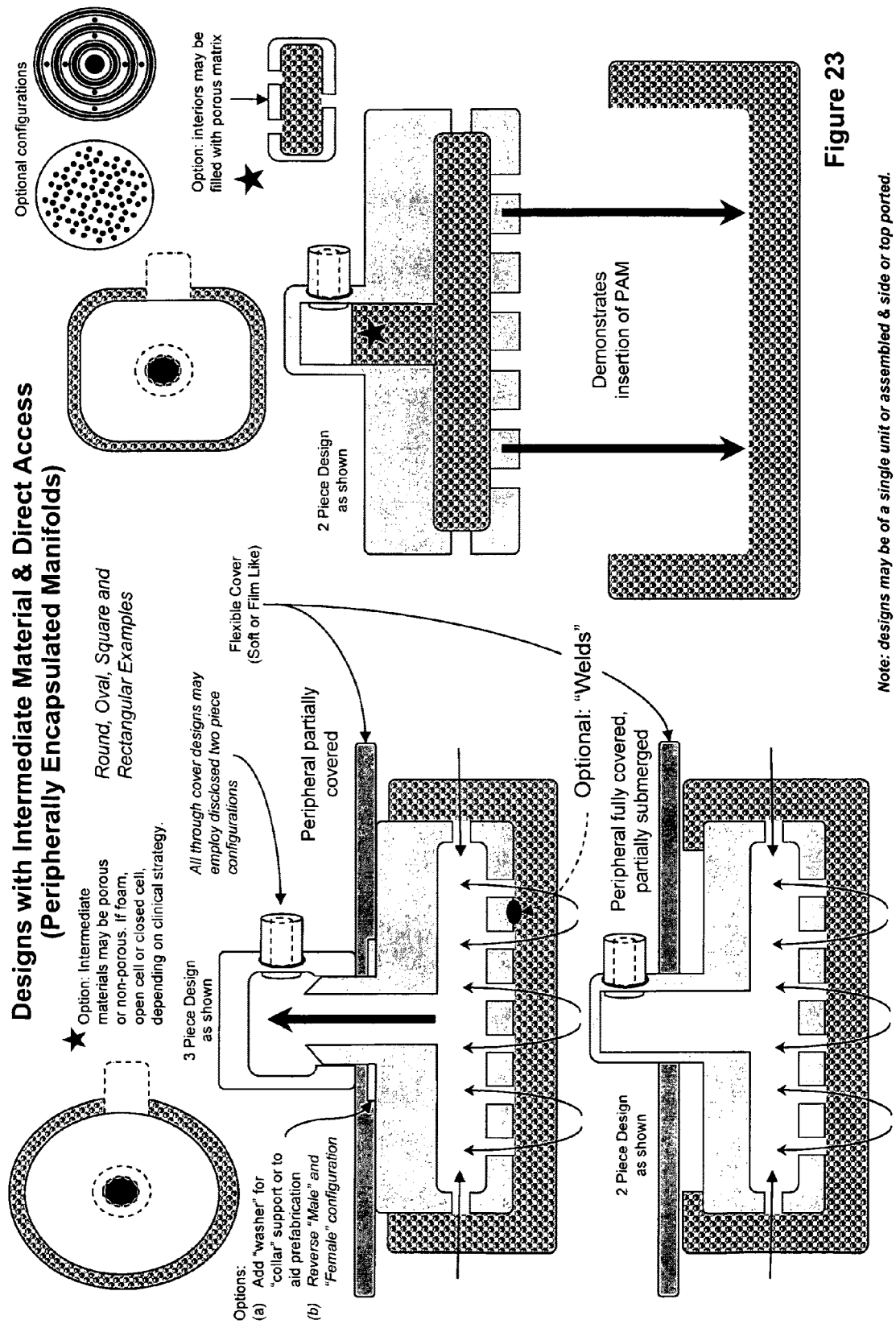
FIG. 23 shows a cross-sectional view of various peripherally encapsulated manifold designs. These configurations also employ an Intermediate Material. The drawings further show samples of Top down views of typical shapes and design options including examples of various opening patterns, porous matrix interiors, washers for support or fixation, male/female connections and beveled elements to aid cover penetration.
Figure 24:
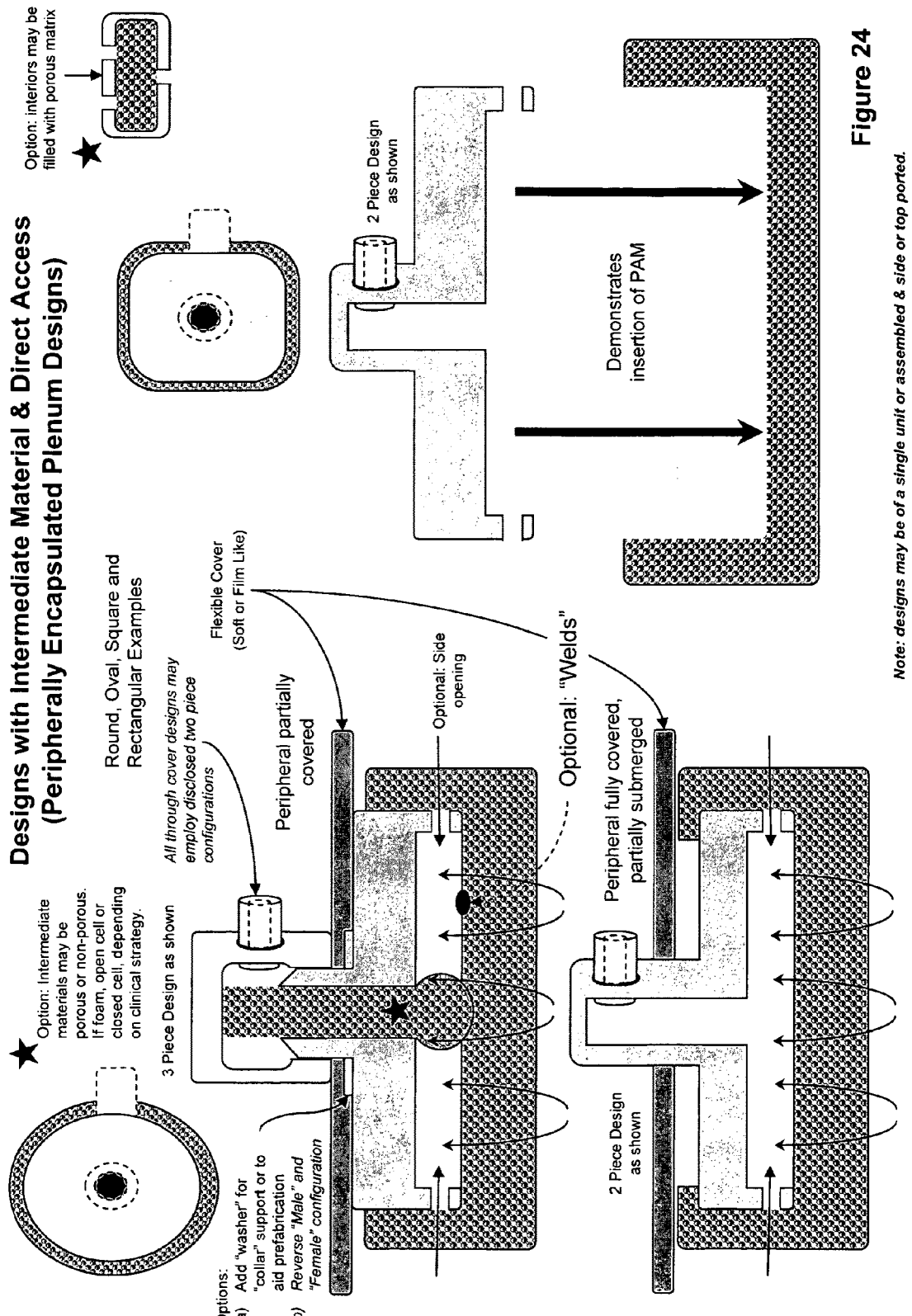
FIG. 24 shows a cross-sectional view of various peripherally encapsulated Plenum designs. These configurations also employ an Intermediate Material. The drawings further show samples of Top down views of typical shapes and design options including porous matrix interiors, washers for support or fixation, male/female connections and beveled elements to aid cover penetration.

Referring to FIGS. 9-10, FIGS. 3-5, 20-25 & 34 when used with an Intermediate and FIG. 14 when used with a matrix tissue guard, preferred embodiments are disclosed. Broadly PAM designs are provided to increase patient comfort, clinician administration convenience and system efficacy. The first PAM designs comprise a Proximal end accessing the Encapsulated Space that is further comprised of an outer sheath or peripheral flap. The remaining PAM designs employ foreign materials to prevent blockage of PAM openings.

A best mode of the invention employs a PAM fabricated with an outer sheath or peripheral flap of a biocompatible material such as a silicone derivative. Another preferred embodiment utilizes the sheath or flap design in conjunction with a semisolid as they are particularly adapted to limit clogging by semisolids.

A second best mode of the invention employs an Intermediate Material to prevent the blockage of the PAM with the semisolid.

One method of the invention may be operated by applying a semi-solid or gel into a wound bed prior to the application of the PAM.

A second method of the invention may be operated by coating or impregnating an Intermediate Material with the semi-solid or gel prior to application of the PAM.

The embodiments are further described by the following aspects:
1. An Altered Pressure Apparatus where the terminating PAM is a coaxial or outer sheath surrounding the primary Proximal end of the PAM at least partially contained within the Encapsulated Space, thereby preventing the partial or complete blockage of PAM openings with a semi-solid Therapeutic.
2. The Altered Pressure Apparatus of item 1 where the semi-solid Therapeutic is a hydrogel or lipogel.
3. An Altered Pressure Apparatus where the terminating PAM is a peripheral flap design at least partially contained within the Encapsulated Space, thereby preventing the partial or complete blockage of PAM openings with a semi-solid Therapeutic.
4. The Altered Pressure Apparatus of item 3 where the semi-solid Therapeutic is a hydrogel or lipogel.
5. A method of treating a wound with an Altered Pressure Apparatus in combination with a semi-solid comprising providing a terminating PAM with a means to prevent the semisolid from blocking the openings of the PAM.
6. The method of item 5 where Altered Pressure Apparatus further comprises a PAM of any of items 1-4.

V. PAM Designs to Limit Trauma

Referring to FIGS. 1-27, 32 and 34 preferred embodiments are disclosed. Broadly a PAM is provided to increase patient comfort and system efficacy. The PAM comprises a Proximal end accessing the Encapsulated Space that is further adapted to provide a means to inhibit direct tissue contact and blockage of openings in the pressure altering means, thereby reducing tissue trauma and pain created by intimate tissue contact with negative pressure interface at said openings.

A best mode of the invention employs a PAM fabricated with a non-planar or non-flat surface to inhibit said intimate tissue contact and blockage of openings located in recessed locations.

A second best mode utilizes an Intermediate Material between the tissue and the interface.

A third best mode utilizes a non-planar or non-flat between the tissue and the interface.

One method of the invention may be operated by fabricating the PAM with mounds and valleys, locating the opening in said valleys.

A second method of the invention may be operated by placing a porous or pierced Intermediate Material between the openings and tissues. Primary dressings including gauze, fibrotic weaves and closed cell and opened cell foams are examples of such Intermediate Materials. In an open cell configuration the foams provide superior wicking than many alternatives. In a closed cell, or even a fenestrated closed cell configuration, the foams provide superior exudate velocity and turnover at the tissue surface.

The embodiments are further described by the following aspects:
1. An Altered Pressure Apparatus where the terminating PAM is adapted to provide a means to inhibit direct tissue contact and blockage of openings in the PAM, thereby reducing tissue trauma and pain created by intimate tissue contact with negative pressure interface at said openings.
2. The Altered Pressure Apparatus of item 1 where the PAM is comprised of a non-planar or non-flat surface to inhibit said intimate tissue contact with openings.
3. The Altered Pressure Apparatus of item 2 where the PAM has openings located in recessed locations including valleys, troughs, lower plateaus, ravines, pockets, between flanges, between flaps, between protrusions, near unions or any combination thereof.
4. The Altered Pressure Apparatus of item 1 where the PAM is comprised of peripheral flanges or flaps, optionally with a porous matrix tissue guard.

5. The Altered Pressure Apparatus of item 1 where the PAM is comprised of peripheral protrusions, optionally with a porous matrix tissue guard.
6. The Altered Pressure Apparatus of item 1 where the PAM is comprised of slit accesses to multiple sublevel channels, optionally with a wicking matrix in the channels.
7. The Altered Pressure Apparatus of item 1 where the PAM is comprised of slit accesses to a central sublevel channel, optionally with a wicking matrix in the channel.
8. An Altered Pressure method of preventing trauma and pain due to intimate contact between terminating PAM openings and tissues comprising a means to inhibit tissue contact with and subsequent blockage of openings in the PAM.
9. The method of item 8 comprising the PAM of any of items 2-7.
10. The Altered Pressure Apparatus of item 1 where adaptation includes providing a PAM composed of a perforated tube shrouded in a peripheral porous matrix thereby preventing intimate tissue contact with openings.
11. The Altered Pressure Apparatus of item 1 where adaptation includes providing a PAM composed of a perforated tube with raised lateral continuous surfaces thereby preventing intimate tissue contact with openings.
12. The Altered Pressure Apparatus of item 1 where adaptation includes providing a PAM composed of a perforated tube with raised longitudinal continuous surfaces thereby preventing intimate tissue contact with openings.
13. The Altered Pressure Apparatus of item 1 where adaptation includes providing a PAM composed of a perforated tube with raised multiple protrusions thereby preventing intimate tissue contact with openings.
14. The Altered Pressure Apparatus of item 1 where adaptation includes providing a PAM composed of multiple perforated tubes adjoined at the midline with openings in close proximity to the unions thereby preventing intimate tissue contact with openings.
15. An Altered Pressure method of preventing trauma and pain due to intimate contact between terminating PAM openings and tissues comprising a means to inhibit tissue contact with and subsequent blockage of openings in the PAM.
16. The method of item 15 comprising the PAM of any of items 10-14.
17. The Altered Pressure Apparatus of item 1 where adaptation includes providing a PAM composed of perforated tube Rings adapted to resist rotation within the wound bed thereby preventing intimate tissue contact with openings of the interior circumference.
18. The Altered Pressure Apparatus of item 1 where adaptation includes providing a PAM composed of perforated pig tail tube adapted to retain shape and size of coils, including manufacturing a memory or lower potential energy coil shape, further adapted with the lateral perforations between the coils thereby preventing intimate tissue contact with openings.
19. The Altered Pressure Apparatus of item 1 where adaptation includes providing a PAM composed of perforated pig tail tube adapted to retain shape and size of coils by application of flexible bands or straps fixed to at least one coil, further adapted to block tissue from direct contact with the lateral perforations between the coils thereby preventing intimate tissue contact with openings.
20. An Altered Pressure method of preventing trauma and pain due to intimate contact between PAM openings and tissues comprising a means to inhibit tissue contact with and subsequent blockage of openings in the PAM.
21. The method of item 20 comprising the PAM of any of items 17-19.
22. The Altered Pressure Apparatus of item 1 where adaptation includes providing a PAM composed of a coaxial or outer sheath surrounding the primary Proximal end of the PAM thereby preventing intimate tissue contact with openings.
23. The Altered Pressure Apparatus of item 1 where adaptation includes providing a PAM composed of a peripheral flap design thereby preventing intimate tissue contact with openings.
24. An Altered Pressure method of preventing trauma and pain due to intimate contact between terminating PAM openings and tissues comprising a means to inhibit tissue contact with and subsequent blockage of openings in the PAM.
25. The method of item 24 comprising the PAM of any of items 22-23.
26. An Altered Pressure Apparatus where the terminating PAM is comprised of at least a two piece Proximal end, further comprising: (a) at least a portion of at least one piece located within the Encapsulated Space and positioned at least partially on Top of an Intermediate Material thereby preventing intimate tissue contact with openings, (b) at least a portion of at least one piece located outside of the Encapsulated Space, and (c) at least one portion of at least one piece passing through said covering, optionally with adhesive, support washers or heat welds for fixation and support.
27. The Altered Pressure Apparatus of item 26 where at least one piece of the PAM is located at least partially within the Encapsulated Space is not tubing.
28. The Altered Pressure Apparatus of item 26 where at least one piece of the PAM is located at least partially outside the Encapsulated Space is tubing.
29. The Altered Pressure Apparatus of item 28 where the tubing is completely outside the Encapsulated Space.
30. The Altered Pressure Apparatus of item 26 where the connection of internal and external pieces of the PAM forms one opening to the Encapsulated Space.
31. The Altered Pressure Apparatus of item 26 where the connection of internal and external pieces of the PAM forms multiple openings to the Encapsulated Space.
32. The Altered Pressure Apparatus of item 31 where the multiple openings of the PAM serves as a manifold to distribute the Altered Pressure directed at the Encapsulated Space at any point in time.
33. The PAM of item 26 where at least one internal piece and one external piece are united in a male and female connection optionally by reversible pressure fit and optionally where either the male or female piece is significantly softer than the other to aid sealing of the union.
34. The Altered Pressure Apparatus of item 33 where the male female union is created by at least one piece passing through the cover.
35. The Altered Pressure Apparatus of items 26 and 33 where at least one piece of the PAM passing through the covering is adapted to aid perforation or insertion through the covering, adaptation to include a beveled edge.

36. The PAM of item 26 where the at least one Proximal piece forms a flange designed with a smooth planar surface on the Top and Bottom of the flange.
37. The PAM of item 26 where the at least one Proximal piece forms a flange designed with a non-planar surface on the Bottom of the flange.
38. An Altered Pressure method of preventing trauma and pain due to intimate contact between terminating PAM openings and tissues comprising a means to inhibit tissue contact with and subsequent blockage of openings in the PAM.
39. The method of item 38 comprising the PAM of any of items 26-37.
40. The Altered Pressure Apparatus of items 1 and 26 where adaptation includes providing a PAM composed of a manifold positioned or attached at least partially on Top of an Intermediate Material thereby preventing intimate tissue contact with openings, optionally with adhesive or heat welds for fixation and optionally at least partially filled with a porous matrix.
41. The Altered Pressure Apparatus of items 1 and 26 where adaptation includes providing a PAM composed of an extended cupping flange manifold adapted to direct suction, positioned or attached at least partially on Top of Intermediate Material thereby preventing intimate tissue contact with openings, optionally with adhesive or heat welds for fixation.
42. The Altered Pressure Apparatus of items 1 and 26 where adaptation includes providing a PAM composed of a partially enclosed Plenum, positioned or attached at least partially on Top of Intermediate Material thereby preventing intimate tissue contact with openings, said Plenum encapsulating said Intermediate Material excluding a small peripheral margin and the surface of primary contact with the wound bed, optionally with adhesive or heat welds for fixation.
43. The Altered Pressure Apparatus of items 1 and 26 where adaptation includes providing a PAM composed of a manifold positioned or attached at least partially in Top of Intermediate Material thereby preventing intimate tissue contact with openings, said Intermediate Material rising to at least partially encapsulate the periphery of the manifold, optionally with adhesive or heat welds for fixation.
44. The Altered Pressure Apparatus of items 1 and 26 where adaptation includes providing a PAM composed of a Plenum positioned or attached at least partially on Top of Intermediate Material thereby preventing intimate tissue contact with openings, said Intermediate Material rising to at least partially encapsulate the periphery of the Plenum, optionally with adhesive or heat welds for fixation.
45. An Altered Pressure method of preventing trauma and pain due to intimate contact between terminating PAM openings and tissues comprising a means to inhibit tissue contact with and subsequent blockage of openings in the PAM.
46. The method of item 45 comprising the PAM of any of items 40-44.
47. The Altered Pressure Apparatus of items 1-46 where adaptation includes providing a PAM at least partially filled with a porous matrix thereby providing a capillary drive within the PAM.

Referring to FIGS. 3-5 and 20-24, preferred embodiments are disclosed. Broadly a PAM is provided to increase patient comfort and system efficacy. The PAM comprises a Proximal end accessing the Encapsulated Space that is further comprised of an Intermediate Material between the tissue and the PAM, thereby reducing tissue trauma and pain created by direct contact between the PAM and tissue. The best mode of the invention utilizes an Intermediate Material between the tissue and the interface.

One method of the invention may be operated by placing a porous or pierced Intermediate Material between the PAM openings and tissues. Primary dressings including gauze, fibrotic weaves and closed cell and opened cell foams are examples of such Intermediate Materials. In an open cell configuration the foams provide superior wicking. In a closed cell, or even a fenestrated closed cell configuration, the foams provide superior exudate velocity and turnover at the tissue surface.

The embodiments are further described by the following aspects:

1. An Altered Pressure Apparatus comprised of an Intermediate Material positioned at least partially between the tissue and terminating PAM, said PAM positioned or attached on Top of the Intermediate Material, thereby reducing pain and trauma from direct contact of the wound bed and the PAM.
2. A method of treating a wound with an Altered Pressure Apparatus while preventing trauma and pain due to direct contact of the a terminating PAM with wound tissues comprising: positioning an Intermediate Material at least partially between the tissue and a PAM, thereby reducing pain and trauma by eliminating direct contact of the wound bed and the PAM.

Figure 25:
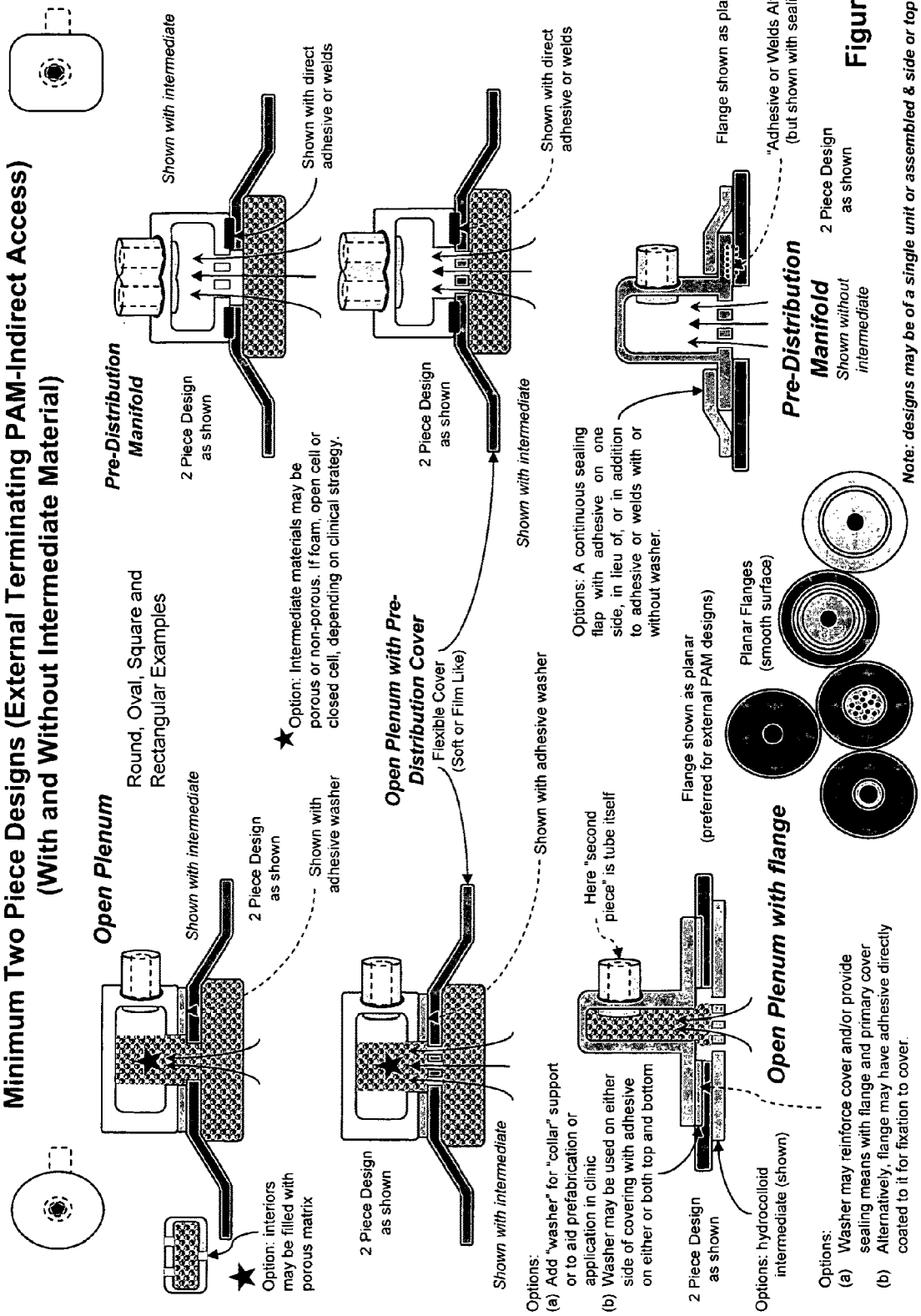
FIG. 25 shows a cross-sectional view of various minimum two piece external PAM designs. The configurations in the figure depict two designs of both external flange open Plenum designs. The configurations may also employ an Intermediate Material. The drawings further show samples of Top down views of typical shapes and design options including examples of various opening patterns, porous matrix interiors and washers for support or fixation. Male/female connections, while disclosed herein are not shown.
Figure 26:
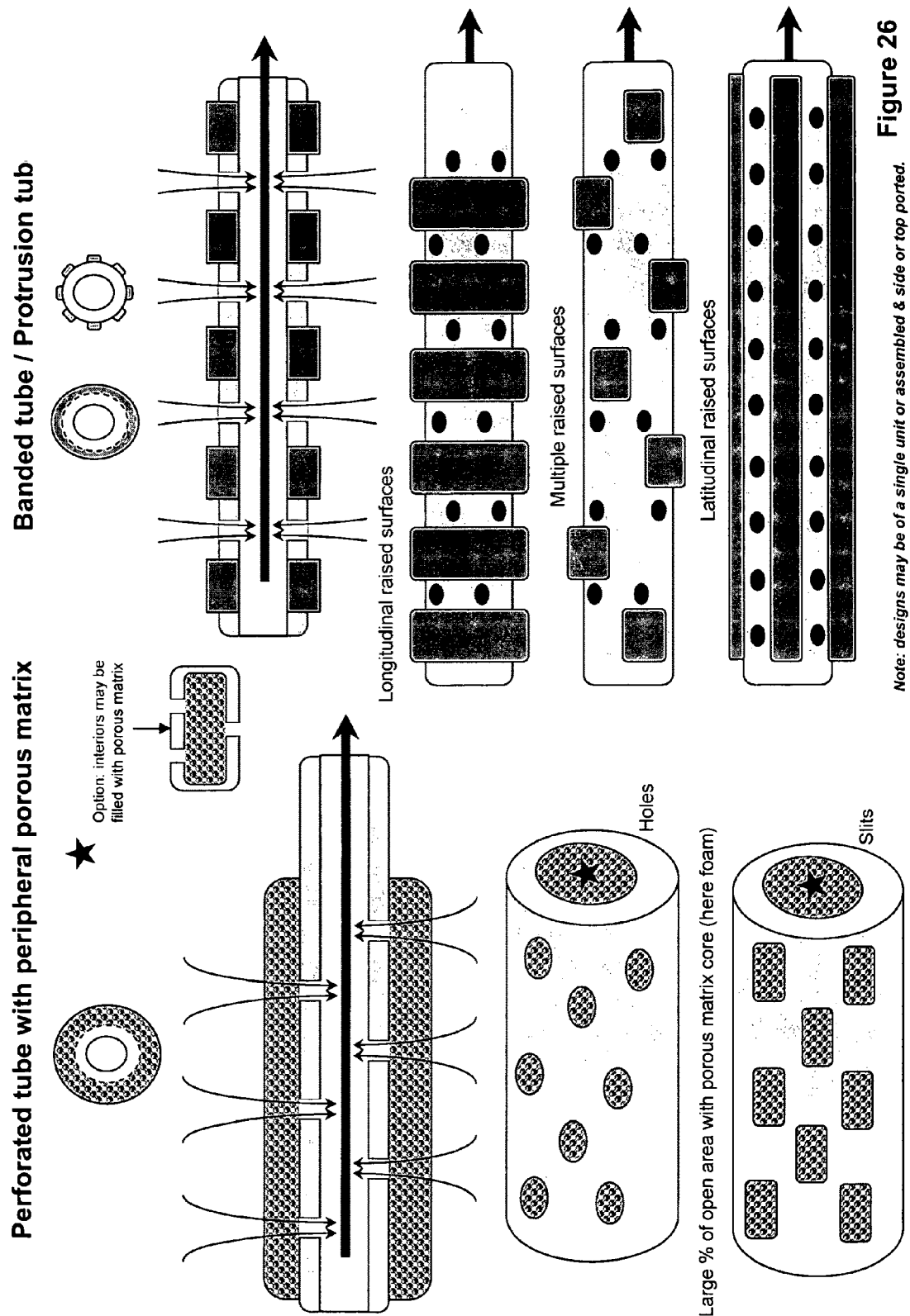
FIG. 26 shows a cross-sectional view of various tube designs with porous matrix peripheries, longitudinal protrusions, lateral protrusions and multiple protrusions all intend to inhibit tissue blockage and trauma. The drawings further show design options including a porous matrix interior.
Figure 27:
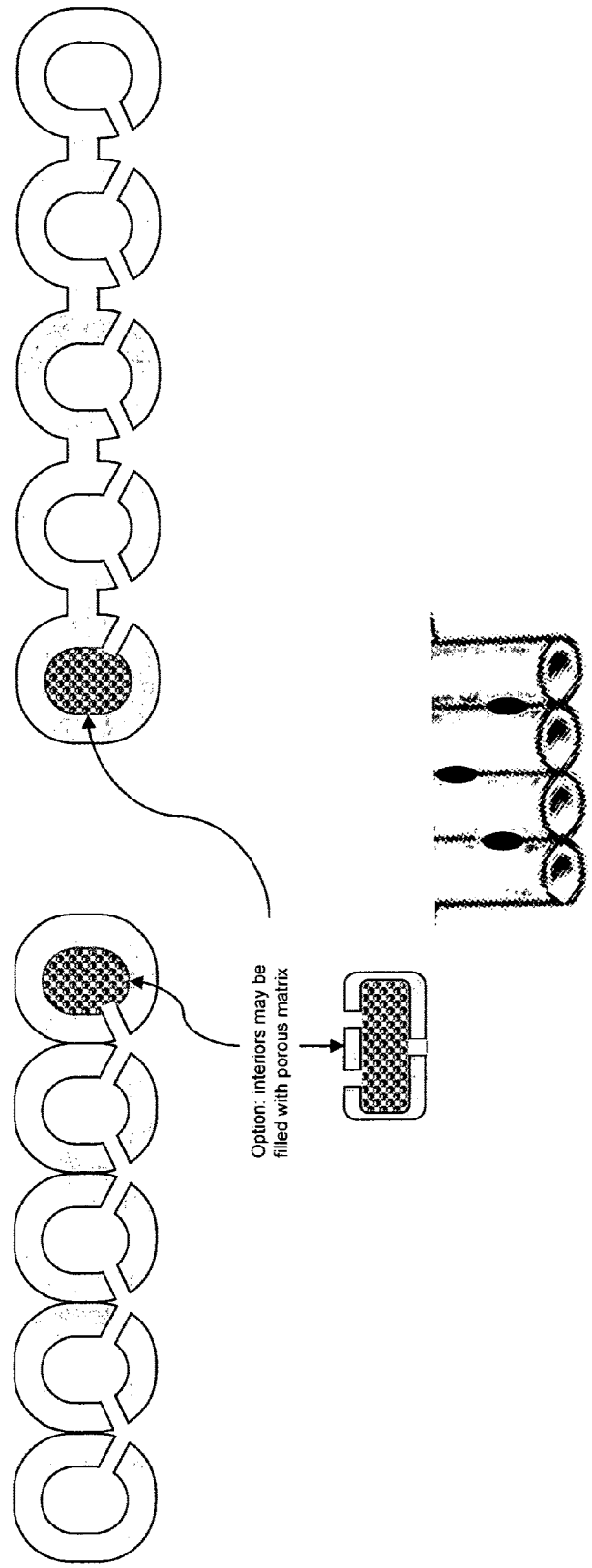
FIG. 27 shows a cross-sectional view of multiple tube designs, adjoined at the midline. The drawings further show design options including a porous matrix interior.

Referring to FIG. 25, a preferred embodiment is disclosed. Broadly a PAM is provided to increase patient comfort, clinician administration convenience and system efficacy. The PAM comprises a Proximal end at least partially filled with a porous matrix or comprising a manifold means with multiple openings, located external of the Encapsulated Space, positioned or attached on Top of the covering relating to one or more openings in the covering, an Intermediate Material positioned at least partially between the tissue and covering means including any opening, thereby reducing pain and trauma from direct contact of the wound bed and the covering means or PAM.

The best mode of the invention involves locating the PAM outside of the Encapsulated Space with a smooth planar surfaced Bottom adapted for fixation to the covering, said Encapsulated Space at least partially filled with an Intermediate Material.

A second best mode of the invention involves locating the PAM outside of the Encapsulated Space, where the PAM is further provided with a manifold to aid distribution of Altered Pressure initially and any fluid uptake by the PAM.

The embodiments are further described by the following aspects:

1. An Altered Pressure Apparatus comprised of a terminating PAM at least partially filled with a porous matrix to drive capillary action, located external of the Encapsulated Space, positioned or attached on Top of the covering relating to one or more openings in the covering, an Intermediate Material positioned at least partially between the tissue and covering means including any opening, thereby reducing pain and trauma from direct contact of the wound bed and the covering means or PAM.

2. An Altered Pressure Apparatus comprised of a terminating PAM with multiple openings located external of the Encapsulated Space, positioned or attached on Top of the covering relating to one or more openings in the covering, an Intermediate Material positioned at least partially between the tissue and covering means including any opening, thereby reducing pain and trauma from direct contact of the wound bed and the covering means or PAM.
3. An Altered Pressure Apparatus comprised of a terminating PAM with a smooth planar surfaced Bottom adapted for fixation to the covering, located external of the Encapsulated Space, positioned or attached on Top of the covering relating to one or more openings in the covering, an Intermediate Material positioned at least partially between the tissue and covering means including any opening, thereby reducing pain and trauma from direct contact of the wound bed and the covering means or PAM.
4. An Altered Pressure Apparatus comprised of a terminating PAM comprising a sealing ring bounded by at least one other ring or band, located external of the Encapsulated Space, positioned or attached on Top of the covering relating to one or more openings in the covering, an Intermediate Material positioned at least partially between the tissue and covering means including any opening, thereby reducing pain and trauma from direct contact of the wound bed and the covering means or PAM.
5. An Altered Pressure Apparatus comprised of a terminating PAM comprising a sealing ring with a smaller perimeter than the footprint of the affixed PAM, located external of the Encapsulated Space, positioned or attached on Top of the covering relating to one or more openings in the covering, an Intermediate Material positioned at least partially between the tissue and covering means including any opening, thereby reducing pain and trauma from direct contact of the wound bed and the covering means or PAM.
6. A method of treating a wound with an Altered Pressure Apparatus comprised reducing pain and trauma by utilizing a terminating PAM of any of items 1-5.

VI. Anti-Infectives and Altered Pressure

Broadly a preferred system is disclosed to increase patient comfort and system efficacy. The system comprises the utilization of Altered Pressure therapy to a wound in conjunction with an anti-infective.

The best mode of the invention involves the utility of a semisolid, preferably an anti-infective that is a lipid, preferably a fatty acid or fatty acid ester.

In second best mode, the lipid is adapted to semisolid by a viscous Liquid Crystal formation thereby resisting migration and removal in the Encapsulated Space.

In a third best mode, the semisolid is adapted to prevent adhesion of the dressing to the wound, thereby decreasing trauma upon dressing changes and improving overall patient comfort.

In a fourth best mode, the semisolid is adapted to efficiently fill void spaces in the wound, thereby improving performance of the therapy.

One method of the invention may be operated by applying the lipid to an Intermediate Material to increase patient comfort during therapy and dressing changes and limit bacterial growth within the wound. Another method of the invention may be operated by applying the lipid to the wound bed, moistening the lipid or Intermediate Material with saline, and then applying the Intermediate Material on Top of lipid. Another method is to coat the Intermediate Material with the lipid prior to application to the wound bed.

The embodiments are further described by the following aspects:

1. An Altered Pressure Apparatus used in combination with a local anti-infective or anti-biofilm agent.
2. The Altered Pressure Apparatus of item 1 where the anti-infective or anti-biofilm agent is a lipid.
3. The anti-infective or anti-biofilm agent of item 1 and 2 added as a component of an Intermediate Material useful for the inhibition of biofilms.
4. The Altered Pressure Apparatus of item 2 where the lipid is employed as a coating to inhibit growth of or harboring of pathogens within or upon any foreign material within the Encapsulated Space.
5. The Altered Pressure Apparatus of item 2 where the lipid is used in combination with additional anti-infectives including lactoferrin, bacterial phages, quorum sensing inhibitors, silver, methylene blue, gentian violet or sugar alcohols, growth promoting agents, anti-inflammatory agents, analgesics, anesthetics, debriding agents, derivatives of this group or any combination thereof.
6. The Altered Pressure Apparatus of items 2-5 where the lipid is composed of a fatty acid.
7. The Altered Pressure Apparatus of items 2-5 where the lipid is composed of a fatty acid ester.
8. The Altered Pressure Apparatus of items 2-7 where the lipid is adapted to form a Liquid Crystal before or after administration.
9. A method of treating a wound with an Altered Pressure Apparatus while retarding bacterial growth or biofilm formation comprising: administering an anti-infective or anti-biofilm agent within the Encapsulated Space.
10. The method of item 9 where the anti-infective or anti-biofilm agent is any of items 2-8.
11. The method of item 10 where the anti-infective or anti-biofilm agent is added as a component of an Intermediate Material useful for the inhibition of biofilms.
12. The Altered Pressure Apparatus of items 7-11 where the lipid is selected from the group of glyceryl monoarachidonate, glyceryl monolaurate, glyceryl monolinoleate, glyceryl monolinolenate, glyceryl monomyristate, glyceryl monopalmitoleate, glyceryl monooleate, and glyceryl monostearate; glyceryl monocaprate, glyceryl monocaprylate, glyceryl monococoate, glyceryl monocollagenate, glyceryl monoerucate, glyceryl monohydroxystearate, glyceryl monoisopalmitate, glyceryl monolinoleate, glyceryl monolinolenate, glyceryl monomyristate, glyceryl monopalmitate, glyceryl monopentadecanoate, glyceryl monopolyacrylate, glyceryl monotallowate, glyceryl monocthiopropionate, glyceryl monocundecylenate, isopropyl monoarachidonate, isopropyl monolaurate, isopropyl monolinoleate, isopropyl monolinolenate, isopropyl monomyristate, isopropyl monopalmitoleate, isopropyl monooleate, and isopropyl monostearate; methyl monoarachidonate, methyl monolaurate, methyl monolinoleate, methyl monolinolenate, methyl monomyristate, methyl monopalmitoleate, methyl monooleate, and methyl monostearate, propylene glycyl monoarachidonate, propylene glycyl monolaurate, propylene glycyl monolinoleate, propylene glycyl monolinolenate, propylene glycyl monomyristate, propylene glycyl monopalmitoleate, propylene glycyl monooleate, propylene glycyl monostearate, or combinations thereof and preferably glycerol monooleate or glycerol monoerucate if cost effective, highly viscous Liquid Crystalline states are ultimately desired.

13. An Altered Pressure Apparatus further comprising (a) a bulk collection means comprising at least one container for the temporary storage of wound products including those optionally selected from the group of fluid exudates, bacteria, wound debris, administered Therapeutics and combinations thereof; and (b) a semi-solid substance or composition within the Encapsulated Space.

14. The apparatus of item 13 where the semi-solid is Hydrophobic.

15. The apparatus of item 14 where the Hydrophobic semisolid further resist dissolution by polar wound exudates, dilution by polar wound exudate or other means to reduce the semisolid's viscosity or consistency thereby minimizing the clearance of the semisolid from the wound site by natural physiological means of clearance, clearance by negative pressure drainage or any combination thereof.

16. The apparatus of items 13-15 where the semi-solid contains a tissue growth enhancer including collagen, adenosine, nitric oxide generating agents, gelatin, collagen, whole blood, blood plasma, a blood products including platelets, prothrombin, thrombin, fibrin, fibrinogen, thromboplastin or a clotting factor, angiogenin, angiopoietin-1, a diacylglycerol, substance P, follistatin, an interleukin, a leptin, midkine, pleiotrophin, progranulin, proliferin, a transforming growth factor, a granulocyte colony-stimulating factor, a hepatocyte growth factor, a scatter factor, an epidermal growth factor, a nerve growth factor, a fibroblast growth factor, a keratinocyte growth factor, a placental growth factor, an endothelial cell growth factor, a platelet-derived growth factor, a tumor necrosis factor, vascular endothelial growth factor (VEGF), a vascular permeability factor, insulin-like growth factor, a hormone, a bone morphogenetic protein, an enzyme, an enzyme inhibitor, a stem cell, thrombin inhibitor, pepsin, derivatives of this group or any combination thereof.

17. The apparatus of items 13-15 where the semi-solid contains an anti-infective including lactoferrin, bacterial phages, quorum sensing inhibitors, silver, methylene blue, gentian violet, sugar alcohols, derivatives of this group or any combination thereof.

18. The apparatus of items 13-15 where the semi-solid contains an anti-inflammatory agent, analgesic, anesthetic, debriding agent or any combination thereof.

19. The apparatus of items 13-18 where the semi-solid is at least partially composed of a lipid.

20. The apparatus of items 13-18 where the lipid is at least partially composed of a fatty acid ester.

21. The apparatus of item 20 where the fatty acid ester is selected from the group of glyceryl monoarachidonate, glyceryl monolaurate, glyceryl monolinoleate, glyceryl monolinolenate, glyceryl monomyristate, glyceryl monopalmitoleate, glyceryl monooleate, and glyceryl monostearate; glyceryl monocaprate, glyceryl monocaprylate, glyceryl monococoate, glyceryl monocollagenate, glyceryl monoerucate, glyceryl monohydroxystearate, glyceryl monoisopalmitate, glyceryl monolinoleate, glyceryl monolinolenate, glyceryl monomyristate, glyceryl monopalmitate, glyceryl monopentadecanoate, glyceryl monopolyacrylate, glyceryl monotallowate, glyceryl monocthiopropionate, glyceryl monocundecylenate, isopropyl monoarachidonate, isopropyl monolaurate, isopropyl monolinoleate, isopropyl monolinolenate, isopropyl monomyristate, isopropyl monopalmitoleate, isopropyl monooleate, and isopropyl monostearate; methyl monoarachidonate, methyl monolaurate, methyl monolinoleate, methyl monolinolenate, methyl monomyristate, methyl monopalmitoleate, methyl monooleate, and methyl monostearate, propylene glycyl monoarachidonate, propylene glycyl monolaurate, propylene glycyl monolinoleate, propylene glycyl monolinolenate, propylene glycyl monomyristate, propylene glycyl monopalmitoleate, propylene glycyl monooleate, propylene glycyl monostearate, or combinations thereof and preferably glycerol monooleate or glycerol monoerucate if cost effective, highly viscous Liquid Crystalline states are ultimately desired.

22. The apparatus of items 19-20 where the lipid is at least partially composed of a fatty acid.

23. The apparatus of item 22 where the fatty acids include caprylic acid, capric acid, lauric acid, myristic acid, myristoleic acid, palmitic acid, palmitoleic acid, oleic acid, or combinations thereof.

24. The apparatus of items 13-23 where the semisolid is impregnated, coated or otherwise deposited upon or within a primary or Secondary Material positioned inside the Encapsulated Space.

25. An Altered Pressure Apparatus where any foreign object, including materials, within the Encapsulated Space is coated with a hydrogel or lipogel to improve patient comfort or biocompatibility.

26. The lipogel of item 25 at least partially created by the formation of a Liquid Crystal before or after administration.

27. Where the lipogel of items 25-26 is at least partially composed of a fatty acid.

28. Where the lipogel of items 25-26 is at least partially composed of a fatty acid ester or diester.

29. Where the lipogel of item 28 is composed of at least partially glyceryl monooleate or glyceryl monoerucate.

30. A method of treating a wound with an Altered Pressure Apparatus while improving patient comfort or biocompatibility of wound objects comprised of coating any foreign object, including materials, within the Encapsulated Space with a hydrogel or lipogel.

31. The method of item 24 where the lipogel is any of items 26-29.

32. A method of controlling pathogen growth, reducing patient pain and/or augmenting the healing process intended for use with an Altered Pressure Apparatus for wound therapy comprising: utilization of a semisolid in conjunction with the Altered Pressure therapy.

33. The method of item 32 where the semi-solid is any of items 14-24.

34. A method of increasing patient comfort for use with an Altered Pressure Apparatus for wound therapy comprising: utilization of a semisolid in conjunction with the Altered Pressure therapy, thereby providing a semisolid cushioning means and at least partial barrier between the wound bed and a Primary Material, a Secondary Material, a PAM or any combination thereof.

35. The method of item 34 where the semi-solid is any of items 14-24.

36. The method of items 34-35 where the semisolid further limits tissue in-growth into a primary or Secondary Material, thereby providing further patient comfort upon dressing changes.

37. The method of items 34-35 where the semisolid further serves as a lubricant or anti-adhesive, preventing the adhesion of foreign materials to the wound bed, thereby providing further patient comfort upon dressing changes.

38. A method of filling tissue voids for use with Altered Pressure wound therapy comprising utilization of a semisolid, thereby providing a malleable means to fill or coat tissue valleys and voids.

39. The method of item 38 where the semi-solid is any of items 14-24.

40. The method of item 38 where the semisolid is any of items 7-8 and further provides a means for hemostasis.

41. The method of item 39 where the semisolid provides a means to inhibit biofilm formation.

42. The method of item 38 where the semisolid is any of items 7-8 and further provides a means to inhibit drying or maceration of the wound bed.

43. The method of item 38 where the semisolid is biodegradable.

44. A method of directing exudate flow to the outside margins of a foreign material in the Encapsulated Space during Altered Pressure wound therapy comprising the utilization of a Hydrophobic semisolid in combination with a porous foreign material within the Encapsulated Space, thereby restricting exudate flow through the porous foreign material.

45. The method of item 44 where the semi-solid is any of items 14-24.

VII. Device to Control Pressure

Figure 28:
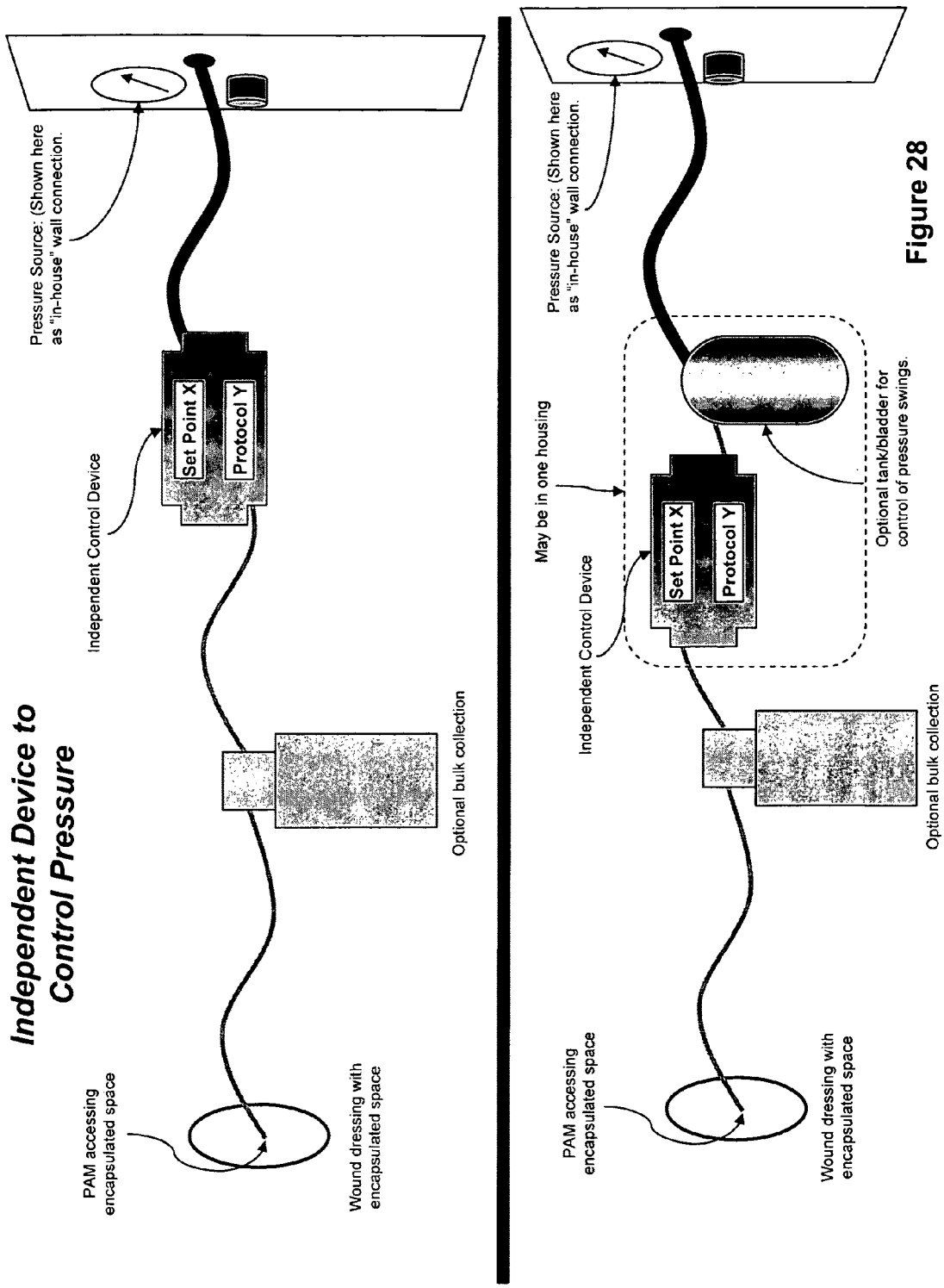
FIG. 28 shows an independent pressure control device. The drawings further show design options including a bladder or reservoir tank to limit pressure swings that may result from primary sources.

Referring to FIG. 28, a preferred embodiment is disclosed. Broadly a control device is provided to increase patient comfort, clinician administration convenience and system efficacy. The device provides a means for connecting an Altered Pressure source to a PAM and controlling pressures within the PAM from the source.

The best mode of the invention involves the device controlling the in-wall or "house" pressure sources located in a patient's room, suite or location. In this best mode, the device comprises a pressure regulation means to maintain the pressure within the PAM to a value different from the source pressure, a means of logic control of all functions including a batch or treatment regimen, and optionally the following: (a) a means of programmable logic, (b) a shut off means to the pressure source, (c) a relief means to return the PAM pressure to atmospheric, (d) a means of determining duration of treatment related to compliance, (e) a means for alarms to assist operator awareness of regimen stage, (f) a means of alarms for malfunction, (g) a means of alarms for maintenance, (h) a means to prevent reverse aspiration and (i) a means of alarms for leaks. In a second best mode, the device also comprises a tank, reservoir or bladder component in order to buffer significant deviations in pressure supplied by the pressure source. In a third best mode, referring to FIG. 4, dual Lumen tubing or conduit provides a means for a feedback loop to the pressure regulation means.

One method of the invention may be operated by connecting the house Altered Pressure source to the device, setting the house pressure source to a level exceeding the desired pressure in the PAM and subsequently allowing the device to control the PAM pressure in a protocol driven course of therapy as a batch or therapeutic regimen.

The embodiments are further described by the following aspects:

1. A device comprised of a means for connecting, directly or indirectly, an Altered Pressure source to a PAM, said device further comprised of a means to control pressures in the PAM to those specified by the protocol for therapy.

2. The device of Item 1 where the means to control pressures comprises features optionally selected from the group of (a) a pressure regulation means to maintain the pressure within the PAM to a value different from the source pressure, (b) a shut off means to the pressure source, (c) a relief means to return the PAM pressure to atmospheric, (d) a means of logic control of all functions, (e) a means of programmable logic, (f) a means of determining duration of treatment related to compliance, (g) a means for alarms to assist operator awareness of regimen stage, (h) a means of alarms for malfunction, (i) a means of alarms for maintenance, (j) a means of alarms for leaks, (k) a means to prevent reverse aspiration, and any combination thereof.

3. The device of Items 1-2 where the pressure source is the in-wall, house or another provided utility source for Altered Pressure located in a patient's room, suite or location.

4. The device of Items 1-2 where the device comprises a tank, reservoir or bladder component to aid control or regulation to a specified pressure by buffering significant deviations in pressure from the pressure source.

5. The device of Items 1-2 where the device comprises a means to provide supplementary Altered Pressures in the event of an emergency, a mechanical failure, capacity shortage or otherwise loss of effective function of the primary Altered Pressure source.

6. The supplementary means of Item 5 selected from the group of a negative pressure means, a positive pressure means, a power source including a battery, a means for control of the supplementary means, a means to interface with the devices programmable logic control and any combination thereof.

7. A method of treating a wound with an Altered Pressure Apparatus comprising controlling the pressure within the PAM by a device independent from the primary Altered Pressure source and any controlling means thereof.

8. The method of item 7 where the device is any of items 1-6.

9. An Altered Pressure Apparatus further comprising: (a) a bulk collection means comprising at least one container for the temporary storage of wound products including those optionally selected from the group of fluid exudates, bacteria, wound debris, administered Therapeutics and combinations thereof; and (b) the device of any of items 1-6.

VIII. Venturi Therapy

Figure 29:
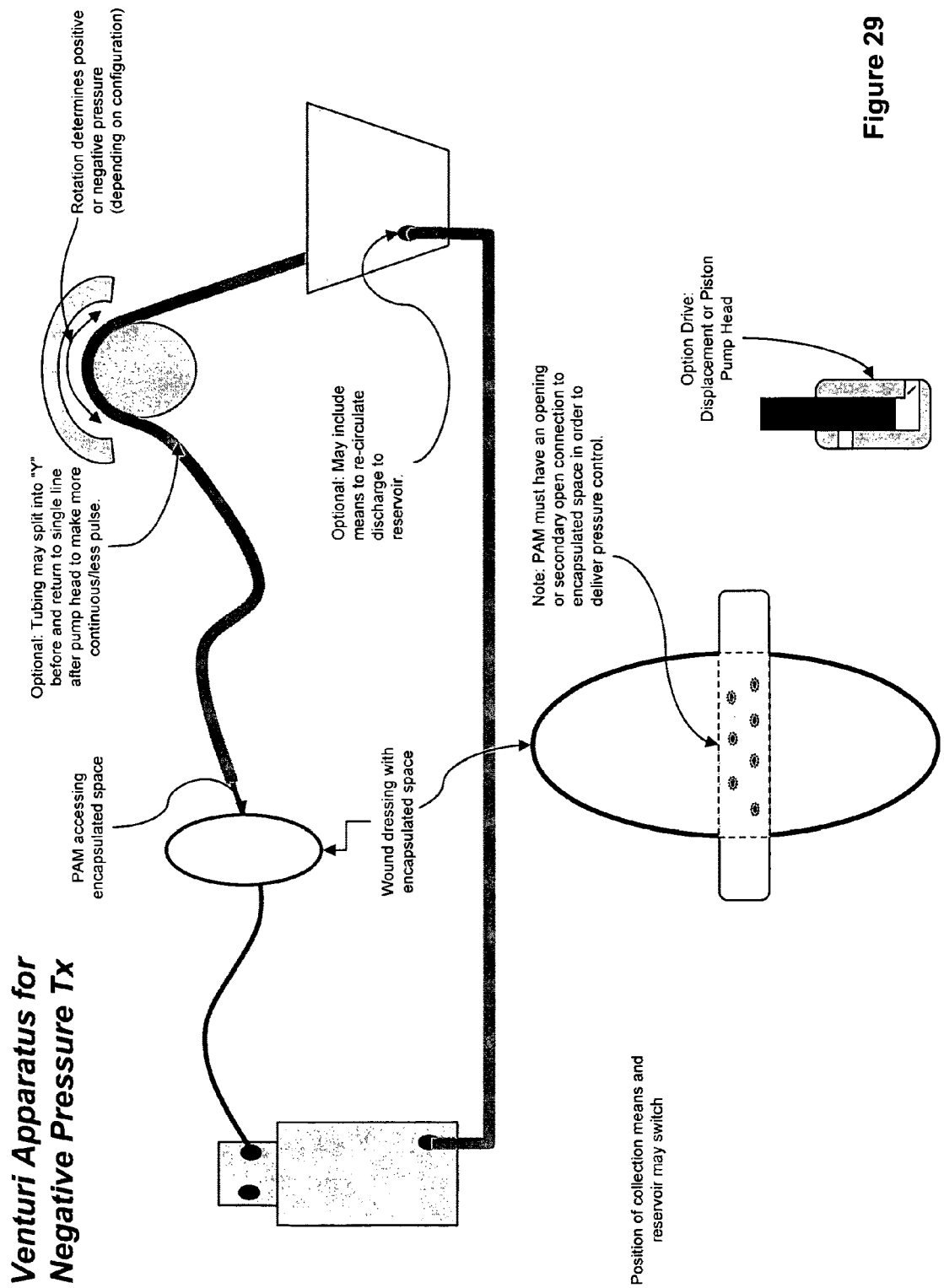
FIG. 29 shows a venturi apparatus to deliver negative pressure wound therapy. The drawings further show design options including a re-circulation means for fluids.

Referring to FIG. 29, a preferred embodiment is disclosed. Broadly an apparatus is provided for negative pressure wound therapy to increase patient comfort and system efficacy. The device and method comprises a covering means adapted to protect a wound from contamination and/or trauma; a sealing means for establishing intimate but reversible contact with the perimeter of said covering to surrounding skin surfaces of said wound, thereby creating an Encapsulated Space, including the wound bed under said covering; the sealing means further providing a seal competent enough to provide treatment of the wound with pressures purposefully altered from atmospheric, including higher and lower pressures; a pressure altering means for interfacing non-atmospheric pressures with the said Encapsulated Space, said pressure altering means working in combination with said covering and sealing means to maintain the so desired Encapsulated Space pressures; the pressure altering means comprising a Proximal end, a Medial section and a Distal end; the pressure altering means adapted to deliver negative pressures via venturi aspiration from Medial section of PAM, a reservoir means for holding a gas or liquid prior to flow through PAM; a bulk collection means for collection of discharge from PAM; a pump for delivering the initial pressure differential to the pressure altering means.

The best mode of the invention involves an order of configuration beginning at the reservoir, through the Proximal end of the PAM, through the Medial section of the PAM within Encapsulated Space, through or by the pump and finally through the Distal end of the PAM into the bulk collection means. A second best mode involves utilizing the lines providing the venture aspiration also provide a means to alter wound bed temperature.

One method of the invention may be operated connecting a fluid reservoir by way of a PAM that passes through the Encapsulated Space directly, connecting the PAM to tubing specified for a peristaltic pump and terminating the tubing into a discharge collection vessel. A second method may be operated by adding a recirculation means to the discharge vessel and the reservoir, controlling the temperature of the reservoir and allowing only a branch of the PAM to enter the Encapsulated Space.

The embodiments are further described by the following aspects:

1. A Venturi Aspiration Apparatus for negative pressure wound therapy comprising: (a) a covering means adapted to protect a wound from contamination and/or trauma; (b) a sealing means for establishing intimate but reversible contact with the perimeter of said covering to surrounding skin surfaces of said wound, thereby creating an Encapsulated Space, including the wound bed under said covering; (c) the sealing means further providing a seal competent enough to provide treatment of the wound with pressures purposefully altered from atmospheric, including higher and lower pressures; (d) a PAM for interfacing non-atmospheric pressures with the said Encapsulated Space, said PAM working in combination with said covering and sealing means to maintain the so desired Encapsulated Space pressures; (e) the PAM comprising a Proximal end, a Medial section and a Distal end; (f) the PAM adapted to deliver negative pressures via venturi aspiration from Medial section of PAM, (g) a reservoir means for holding a gas or liquid prior to flow through PAM; (h) a bulk collection means for collection of discharge from PAM; (i) a pump for delivering the initial pressure differential to the PAM; and (j) an order of configuration beginning at the reservoir, through Proximal end of the PAM, through the Medial section of the PAM within Encapsulated Space, through or by the pump and finally through the Distal end of the PAM into the bulk collection means.
2. The Venturi Aspiration Apparatus of item 1 further consisting of a Medial section venturi aspiration means with direct physical access to the Encapsulated Space through an opening or conduit through said covering.
3. The Venturi Aspiration Apparatus of item 1 further consisting of a Medial section venturi aspiration means with direct physical access to the Encapsulated Space through a passage created between skin and sealing means of said covering.
4. The Venturi Aspiration Apparatus of item 1 further consisting of a Medial section venturi aspiration means with indirect access to the Encapsulated Space though a void or opening in said cover.
5. The Venturi Aspiration Apparatus of item 1 further consisting of a Proximal end with indirect access to the Encapsulated Space through a passage created between skin and sealing means of said covering.
6. The Venturi Aspiration Apparatus of item 1 where the lines providing the venture aspiration also provide a means to alter wound bed temperature by regulation of the gas or liquid temperature providing the venturi aspiration.
7. The reservoir or collection means of item 1 composed of a means of controlling the liquid temperature within a specified a range, thereby providing a means to alter temperatures within the Encapsulated Space.
8. The Venturi Aspiration Apparatus of item 1 where the reservoir and collection means are connected by a conduit thereby adapting the reservoir for recirculation.
9. The Venturi Aspiration Apparatus of item 1 where any liquid contained in the reservoir contains an anti-infective agent selected from the group of antibacterial, antiviral, antifungal or any combination thereof.
10. A method of treating a wound with an Altered Pressure Apparatus further comprising: (a) providing a covering means adapted to protect a wound from contamination and/or trauma; (b) employing a sealing means for establishing intimate but reversible contact with the perimeter of said covering to surrounding skin surfaces of said wound, thereby creating an Encapsulated Space, including the wound bed under said covering; (c) selecting a sealing means competent enough to provide treatment of the wound with pressures purposefully altered from atmospheric, including higher and lower pressures; (d) providing a PAM for interfacing non-atmospheric pressures with the said Encapsulated Space, working in combination with said covering and sealing means to maintain the so desired Encapsulated Space pressures; said PAM comprising a Proximal end, a Medial section adapted to deliver negative pressures via venturi aspiration and a Distal end; (e) employing a reservoir means for holding a gas or liquid prior to flow through PAM; (f) employing a bulk collection means for collection of discharge from the PAM; (g) utilizing a pump for delivering the initial pressure differential to the PAM, (h) generating a venturi aspiration within the Encapsulated Space for negative pressure wound therapy; and (i) arranging the flow of non-wound liquids or gases, and the corresponding components, beginning at the reservoir, through Proximal end of the PAM, through the Medial section of the PAM within Encapsulated Space, through or by the pump and finally through the Distal end of the PAM into the bulk collection means.
11. The method of item 10 where the pump operates by a peristaltic means or a piston displacement means.
12. The method of item 10 further consisting of a Medial section venturi aspiration means with direct physical access to the Encapsulated Space through an opening or conduit through said covering.
13. The method of item 10 further consisting of a Medial section venturi aspiration means with direct physical access to the Encapsulated Space through a passage created between skin and sealing means of said covering.

14. The method of item 10 further consisting of a Medial section venturi aspiration means with indirect access to the Encapsulated Space though a void or opening in said cover.
15. The method of item 10 further consisting of a Proximal end with indirect access to the Encapsulated Space through a passage created between skin and sealing means of said covering.
16. The method of item 10 where the lines providing the venture aspiration also provide a means to alter wound bed temperature by regulation of the gas or liquid temperature providing the venturi aspiration.
17. The reservoir or collection means of item 10 composed of a means of controlling the liquid temperature within a specified a range, thereby providing a means to alter temperatures within the Encapsulated Space.
18. The method of item 10 where the reservoir and collection means are connected by a conduit thereby adapting the reservoir for recirculation.
19. The method of item 10 where any liquid contained in the reservoir contains an anti-infective agent selected from the group of antibacterial, antiviral, antifungal or any combination thereof.

IX. Wound Product Collection

Figure 30:
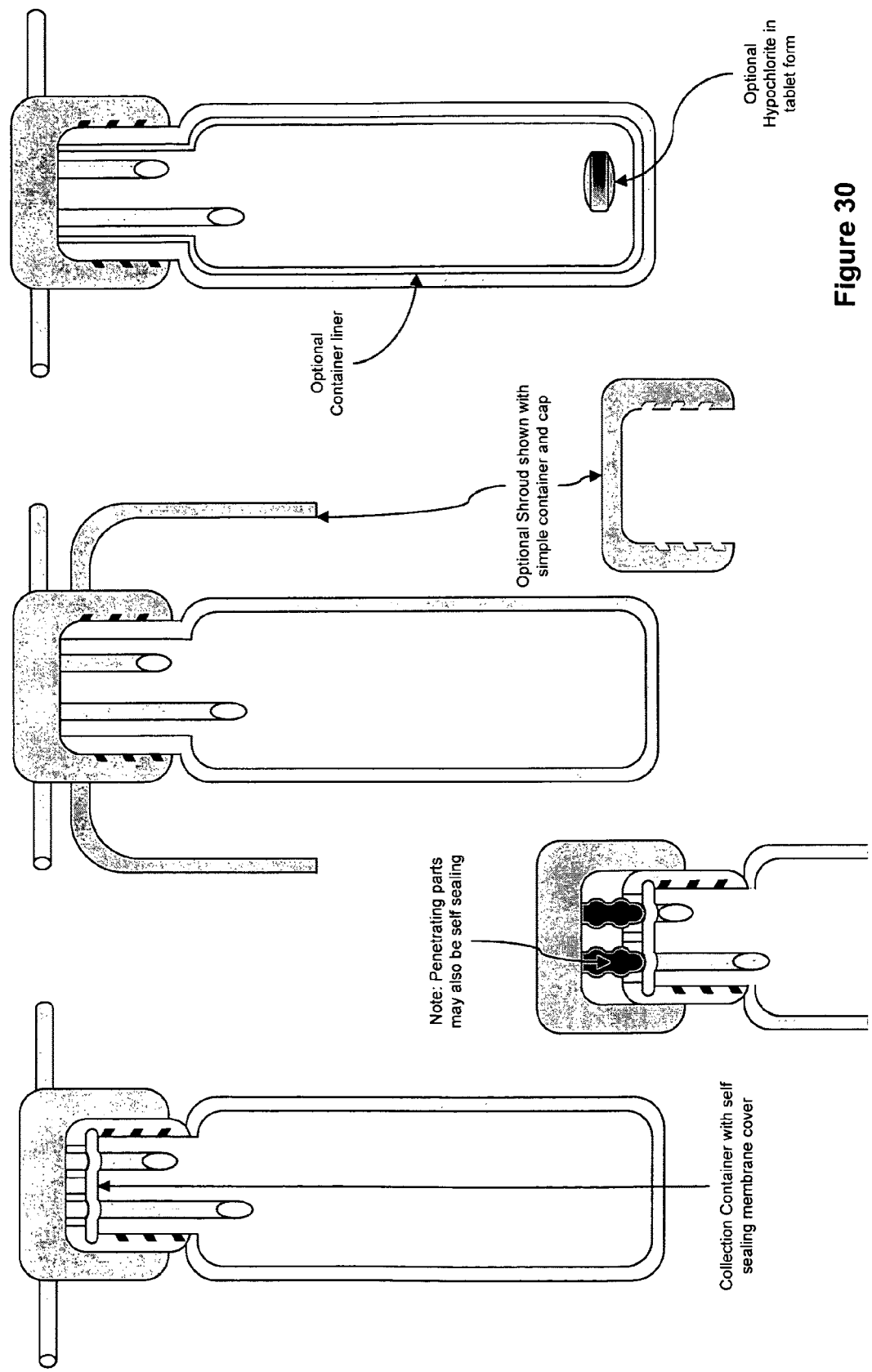
FIG. 30 shows a cross-sectional view of various bulk collection designs. The drawings further show design options including self sealing perforation membranes, shrouds, liners and pathogen/odor retardants.
Figure 31:
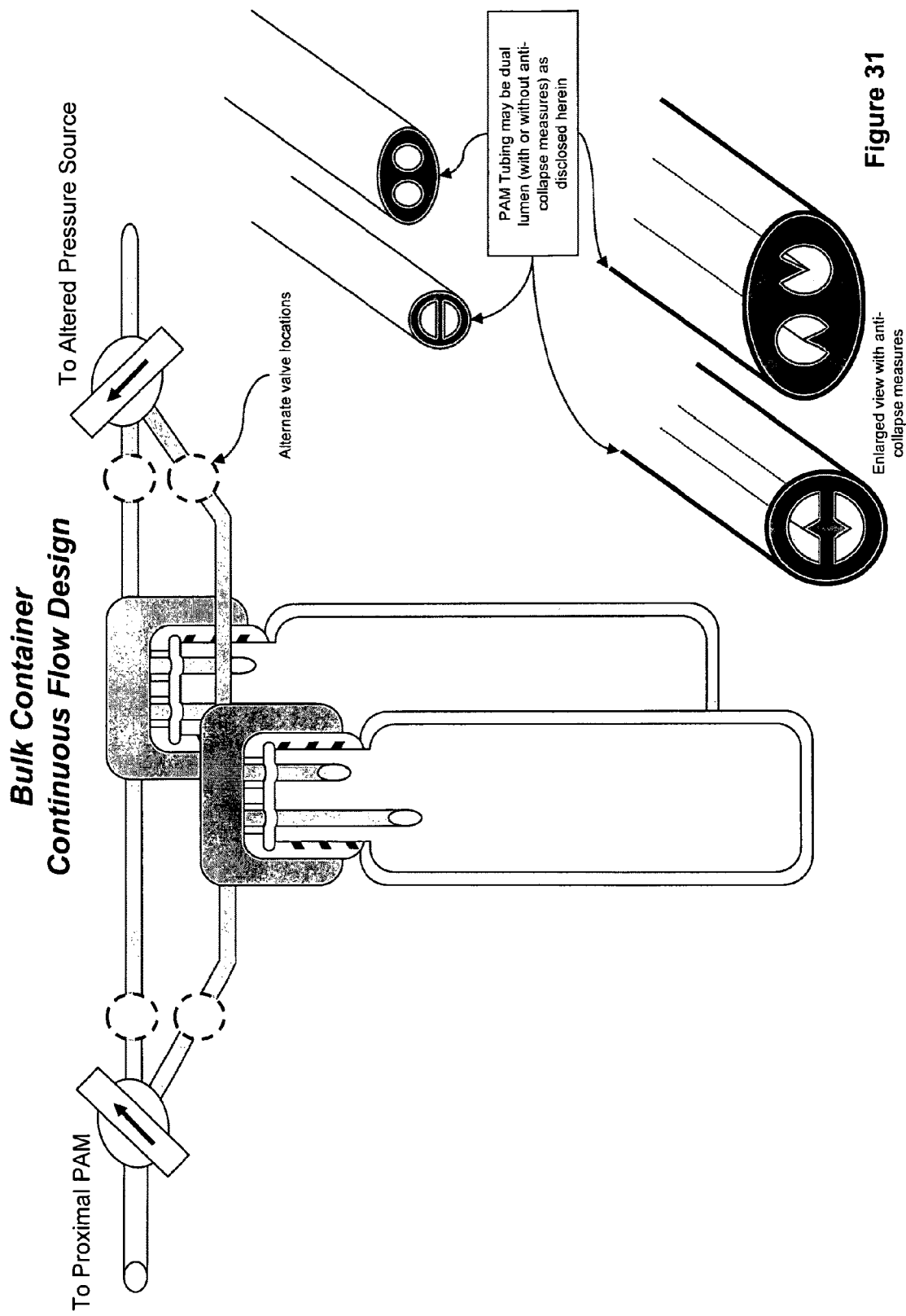
FIG. 31 shows a continuous flow configuration including by-pass valves and two bulk containers. The drawings further show enlarged views of various tubing/conduit designs including views of anti-collapse measures as disclosed herein.

Referring to FIGS. 30-31, preferred embodiments are disclosed. Broadly a bulk collection means is provided to increase patient comfort, clinician administration convenience and system efficacy. The collection means adapted for emptying the collected products without altering the pressures in the Encapsulated Space and without interrupting continuous collection of wound products into a collection means.

The best mode of the invention involves the utilization of two collection containers located downstream from a split junction and upstream from a union junction where the wound products are directed to either container by a single valve or two valves in opposition. The top covering means incorporates a means to attach the container to support structure of the bulk collection means while the collection container or liner contains a means to control bacteria growth and odor, such as hypochlorite. A second best mode provides a top covering means adapted for penetration by at least a portion of the PAM.

One method of the invention may be operated by alternating the valve or valves to by-pass one container. This configuration allows one container to be isolated from the Altered Pressure for disposal, exchange or clean out at any time without interruption of therapy. A second method may be operated by providing the container closures with a re-sealable membrane that may be pierced by parts in connection with or part of the PAM. This method further limits the potential of clinician contact with bodily fluids.

The embodiments are further described by the following aspects:

1. An Altered Pressure Apparatus where the Medial or Distal segment of the PAM is comprised of a bulk collection means comprising at least one container for the storage of wound products including those optionally selected from the group of fluid exudates, bacteria, wound debris, administered Therapeutics and combinations thereof.
2. The bulk collection means of item 1 where the collection means is adapted for emptying the collected products without altering the pressures in the Encapsulated Space.
3. The bulk collection means of item 1 where the collection means is adapted for emptying the collected products without interrupting continuous collection of wound products into a collection means.
4. The bulk collection means of items 2-3 where multiple collection containers are downstream from a split junction.
5. The bulk collection means of items 2-3 where the multiple collection containers are upstream from a union junction.
6. The bulk collection means of items 4-5 where multiple valves are employed.
7. The bulk collection means of items 4-5 where a single valve that operates multiple paths is employed.
8. The bulk collection means of items 1-7 are comprised of a top covering means adapted for penetration by at least one other portion of the PAM.
9. The bulk collection means of item 8 where the top covering means is composed of a soft cover adapted for relatively easy perforation and penetration by the PAM.
10. The bulk collection means of item 8 where the top covering means is composed of soft cover adapted to be at least partially self sealing.
11. The bulk collection means of item 8 where the top covering means is composed of a means to secure the covering to the container.
12. The bulk collection means of item 8 where the top covering means is composed of a means to attach the container to support structure of the bulk collection means.
13. The bulk collection means of items 1-12 where the collection containers are disposable.
14. The bulk collection means of items 1-13 where the collection containers adapted for secure closure.
15. The bulk collection means of items 1-14 where the collection containers are marked as bio-hazardous.
16. The bulk collection means of items 1-15 where the collection containers are marked with a quantitative scale.
17. The bulk collection means of items 1-16 where the collection containers are fitted with disposable liners.
18. The bulk collection means of items 1-17 where the collection containers are positioned over a disposable spillage catch.
19. The bulk collection means of items 1-18 where the PAM connection to the collection containers is provided with a protective shroud to protect healthcare workers from inadvertent contact with collected products.
20. The bulk collection means of items 1-19 where the shroud to protect healthcare workers is disposable.
21. The bulk collection means of items 1-20 where the downstream PAM is fitted with a filtering system.
22. The bulk collection means of items 1-21 where the collection container or liner contains a carbohydrate, a salt, a lipid or any combination thereof to control bacteria growth and odor.
23. The bulk collection means of item 22 where the carbohydrate is a sugar.
24. The bulk collection means of item 22 where the salt is an inorganic salt.
25. The bulk collection means of item 22 where the salt is an organic salt.
26. The bulk collection means of item 22 where the lipid is a fatty acid.
27. The bulk collection means of item 22 where the collection container or liner contains a hypochlorite derivative to control bacteria growth and odor.

28. A method of collecting wound products while employing an Altered Pressure Apparatus comprising providing a bulk collection means in the Medial or Distal segment of a PAM, BCM comprising at least one container for the temporary storage of wound products.
29. The method of item 28 where the collection means is adapted for emptying the collected products without altering the pressures in the Encapsulated Space.
30. The method of item 28 where the collection means is adapted for emptying the collected products without interrupting continuous collection of wound products into the collection means.
31. The method of items 28-30 where multiple collection containers are downstream from a split junction.
32. The method of items 28-30 where the multiple collection containers are upstream from a union junction.
33. The method of items 28-30 where multiple valves are employed.
34. The method of items 28-30 where a single valve that operates multiple paths is employed.
35. The method of items 28-34 where the PAM connection to the collection containers is provided with a protective shroud to protect healthcare workers from inadvertent contact with collected products.
36. The method of items 28-35 where the collection container or liner contains a hypochlorite derivative to control bacteria growth and odor.

X. Temporary Shutoff Means

Broadly a preferred system is disclosed to increase patient comfort, clinician convenience and system efficacy. The system comprises a shut off means for temporarily sealing the pressure altering means between the Distal and Proximal ends providing short term maintenance of critical pressure while disconnecting or shutting off the Altered Pressure source.

The best mode of the invention involves supplying a pressure closure, valve closure or self-sealing pierced membrane for the temporary maintenance of internal pressures. In second best mode, a means of disconnection of between the shut off means and the Altered Pressure source is also provided.

One method of the invention may be operated by activating the shut off means, then disconnecting a segment of the PAM between the shutoff means and pressure altering source allowing the patient to be moved or transferred a short distance prior to re-connection.

The embodiments are further described by the following aspects:

1. An Altered Pressure Apparatus which comprises a shut off means for temporarily sealing the PAM between the Distal and Proximal ends, providing minimum pressure change while changing drainage collection container or moving patient.
2. The Altered Pressure Apparatus of item 1 where the shut off means is selected from a group including a clip, valve, self sealing pierced membrane, pinch closure, wedge closure or any combination thereof.
3. The Altered Pressure Apparatus of item 1 comprising a means of disconnection of between the shut off means and the Altered Pressure source thereby liberating patient temporarily for free movement or transportation.
4. A method of easing mobility, drainage disposal or transfer of patients under wound treatment with an Altered Pressure Apparatus comprising: providing a shut off means for temporarily sealing the PAM between the Distal and Proximal ends, providing minimum pressure change while changing drainage collection or moving patient.
5. The method of item 4 where the shut off means is selected from a group including a clip, valve, self sealing pierced membrane, pinch closure, wedge closure or any combination thereof.
6. The method of item 4 further comprising installing a means of disconnection of between the shut off means and the Altered Pressure source thereby liberating patient temporarily for free movement or transportation.

XI. Cushioning Means

Figure 32:
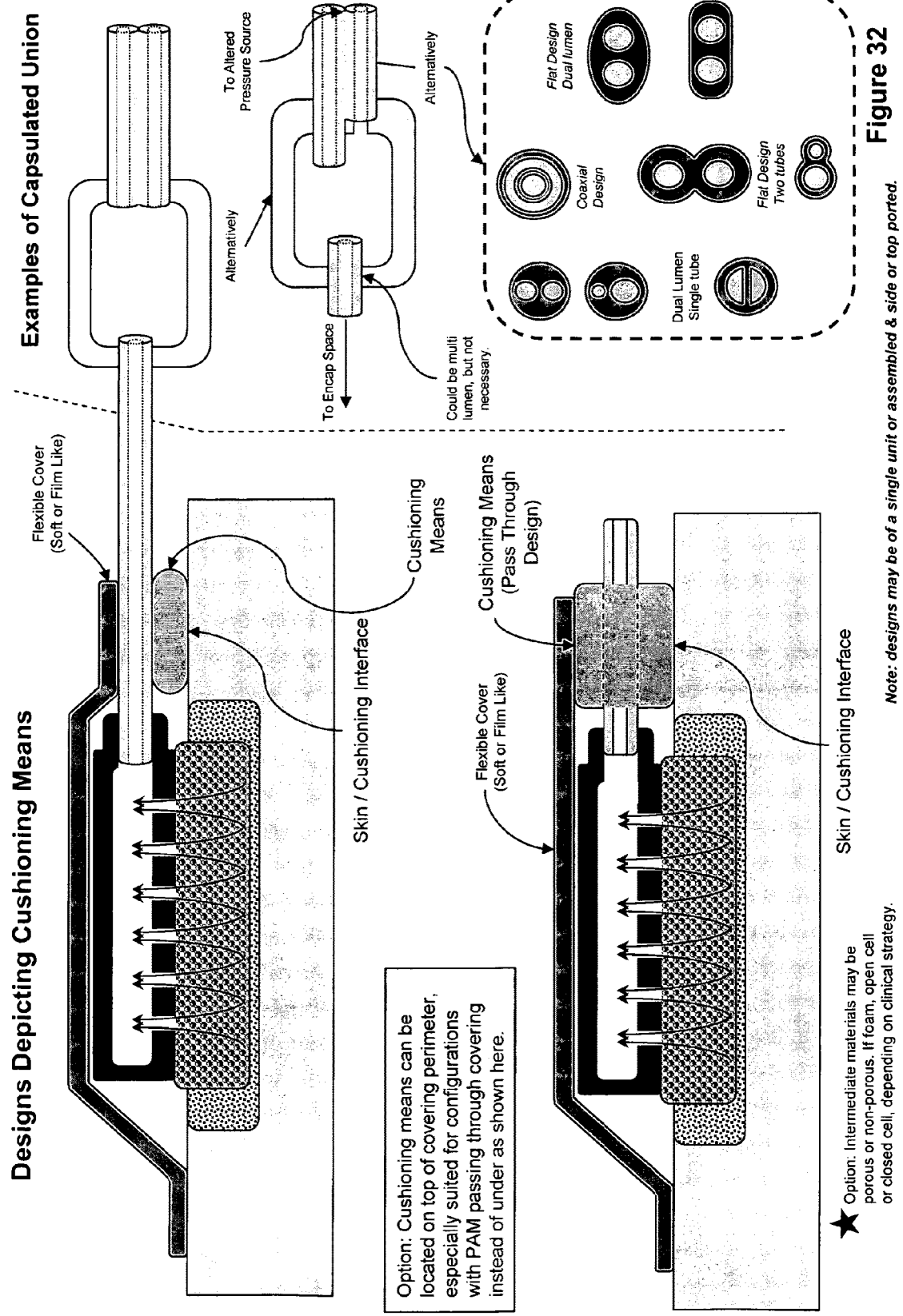
FIG. 32 shows a cross-sectional view of various designs depicting a cushioning means. The drawings further show design options including a through cushion option. The drawings further illustrate a PAM design that include an optional capsulated union for pressure sensing between the Encapsulated Space and the bulk collection means including various tubing options to accommodate the design.

Referring to FIG. 32, a preferred embodiment is disclosed. A cushioning means is provided to increase patient comfort and system efficacy. The cushioning means may be located between the pressure altering means and the skin, specifically the peripheral skin surrounding the wound.

The best mode of the invention involves placement of the cushioning means within 0.1 cm to 10 cm of the beginning margin of the wound.

One method of the invention may be operated by placing a hydrogel or hydrocolloid dressing on the peripheral skin of the wound where the PAM will be applying physical pressure. Alternatively a closed-cell foam or silicone derivative may be utilized. Subsequently, the covering means and PAM are installed over the cushioning means.

The embodiments are further described by the following aspects:

1. An Altered Pressure Apparatus comprising a cushioning means between the PAM and the skin, specifically the peripheral skin surrounding the wound.
2. The cushioning means of item 1 where the peripheral skin surrounding the wound includes skin up to 7.5 cm from the beginning margin of the wound.
3. The cushioning means of item 1 where the cushioning means is at located at least partially under the covering means.
4. The cushioning means of item 1 where the cushioning means is comprised of compositions selected from the group of silicone derivatives, latex rubber derivatives, soft synthetic polymers, closed cell foams or any combination thereof.
5. The cushioning means of item 1 where the cushioning means is comprised of compositions selected from the group of hydrogels, hydrocolloids or any combination thereof.
6. A method of providing comfort, inhibiting trauma and reducing pain for patients under wound treatment with an Altered Pressure Apparatus comprising: positioning a cushioning means between the PAM and the skin, specifically the peripheral skin surrounding the wound.
7. The method of item 6 where the cushioning means is comprised of compositions selected from the group of silicone derivatives, latex rubber derivatives, soft synthetic polymers, closed cell foams or any combination thereof.
8. The method of item 6 where the cushioning means is comprised of compositions selected from the group of hydrogels, hydrocolloids or any combination thereof.

XII. Cover Opening Support

Referring to FIGS. 14, 20-25 and 34, preferred embodiments are disclosed. Broadly a supporting means is provided to reinforce the perimeter of any opening in said cover, in increase clinician convenience and system efficacy.

The best mode of the invention involves involve the utilization of a washer, or reinforcing laminate, adapted to be non-rigid and adapted to accommodate one or more release liners to aid handling. A second best mode of the invention directs the washer to be comprised of multiple layers to assist manufacturing, which may be held in place by adhesive, the washer further containing adhesive at least the side opposite the covering.

One method of the invention may be operated by the application of the supporting means to the covering, both comprising releasing means on opposite sides, then perforating the supporting means in the center, thereby producing a washer shape. Next, removing the releasing means of the washer and applying the PAM. Lastly, removing the releasing means from said covering and applying to patient.

Another method of the invention may be operated by first, applying the cover to the patient and making an opening through the cover; second, removing a Top releasing means of the supporting means and applying to the PAM; third, removing a bottom releasing means of the supporting means and applying the PAM and supporting means over the opening in the cover.

The embodiments are further described by the following aspects:
1. The apparatus disclosed herein where the terminating PAM accesses the Encapsulated Space through the covering and further comprises a reinforcing support washer for fixation to the periphery of the opening.
2. The washer of item 1 adapted to be non-rigid including polymeric films, silicone derivatives, soft plastics and foams.
3. The washer of item 1 composed of multiple layers to assist manufacturing.
4. The washer of item 4 composed of multiple layers held in place by adhesive.
5. The washer of item 1 composed of adhesive on at least the side opposite the covering.
6. The washer of item 5, further providing a means for rapid adherence and fixation of a PAM to the Top of the cover directly over an opening through said cover.
7. The washer of item 1-6 adapted to be installed during dressing changes as an independent article or preinstall by manufacturer.
8. The washer of items 1-7 adapted to accommodate a one or more release liners to aid handling, production and application.
9. A method of providing a means for rapid application of a dressing intended for use with an Altered Pressure Apparatus for wound therapy comprising the use of a washer for fixation to, and/or reinforcing support of, the periphery of an opening through the cover.
10. The method of item 9 where the washer comprises adhesive on at least the side opposite the covering.
11. The method of item 10 wherein the washer further provides a means for rapid adherence of a terminating PAM to the Top of the cover directly over an opening through said cover.
12. The method of item 9 where the washer is comprised of at least a partially flexible material including polymeric films, silicone derivatives, soft plastics and foams.
13. The method of item 9 manufacturing is assisted by fabricating the washer from multiple layers into an ultimate laminate responsible for the total strength.
14. The method of item 13 where the multiple layers held in place by adhesive.
15. The method of items 9-14 adapted to accommodate a one or more release liners to aid handling, production and application.

XIII. Encapsulated Pressures

Broadly Altered Pressure methods are disclosed. These methods comprise altering the pressure in the Encapsulated Space from atmospheric by a specified amount for a specified duration, thereby creating a single cycle of therapy.

The best mode for positive pressures of the invention involves maintaining the Encapsulated Space pressure between 1 mm and 140 mm of Hg greater than atmospheric. The best mode for negative pressures of the invention involves maintaining the Encapsulated Space pressure between 1 mm and 140 mm Hg less than atmospheric.

One method of the invention may be operated by a cycle of 4 hours at 117 mm Hg below atmospheric and 15 minutes at 10 mm Hg above atmospheric. A second method of the invention may be operated by a cycle of 12 hours at 117 mm Hg below atmospheric and 10 minutes at 10 mm Hg above atmospheric. A third method of the invention may be operated by a cycle of 24 hours at 117 mm Hg below atmospheric and 5 minutes at 10 mm Hg above atmospheric. A fourth method of the invention may be operated by a cycle of 48 hours at 117 mm Hg below atmospheric.

The embodiments are further described by the following aspects:
1. An Altered Pressure Apparatus where the pressure inside the Encapsulated Space is altered from atmospheric by a specified amount for a specified duration, thereby creating a single cycle of therapy.
2. The Altered Pressure Apparatus of item 1 the Altered Pressure is greater than atmospheric.
3. The Altered Pressure Apparatus of item 2 where a cycle is composed of a specified pressure greater than atmospheric selected from the group of between 1 and 440 mm Hg, between 1 and 240 mm Hg, between 1 and 140 mm Hg greater than atmospheric, between 1 and 76 mm Hg, between 1 and 57 mm Hg, between 1 and 40 mm Hg, between 1 and 20 mm Hg, between 1 and 10 mm Hg and any combination thereof.
4. The Altered Pressure Apparatus of item 1 the Altered Pressure is less than atmospheric.
5. The Altered Pressure Apparatus of item 4 where a cycle is composed of a specified pressure less than atmospheric selected from the group of between 175 and 200 mm Hg, between 155 and 160 mm Hg, between 130 and 150 mm Hg, between 115 and 119 mm Hg, between 45 and 55 mm Hg, between 10 and 30 mm Hg, between 11 and 29 mm Hg and any combination thereof.
6. The Altered Pressure Apparatus of items 1-5 where a cycle is composed of a specified duration selected from the group of between 0.1 and 168 hours, between 0.25 and 168 hours, between 0.1 and 120 hours, between 0.25 and 72 hours, between 0.75 and 48 hours, between 2 and 36 hours, between 4 and 18 hours, between 2 and 12 hours, and any combination thereof.
7. The Altered Pressure Apparatus of items 1-6 where one cycle, or a multiple of cycles, which is followed by a period of time where the encapsulated pressure is allowed to return to atmospheric conditions, is considered a batch.
8. The Altered Pressure Apparatus of item 7 where one batch or a multiple of batches that occur prior to a scheduled dressing change is considered a treatment regimen.
9. The Altered Pressure Apparatus of item 8 where one regimen, or a multiple of regimens, that occur as a total treatment, is considered a course of therapy, resulting in a return to atmospheric conditions.

10. The Altered Pressure Apparatus of items 7-9 where a batch contains pressures less than and greater than atmospheric.
11. A method of treating a wound with an Altered Pressure Apparatus comprising: altering the pressure in the Encapsulated Space from atmospheric by a specified amount for a specified duration, thereby creating a single cycle of therapy.
12. The method of item 11 where the pressure is altered to be greater than atmospheric.
13. The method of item 12 where the pressure is altered to be greater than atmospheric and selected from the group of between 1 and 440 mm Hg, between 1 and 240 mm Hg, between 1 and 140 mm Hg, between 1 and 76 mm Hg, between 1 and 57 mm Hg, between 1 and 40 mm Hg, between 1 and 20 mm Hg, between 1 and 10 mm Hg, and any combination thereof.
14. The method of item 11 where the pressure is altered to be less than atmospheric.
15. The method of item 14 where the pressure is altered to be less than atmospheric and selected from the group of between 175 and 200 mm Hg, between 155 and 160 mm Hg, between 130 and 150 mm Hg, between 115 and 119 mm Hg, between 45 and 55 mm Hg, between 10 and 30 mm Hg, between 11 and 29 mm Hg, and any combination thereof.
16. The method of items 11-15 where a cycle is composed of a specified duration selected from the group between 0.1 and 168 hours, between 0.25 and 168 hours, between 0.1 and 120 hours, between 0.25 and 72 hours, between 0.75 and 48 hours, between 2 and 36 hours, between 4 and 18 hours, between 2 and 12 hours, or any combination thereof.
17. The method of items 11-16 where one cycle, or a multiple of cycles, which is followed by a period of time where the encapsulated pressure is allowed to return to atmospheric conditions, is considered a batch.
18. The method of item 17 where one batch or a multiple of batches that occur prior to a scheduled dressing change is considered a treatment regimen.
19. The method of item 18 where one regimen, or a multiple of regimens, that occur as a total treatment, is considered a course of therapy, resulting in a return to atmospheric conditions.
20. The method of items 17-19 where a batch contains pressures less than and greater than atmospheric.

XIV. Pressure Sources

Figure 33:
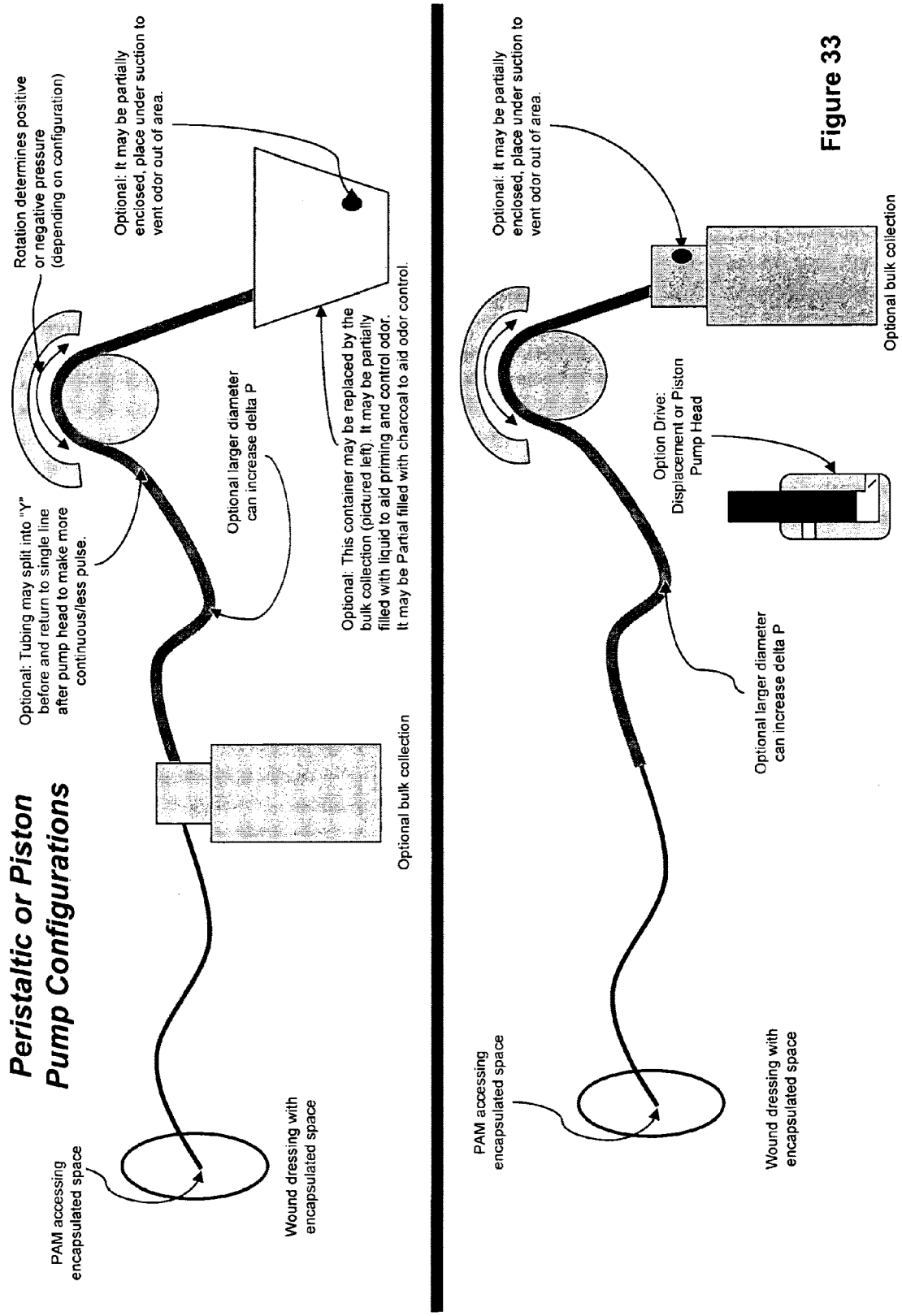
FIG. 33 shows a peristaltic and piston pump configuration to deliver Altered Pressure therapy. The drawings further show design options including a collection means for fluids.
Figure 38:
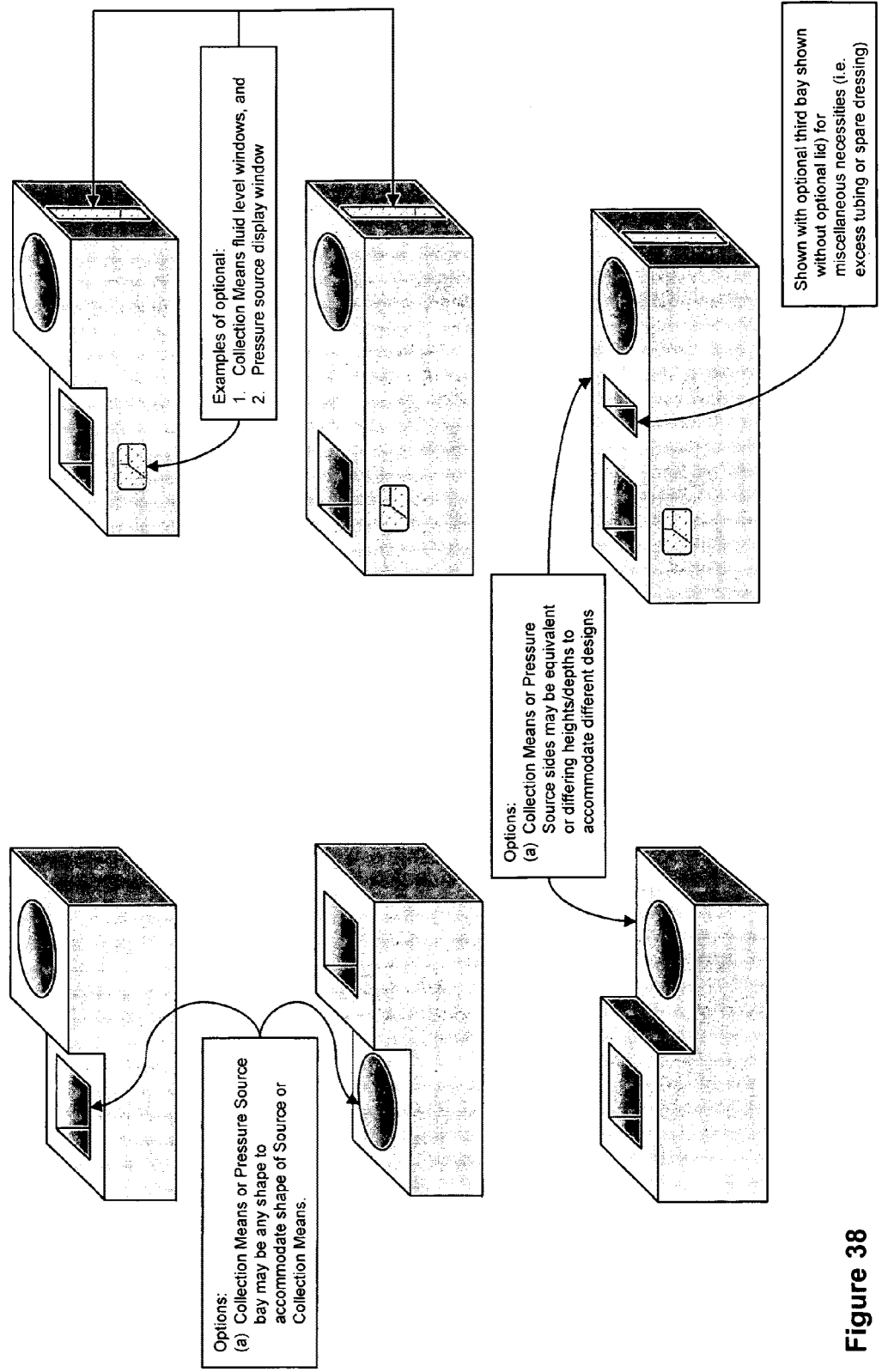
FIGS. 38-40 show various Cradle configurations for an Altered Pressure wound therapy system intended to aid transport, secure the system including biological fluids and reduce the weight of the pressure altering means.
Figure 39:
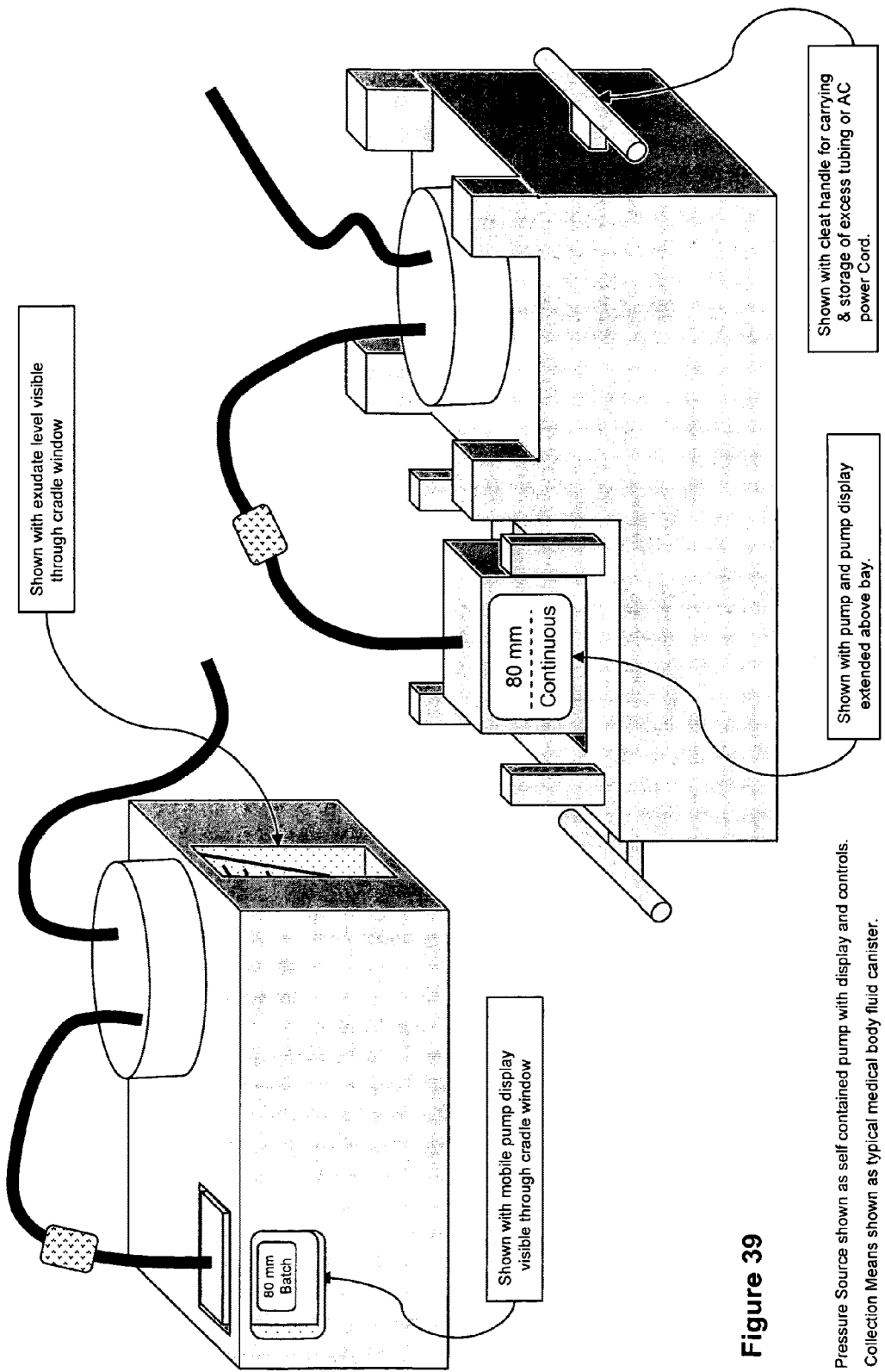
Figure 40:
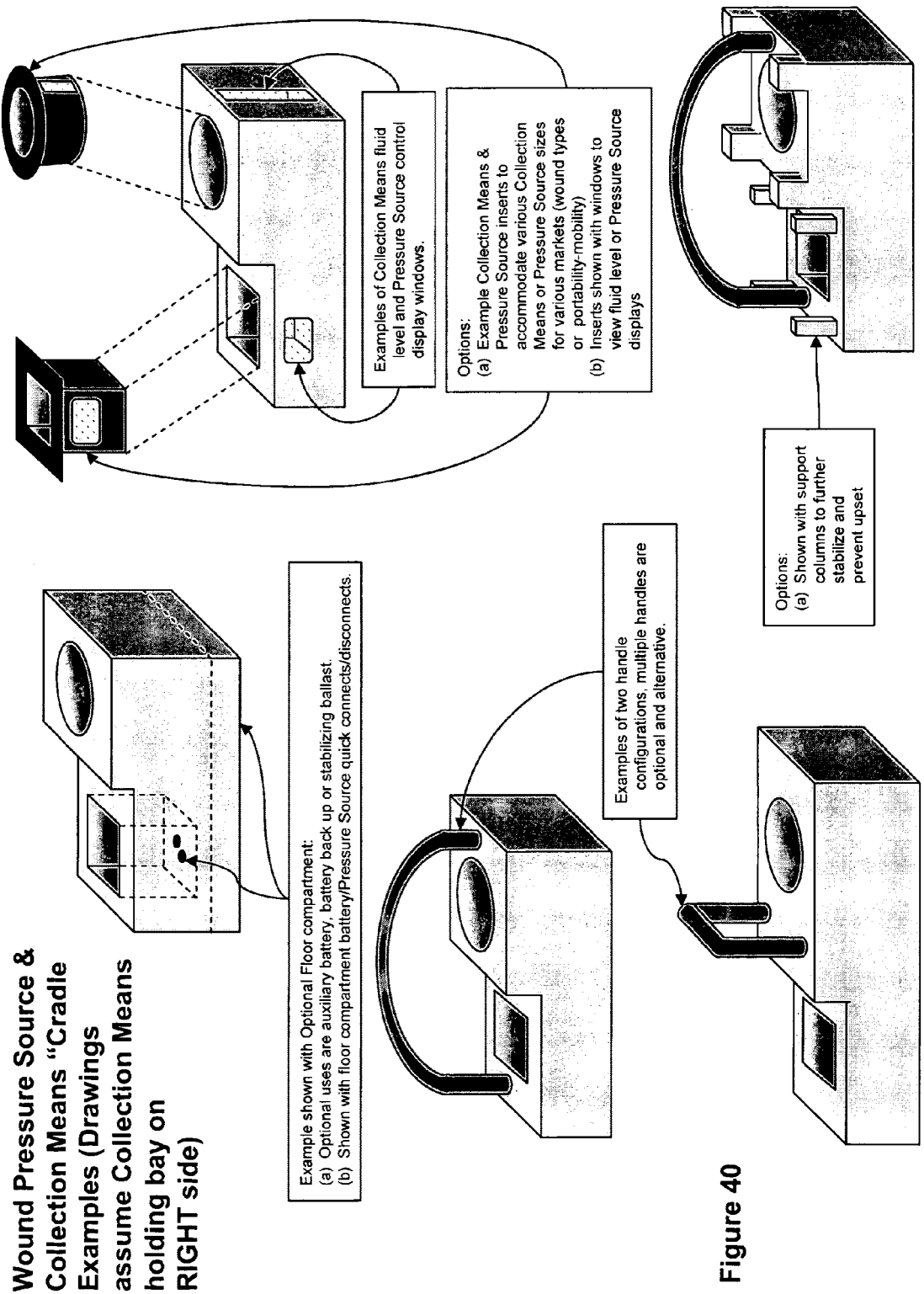

Referring to FIG. 33, preferred embodiments are disclosed. Broadly a positive displacement means for generating Altered Pressures is provided to increase clinician convenience.

The best mode of the invention involves the utilization of a peristaltic pump, preferably with a split tubing connection to minimize pulsing. A second best mode of the invention employs a piston style positive displacement, preferably as used for patient infusions to provide the drive for Altered Pressures.

One method of the invention may be operated by the application of peristaltic pumps on the same or larger diameter tubing connected to the PAM and delivering the Altered Pressure relative to the revolutions per minute of the pump head. A second method of the invention may be operated by the application of piston pumps on the same or larger diameter tubing connected to the PAM and delivering the Altered Pressure relative to the plunges per minute of the piston.

The embodiments are further described by the following aspects:
1. An Altered Pressure Apparatus where the Altered Pressure source is selected from the group of negative pressure generators, positive pressure generators, pressure regulators or any combination thereof.
2. The Altered Pressure Apparatus of item 1 where the Altered Pressure source is a peristaltic pump.
3. The Altered Pressure Apparatus of item 1 where the Altered Pressure source is a piston pump, including any displacement pumps used for IV infusion.
4. The Altered Pressure Apparatus of item 1 where the Altered Pressure source is a vacuum pump.
5. A method of treating a wound with an Altered Pressure Apparatus comprising: generating an Altered Pressure with a peristaltic pump or a piston pump, including any displacement pumps used for IV infusion.

XV. Anti-Granulation In-Growth

Broadly a preferred system is disclosed to increase patient comfort and system efficacy. The system comprises the utilization of Altered Pressure therapy to a wound in conjunction with an anti-granulation in-growth compound or composition.

The best mode of the invention involves the utility of an anti-in-growth material that is a lipid, preferably a fatty acid or fatty acid ester. In the second best mode, the anti-in-growth material is an irritant or tissue growth inhibitor.

One method of the invention may be operated by applying the lipid to the wound bed, moistening the dressing with saline and then applying on Top of lipid. Another method is to coat the dressing with the lipid prior to application to the wound bed.

The embodiments are further described by the following aspects:
1. An Altered Pressure Apparatus comprised of an Intermediate or Secondary Material coated or impregnated with an anti-granulation in-growth adhesion material.
2. The anti-granulation material of item 1 comprised of an enzyme.
3. The anti-granulation material of item 1 comprised of an irritant.
4. The anti-granulation material of item 1 comprised of a semi-solid.
5. The semi-solid of item 4 comprised at least partially of a lipid.
6. The lipid of item 5 composed of a fatty acid ester selected from the group of glyceryl monoarachidonate, glyceryl monolaurate, glyceryl monolinoleate, glyceryl monolinolenate, glyceryl monomyristate, glyceryl monopalmitoleate, glyceryl monooleate, and glyceryl monostearate; glyceryl monocaprate, glyceryl monocaprylate, glyceryl monococoate, glyceryl monocollagenate, glyceryl monoerucate, glyceryl monohydroxystearate, glyceryl monoisopalmitate, glyceryl monolinoleate, glyceryl monolinolenate, glyceryl monomyristate, glyceryl monopalmitate, glyceryl monopentadecanoate, glyceryl monopolyacrylate, glyceryl monotallowate, glyceryl monocthiopropionate, glyceryl monocundecylenate, isopropyl monoarachidonate, isopropyl monolaurate, isopropyl monolinoleate, isopropyl monolinolenate, isopropyl monomyristate, isopropyl monopalmitoleate, isopropyl monooleate, and isopropyl monostearate; methyl monoarachidonate, methyl monolaurate, methyl monolinoleate, methyl monolinolenate, methyl monomyristate, methyl monopalmitoleate, methyl monooleate, and methyl monostearate, propylene glycyl monoarachidonate, propylene glycyl monolaurate, propylene glycyl monolinoleate, propylene glycyl monolinolenate, propylene glycyl monomyristate, propylene glycyl monopalmitoleate, propylene glycyl monooleate, propylene glycyl monostearate, or combinations thereof and preferably glycerol monooleate or glycerol monoerucate if cost effective, highly viscous Liquid Crystalline states are ultimately desired.

7. The lipid of items 5-6 composed at least partially of a fatty acid including caprylic acid, capric acid, lauric acid, myristic acid, myristoleic acid, palmitic acid, palmitoleic acid, oleic acid, or combinations thereof.

8. An Altered Pressure wound therapy method of controlling granulation tissue in-growth into an Intermediate or Secondary Material and subsequent adhesion comprising: coating or impregnating an Intermediate or Secondary Material with a tissue irritant to inhibit in-growth and tissue adhesions.

9. An Altered Pressure wound therapy method of controlling granulation tissue in-growth into an Intermediate or Secondary Material and adhesion comprising: coating or impregnating an Intermediate or Secondary Material with a semisolid to inhibit tissue in-growth and tissue adhesions.

10. The method of item 9 where the semi-solid any of items 5-7.

XVI. Rigid Covering Means for Shallow Wounds

Referring to FIG. 34, broadly a preferred system is disclosed to make Altered Pressure wound therapy practical for shallow wounds that do not require packing or significant void filling.

The best mode of the invention involves the utility of a semi rigid covering means that will resist collapse under negative pressure. A second mode requires the addition of a headspace manifold in the crown of the blister.

One method of the invention may be operated by applying the semi-rigid blister over a shallow wound, with a foam Intermediate at least partially filling the Encapsulated Space created by the blister cover. Another method is employ a headspace manifold in the Top of the blister to aid the distribution of negative pressures as well as the wicking of wound exudate from the foam.

The embodiments are further described by the following aspects:

1. An Altered Pressure Apparatus comprising: (a) a bulk collection means comprising at least one container for the temporary storage of wound products including those optionally selected from the group of fluid exudates, bacteria, wound debris, administered Therapeutics and combinations thereof; and (b) a covering means adapted to resist loss of its shape and seal under Altered Pressures.

2. The covering means of item 1 further comprising a foam core.

3. The covering means of item 1 further comprising a headspace chamber.

4. The covering means of item 3 where the Encapsulated Space is connected to the headspace chamber by way a manifold, created by multiple openings communicating the Encapsulated Space with the headspace chamber.

5. A method of treating a shallow wound with an Altered Pressure Apparatus comprising: (a) providing a bulk collection means comprising at least one container for the temporary storage of wound products including those optionally selected from the group of fluid exudates, bacteria, wound debris, administered Therapeutics and combinations thereof; and (b) utilizing a covering means adapted to resist loss of its shape and seal under Altered Pressures.

6. The covering means of item 5 further comprising a foam core.

7. The covering means of item 5 further comprising a headspace chamber.

8. The covering means of item 7 where the Encapsulated Space is connected to the headspace chamber by way a manifold, created by multiple openings communicating the Encapsulated Space with the headspace chamber.

XVII. Intermediate Materials for Use in Altered Pressure Therapy

Referring to FIGS. 3-5, 20-26, 32 and 34-37, broadly preferred Intermediate Material configurations are disclosed to make Altered Pressure wound therapy more comfortable with improved performance.

A best mode of the invention involves the utility of porous Intermediates for wounds when wicking of wound fluids is preferable.

A second best mode of the invention involves the utility of non-porous Intermediates for wounds when directing exudate flow to the outside margins of a foreign material is preferable.

A third best mode of the invention utilizes foam Rope as the Intermediate Material as referenced in FIGS. 35-37. In an open cell configuration the foams provide superior wicking. In a closed cell configuration, the foams provide superior exudate velocity and turnover at the tissue surface.

A fourth best mode of the invention employs biodegradable Intermediate Materials including proteinaceous matrix materials and lipids which augment wound healing.

One method of the invention may be operated by utilizing a porous matrix to drive capillary action toward the PAM. Another method of the invention may be operated by utilize non-porous materials to drive higher exudate velocities at the wound interface. Another method of the invention may be operated by supplying a foam Intermediate in a Rope or Raft configuration to aid packaging by vendors and administration by clinicians.

The embodiments are further described by the following aspects:

1. The Intermediate Material disclosed herein selected optionally from the group of perforated and non perforated non-porous materials including silicone derivatives, latex rubber, polytetrafluoro-ethylene (PTFE), silicone elastomers, polymer hydromers, synthetic polymers, hydrocolloids, closed-cell foams, proteinaceous foams, lipogels, porous materials sealed by a sealant including semisolids, or any combination thereof.

2. The Intermediate Material disclosed herein where Intermediate Material is a porous wicking matrix including woven materials, non-woven materials, open-cell foam, a synthetic sponge, a sterile sponge, a natural sponge, a fibrotic compact, a fibrotic nest, a proteinaceous sponge, or any combination thereof.

3. The Intermediate Material or PAM disclosed herein comprised at least partially of a biodegradable material optionally selected from the group of fatty acid esters, fatty acids, polyanhydrides, chitin derivatives, proteinaceous foams or any combination thereof.

4. The Intermediate Material disclosed herein where the Intermediate. Material is porous and composed individual openings averaging about 0.015 to 100 $mm^2$.

5. The Intermediate Material disclosed herein where the Intermediate Material is porous and composed individual openings averaging about 0.062 to 25 mm$^2$
6. The Intermediate Material disclosed herein where the Intermediate Material is porous and composed individual openings averaging about 0.25 to 16 mm$^2$.
7. The Intermediate Material disclosed herein impregnated or coated with at least one Therapeutic.
8. The Intermediate Material disclosed herein composed of, impregnated with, coated with or administered with a semi-solid.
9. The semi-solid of item 8 adapted to prevent or limit biofilm formation in the wound.
10. The semi-solid of item 9 composed of a fatty acid ester selected from the group of glyceryl monoarachidonate, glyceryl monolaurate, glyceryl monolinoleate, glyceryl monolinolenate, glyceryl monomyristate, glyceryl monopalmitoleate, glyceryl monooleate, and glyceryl monostearate; glyceryl monocaprate, glyceryl monocaprylate, glyceryl monococoate, glyceryl monocollagenate, glyceryl monoerucate, glyceryl monohydroxystearate, glyceryl monoisopalmitate, glyceryl monolinoleate, glyceryl monolinolenate, glyceryl monomyristate, glyceryl monopalmitate, glyceryl monopentadecanoate, glyceryl monopolyacrylate, glyceryl monotallowate, glyceryl monocthiopropionate, glyceryl monocundecylenate, isopropyl monoarachidonate, isopropyl monolaurate, isopropyl monolinoleate, isopropyl monolinolenate, isopropyl monomyristate, isopropyl monopalmitoleate, isopropyl monooleate, and isopropyl monostearate; methyl monoarachidonate, methyl monolaurate, methyl monolinoleate, methyl monolinolenate, methyl monomyristate, methyl monopalmitoleate, methyl monooleate, and methyl monostearate, propylene glycyl monoarachidonate, propylene glycyl monolaurate, propylene glycyl monolinoleate, propylene glycyl monolinolenate, propylene glycyl monomyristate, propylene glycyl monopalmitoleate, propylene glycyl monooleate, propylene glycyl monostearate, or combinations thereof and preferably glycerol monooleate or glycerol monoerucate if cost effective, highly viscous Liquid Crystalline states are ultimately desired.
11. The semi-solid of items 8-9 composed at least partially of a fatty acid including caprylic acid, capric acid, lauric acid, myristic acid, myristoleic acid, palmitic acid, palmitoleic acid, oleic acid, or combinations thereof.
12. An Intermediate or Secondary Material for use with Altered Pressure wound therapy comprising a Rope configuration, thereby adapting the material to accommodate a variety of wound shapes and sizes with minimal custom fitting.
13. The Intermediate or Secondary Material of item 12 comprised of foam including those composed of closed cells, open cells, porous, non-porous or any combination thereof.
14. The foam Rope of item 12 adapted for packaging as a coil.
15. The foam Rope of item 12 adapted for packaging in a Raft.
16. The Raft of item 15 where the individual Rope segments are created by perforations or discontinuous cuts in the stock foam.
17. The foam Rope of items 12-16 adapted to be easily cut or torn into segments of an appropriate length for wound packing.
18. A method of accommodating various wound sizes and shapes with minimum customization of the Intermediate or Secondary Materials used for Altered Pressure wound therapy comprising: adapting the Intermediate or Secondary Material into a Rope configuration to provide for packing the void space with less alterations of the material.
19. The method of item 18 comprising an Intermediate or Secondary Material of any of items 13-17.
20. The method of item 18 where the Rope is manufactured in coils, windings or stacks thereby readily adaptable to cheap packaging and shipment.
21. A method of augmenting the passage of fluids from the wound bed to the collecting means of the a PAM used for Altered Pressure wound therapy comprising: adapting the Intermediate or Secondary Material into a Rope configuration to provide more full thickness openings formed by the coils and turns of the Rope in the wound bed.
22. The method of item 21 comprising an Intermediate or Secondary Material of any of item 19.
23. An Altered Pressure Apparatus further comprising: (a) a bulk collection means comprising at least one container for the temporary storage of wound products including those optionally selected from the group of fluid exudates, bacteria, wound debris, administered Therapeutics and combinations thereof; and (b) a proteinaceous foam or sponge within the Encapsulated Space.
24. The apparatus of item 23 where the proteinaceous foam is made from proteins selected from the group of collagen, gelatin, lactoferrin, albumin, derivatives of this group, or any combination thereof.

XVIII. Pressure Sensing Feedback

Figure 4:
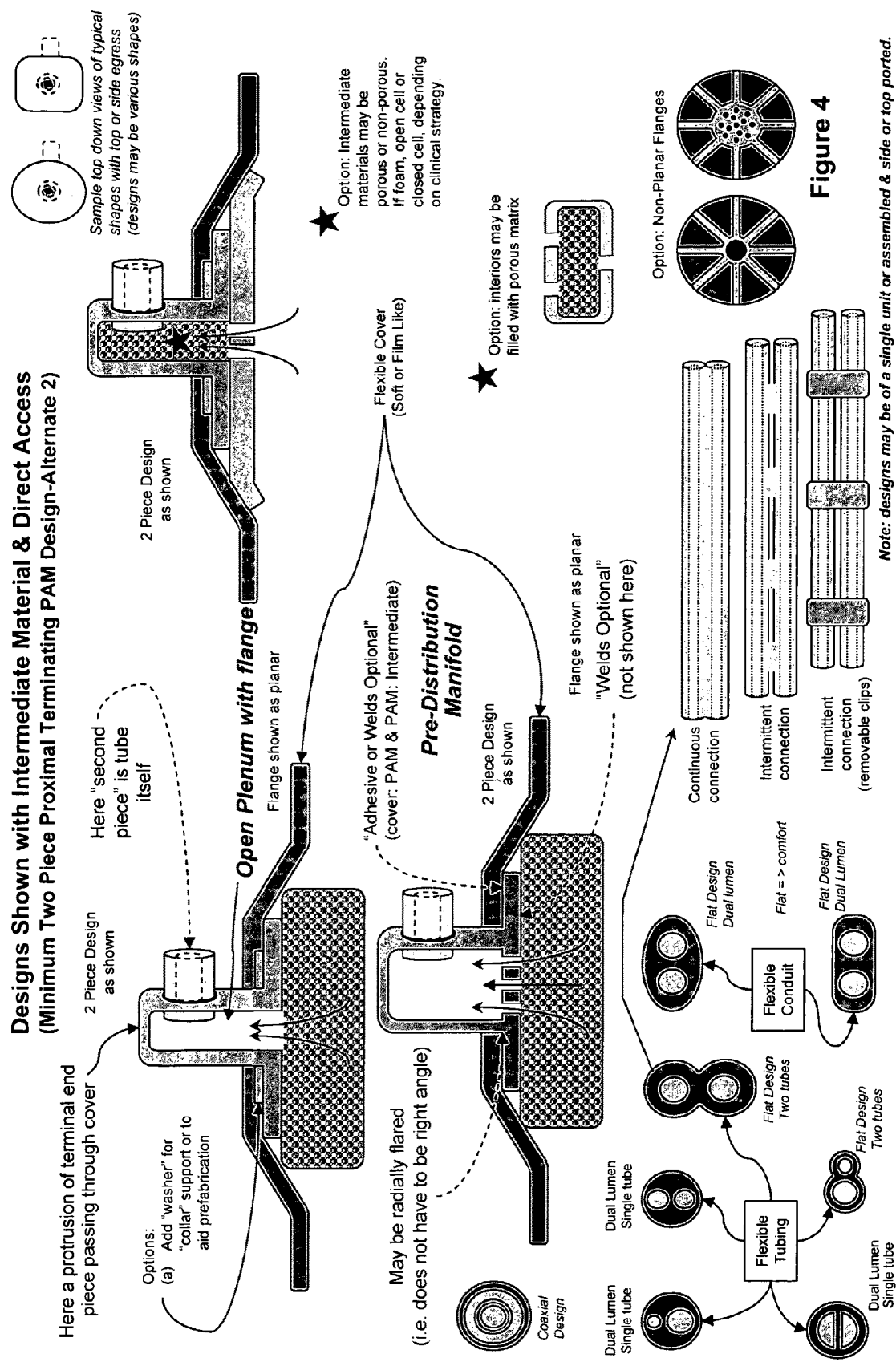
FIG. 4 shows a cross-sectional view of various minimum two piece Proximal end designs. The configurations in the figure depict two piece designs of internal flanges with manifolds or open Plenums which do not utilize male/female unions. The example configurations also employ an optional Intermediate Material. The drawings further show samples of Top down views of typical shapes and design options including examples of various opening patterns, porous matrix interiors, non-planar flanges, washers for support or fixation, and multiple passage tubing or conduit which can be utilized in lieu of simple tubing.
Figure 5:
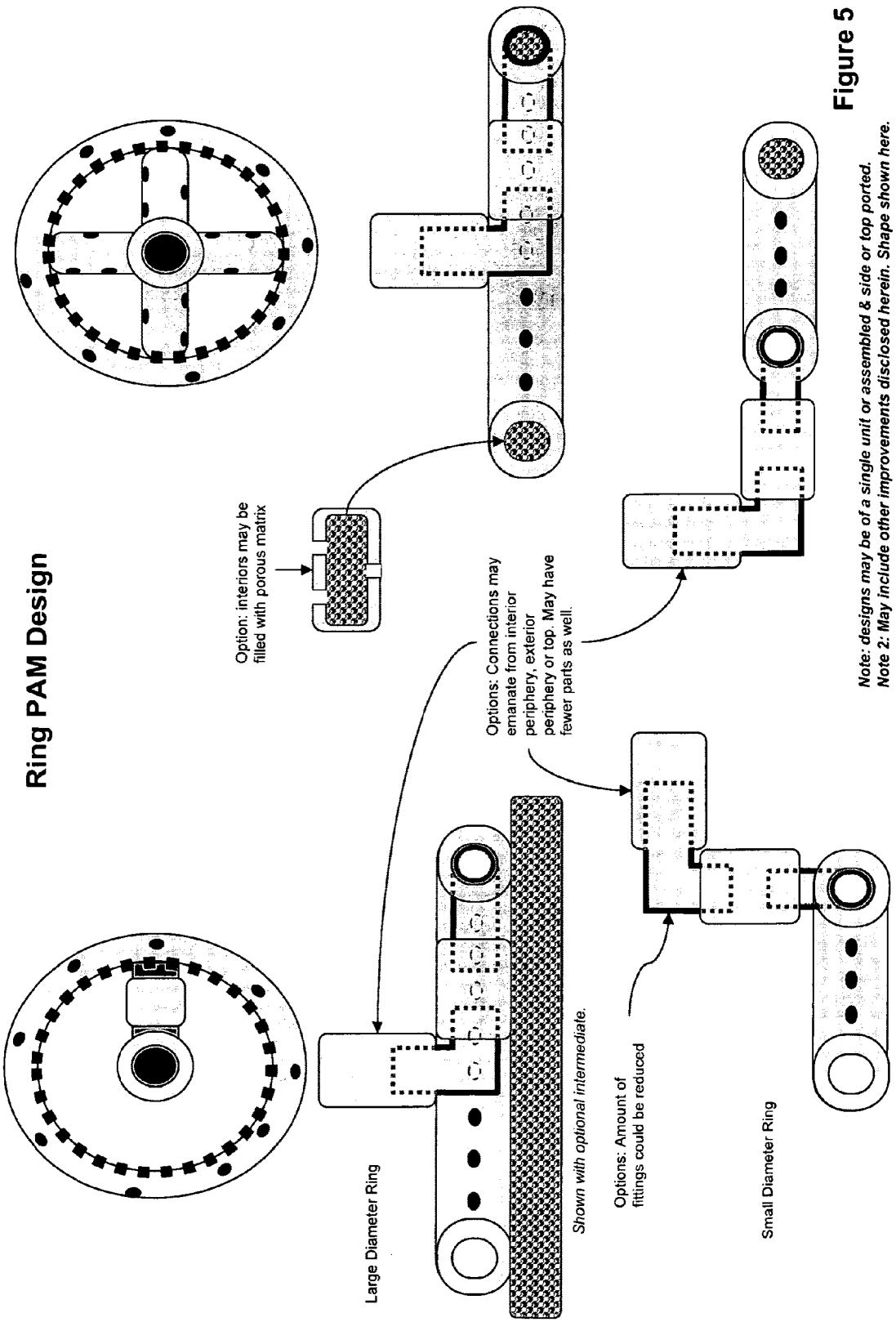
FIG. 5 shows a cross-sectional view of various PAM designs of ring configuration. The drawings further show design options including a porous matrix interior.
Figure 6:
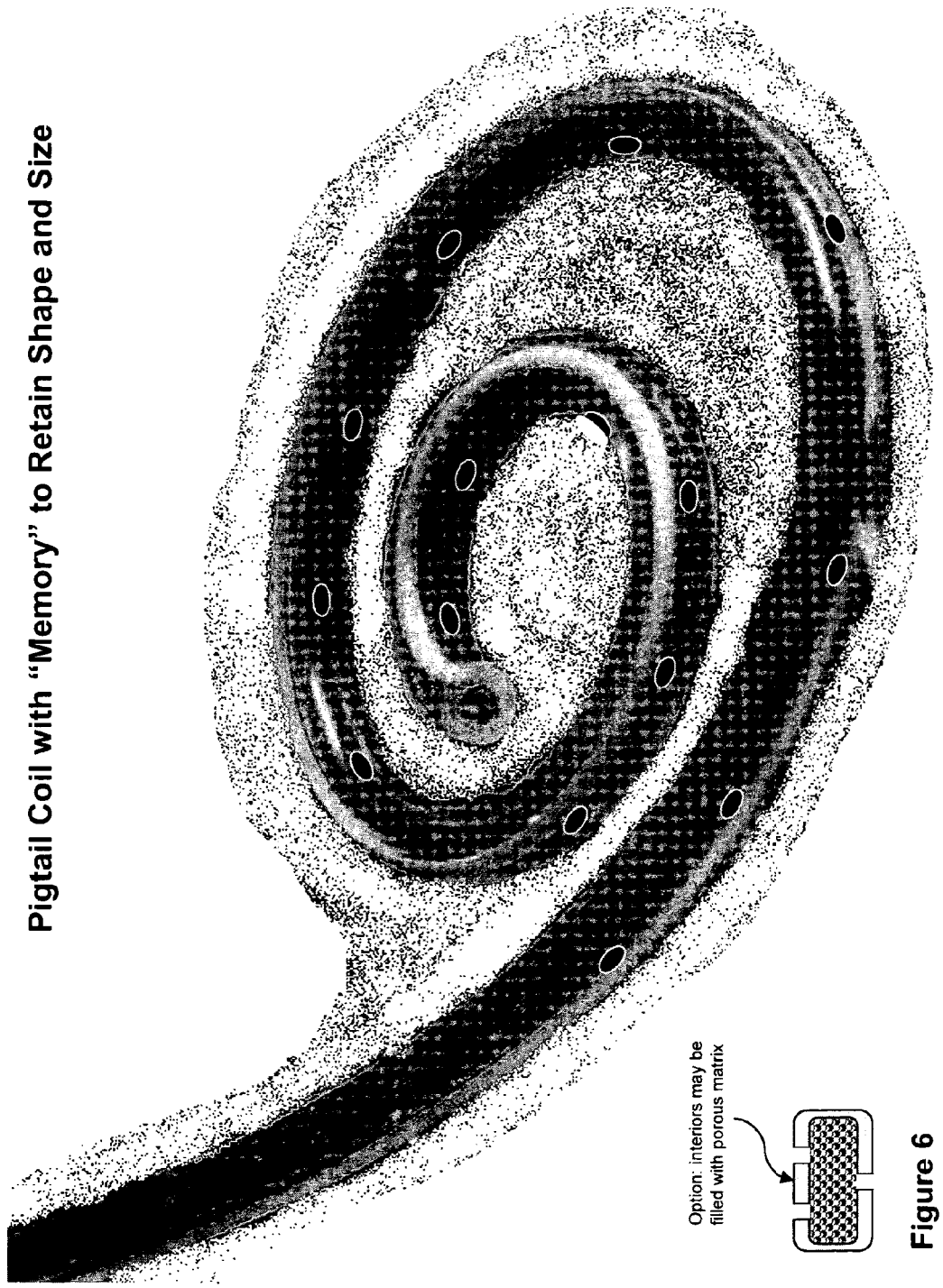
FIG. 6 shows a Top down view of a PAM design of coil configuration which has been adapted to have a memory for its coil. The drawings further show design options including a porous matrix interior.
Figure 7:
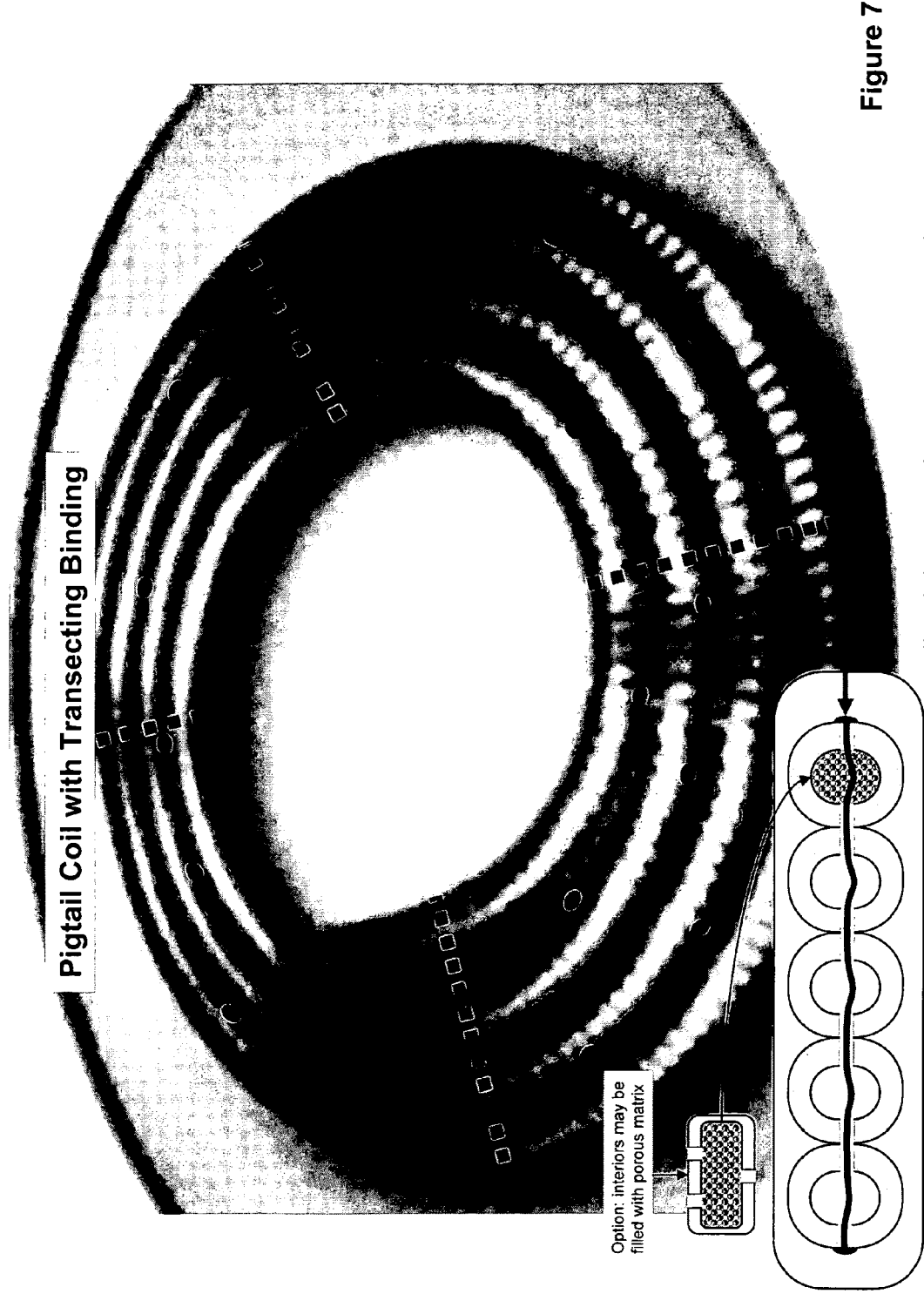
FIG. 7 shows a Top down view of a PAM design of coil configuration. The drawings further show design options including a porous matrix interior and a transecting binding or "tie" option.
Figure 8:
FIG. 8 shows a Top down view of a PAM design of coil configuration. The drawings further show design options including a porous matrix interior and a band option to maintain the coils.
Figure 9:
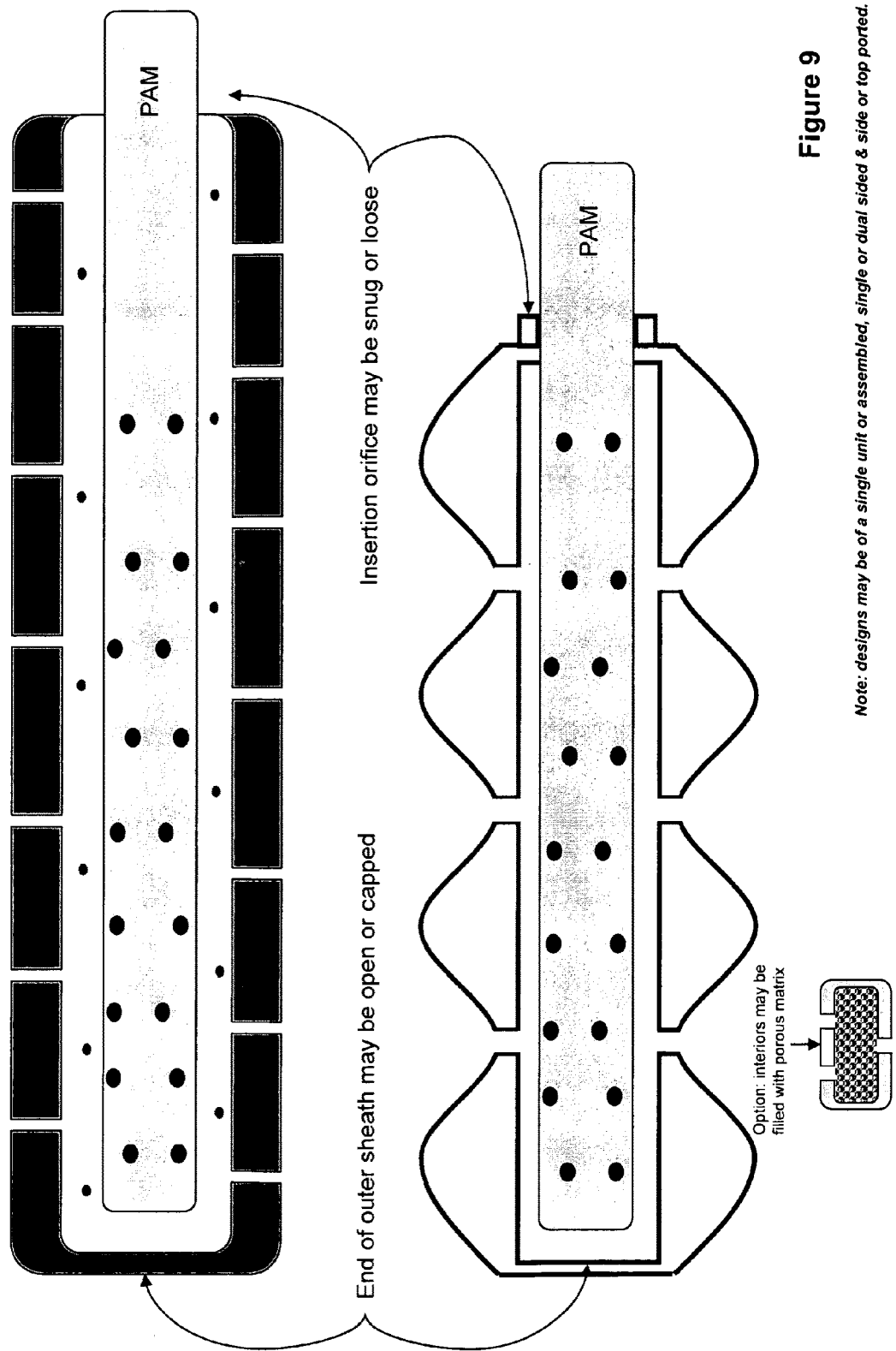
FIG. 9 shows a cross-sectional view of a coaxial or sheath designs which may be adapted for use with semisolids including gels. The drawings further show design options including a porous matrix interior and non-planar surfaces.
Figure 10:
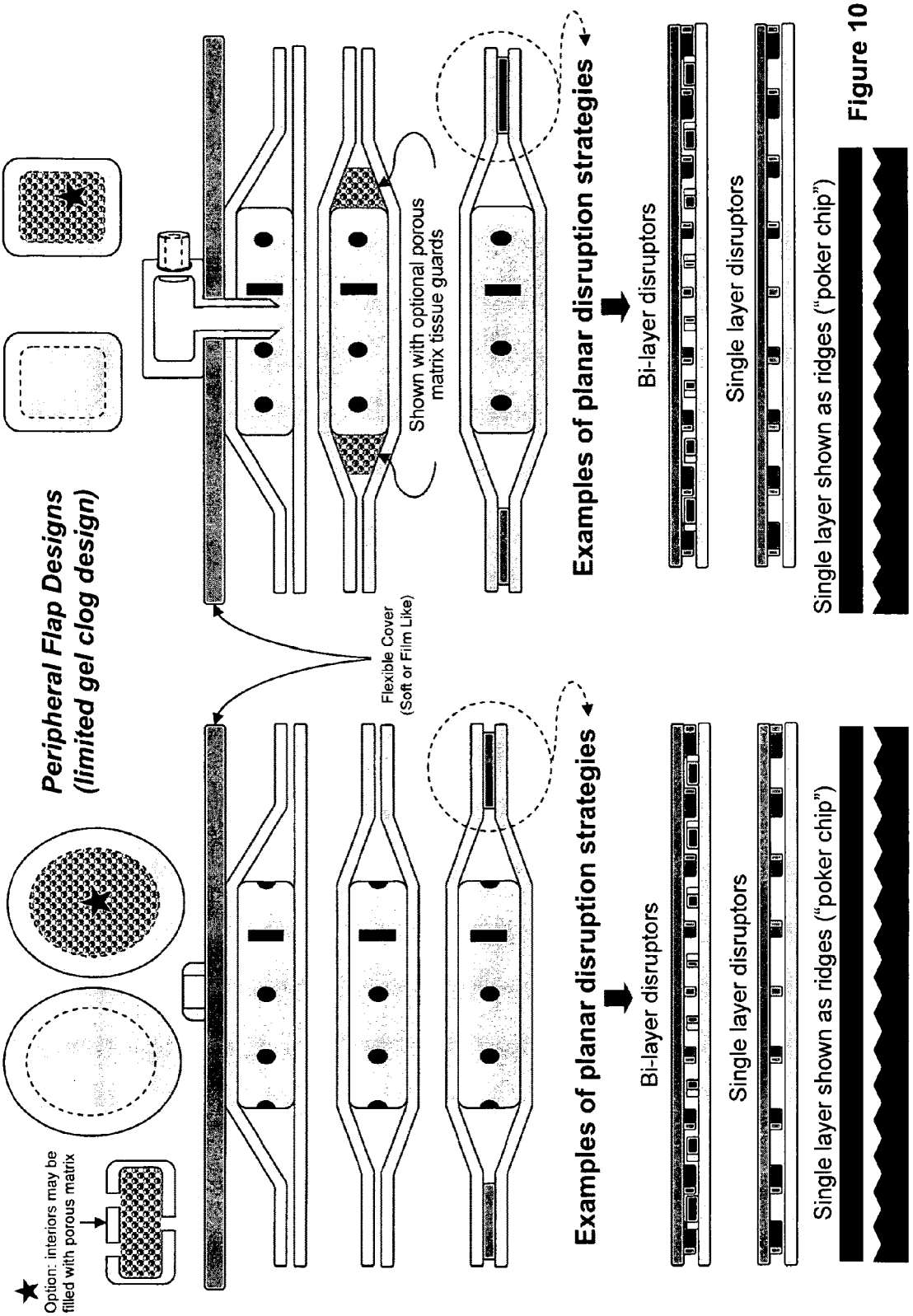
FIG. 10 shows a cross-sectional view of various peripheral flap designs which may be adapted for use with semisolids including gels. The drawings further show design options including a porous matrix interior, matrix tissue guards and planar disruptions.
Figure 11:
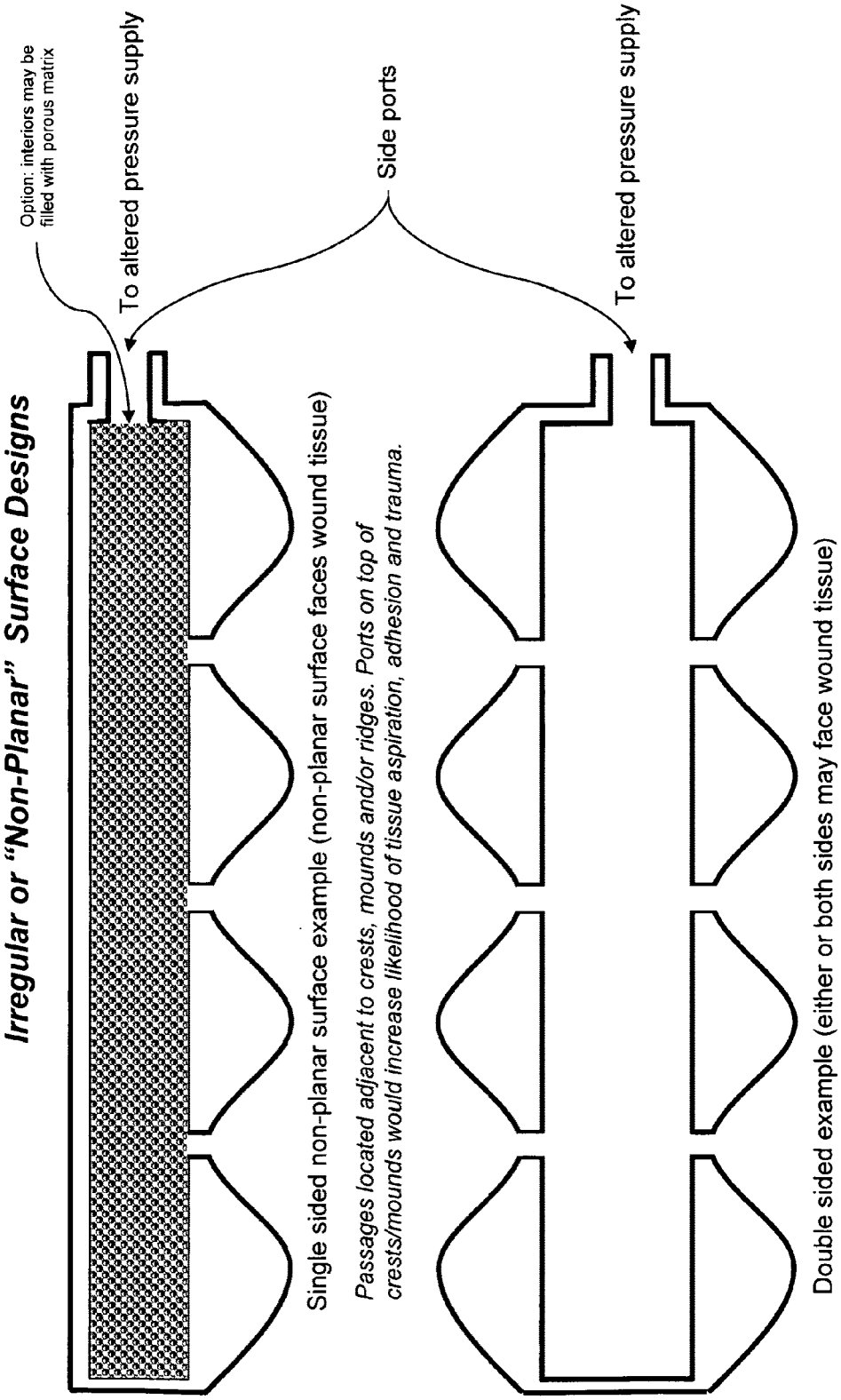

Referring to FIGS. 4 and 31-32, preferred embodiments are disclosed. Broadly a pressure monitoring/feedback means is provided inside or outside of the Encapsulated Space thereby providing input for a controlling means to regulate the pressure drive provided by the pressure source within a specified value and tolerance.

A best mode of the invention provides a means to monitor/sense the pressure within 10 cm from an opening in the cover utilizing a connection of two, independent Lumen.

A second best mode of the invention provides a means to monitor/sense the pressure greater than 10 cm from an opening in the cover.

A third best mode of the invention employs a pressure feedback/monitoring/sensing means located at the Proximal or Medial section of the PAM; where the pressure value detected is transferred by a transmitter of electromagnetic radiation, including radio waves, to a receiver communicating with a controlling means.

A fourth best mode of the invention employs a partially capsulated union, located outside of the Encapsulated Space, and adapted to provide a pressure feedback/monitoring/sensing space to the PAM by connecting a multiple passage means, including a dual Lumen design, a two side by side tube design or a coaxial conduit design, to the partially capsulated union.

One method of the invention may be operated by providing a pressure feedback/monitoring/sensing means in the form of a multiple passage means, including a dual Lumen design, a two side by side tube design or a coaxial conduit design, to the terminal PAM, Encapsulated Space, Encapsulated Sub-Space or a partially capsulated union located at the Proximal or Medial section of the PAM. Another method further comprises transferring the pressure detected by a transmitter of electromagnetic radiation, including radio waves, to a receiver communicating with a controlling means.

The embodiments are further described by the following aspects:

1. An Altered Pressure Apparatus where the PAM is comprised of a means for monitoring the pressure inside or outside of the Encapsulated Space within 10 cm from any opening in the cover thereby providing input for a controlling means to regulate the pressure drive provided by the pressure source within a specified value and tolerance.
2. The PAM of item 1 at least partially further comprised of one tube, or one conduit, composed of dual Lumen (two independent Lumen) where: (a) one Lumen delivers the Altered Pressure directly or indirectly from the pressure source to the Proximal end, and (b) the other Lumen provides feedback from the Proximal end to the controlling means.
3. The PAM of item 1 at least partially further comprised two side by side tubes, or conduits, each containing an independent Lumen (aka one Lumen per tube/conduit), at least partially attached by one or several lateral connections where: (a) one Lumen delivers the Altered Pressure directly or indirectly from the pressure source to the Proximal end, and (b) the other Lumen provides feedback from the Proximal end to the controlling means.
4. The PAM of item 3 where the connection is continuous for the length of the tubes or conduits.
5. The PAM of item 3 where the connection is intermittent for the length of the tubes or conduits.
6. The PAM of item 3 where the connection is intermittent and removable.
7. The PAM of item 1 at least partially further comprised of a coaxial conduit where (a) the inner most Lumen of the coax delivers the Altered Pressure directly or indirectly from the pressure source to the Proximal end, and (b) the outer most Lumen of the coax provides feedback from the Proximal end to the controlling means.
8. The PAM of items 1-7 further comprising a pressure sensing means located at the Proximal or Medial section of the PAM; where the pressure value detected is transferred by a transmitter of electromagnetic radiation, including radio waves, to a receiver communicating with a controlling means; thereby providing input for a controlling means to regulate the pressure drive provided by the pressure source within a specified value and tolerance.
9. An Altered Pressure Apparatus where the PAM is comprised of a means for monitoring the pressure located outside of the Encapsulated Space and >10 cm from any opening in the cover thereby providing input for a controlling means to regulate the pressure drive provided by the pressure source within a specified value and tolerance.
10. The PAM of item 9 at least partially further comprised of one tube, or one conduit, composed of dual Lumen (two independent Lumen) where: (a) one Lumen delivers the Altered Pressure directly or indirectly from the pressure source to the Proximal end, and (b) the other Lumen provides feedback from the Proximal end to the controlling means.
11. The PAM of item 9 at least partially further comprised two side by side tubes, or conduits, each containing an independent Lumen (aka one Lumen per tube/conduit), at least partially attached by one or several lateral connections where: (a) one Lumen delivers the Altered Pressure directly or indirectly from the pressure source to the Proximal end, and (b) the other Lumen provides feedback from the Proximal end to the controlling means.
12. The PAM of item 11 where the connection is continuous for the length of the tubes or conduits.
13. The PAM of item 11 where the connection is intermittent for the length of the tubes or conduits.
14. The PAM of item 11 where the connection is intermittent and removable.
15. The PAM of item 9 at least partially further comprised of a coaxial conduit where (a) the inner most Lumen of the coax delivers the Altered Pressure directly or indirectly from the pressure source to the Proximal end, and (b) the outer most Lumen of the coax provides feedback from the Proximal end to the controlling means.
16. The PAM of items 9-15 further comprising a pressure sensing means located at the Proximal or Medial section of the PAM; where the pressure value detected is transferred by a transmitter of electromagnetic radiation, including radio waves, to a receiver communicating with a controlling means; thereby providing input for a controlling means to regulate the pressure drive provided by the pressure source within a specified value and tolerance.
17. The PAM of items 1-16 wherein the means for monitoring the pressure includes a partially capsulated union, located outside of the Encapsulated Space, and adapted to provide a pressure feedback sensing space to the PAM by connecting a multiple passage means, including a dual Lumen design, a two side by side tube design or a coaxial conduit design, to the partially capsulated union.
18. The PAM of item 17 wherein the terminating section of the PAM, which communicates the Encapsulated Space to the partially capsulated union, is constructed of a passage, tubing or conduit with only one connecting opening to the Encapsulated Space.
19. The PAM of item 17 wherein the capsulated union is also a bulk collection means.
20. The PAM of item 17 wherein the capsulated union is independent of the bulk collection means.
21. The PAM of items 2-3 and 10-11 where the side by side or dual Lumen conduit that is significantly flattened to improve flexibility and patient comfort.

XIX. Security & Transport Configurations for Altered Pressure Therapy System

Referring to FIGS. 38-41, broadly a preferred system is disclosed to make Altered Pressure wound therapy devices and components readily transportable in an organized and secure manner. The best mode of the invention involves the utility of a Cradle configuration, as defined herein, that can be readily separated from the pressure source and collection means of the systems i.e. the Cradle is not intended to be fixed to these devices. This Cradle provides for the organization of the pressure source and collection means, including ancillary components, but the primary function of the Cradle is to secure the pressure source and collection means to prevent them from upset. The smaller and more Mobile the pressure source design, the more important securing it becomes. Therefore, the Cradle allows a Mobile pressure source to be transported and utilized with the collection means without fear of constant upset. To that end, the Cradle provides the means to satisfy the needs of both the Portable and Mobile market segments with one pump. It also provides a means to send the patient home from the hospital (Portable) market with the same pressure source for the home care (Mobile) market, which reduces the risk of noncompliance and misuse by giving the patient equipment he has previously been introduced to.

A second mode provides a means to at least partially hide the wound exudate from public view. While securing the collection means is the principle function, utilizing the bays to at least partially hide the wound exudate provides a valuable function beyond elegance, as some laymen faint at the sight of bodily fluids, risking injury.

One method of the invention may be operated by providing inserts for the Cradle bays to accommodate various pump and canister dimensions. Another method is to employ a floor compartment for battery backup, or simply ballast, if appropriate to add further stability to the system, thereby further preventing upset and spillage.

Figure 41:
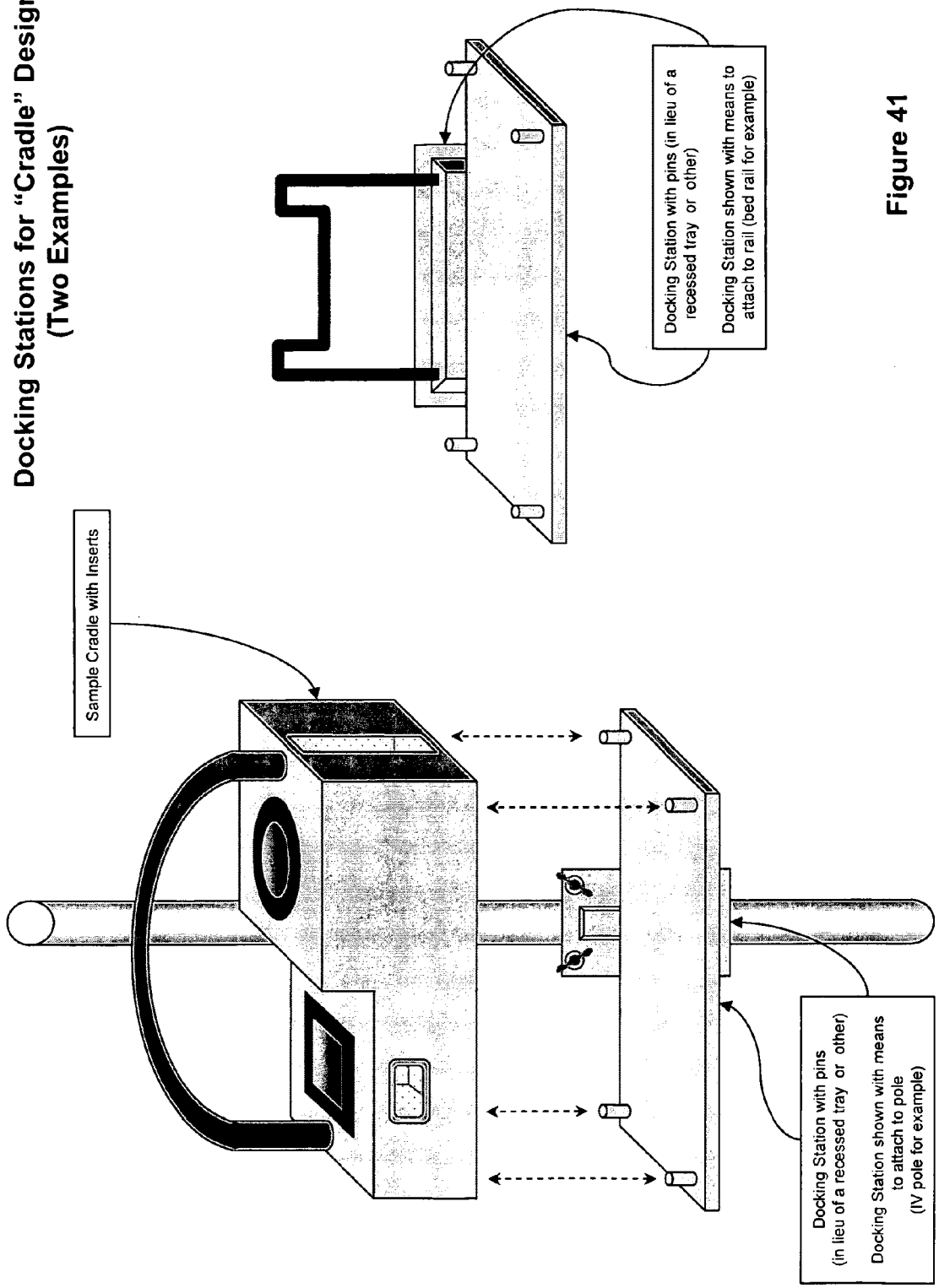
FIG. 41 shows various docking station configurations for an Altered Pressure wound therapy system composed of a pressure source, collection means and a Cradle.

Referring to FIG. 41, broadly a preferred system is disclosed to provide a docking base removably fixable to a stable object including a bed, a stand, a pole, a piece of furniture or a wall. The base is intended to merge with a Cradle configured system, rendering even greater stability to the same, while keeping the system out of the direct work area of the clinicians. The best mode of the invention involves the utility of a clamp for any post and a hooking or overlay means for any rail or bed board. Brackets may be used for wall mounts.

The embodiments are further described by the following aspects:

1. A system for Altered Pressure wound therapy comprising: (a) an Altered Pressure source to provide the Altered Pressure; (b) a collection means to hold wound drainage; and (c) a Portable Cradle which (i) can be readily separated as a stand alone component physically independent of (a) and (b), (ii) is adapted for the organization of (a) and (b), and (iii) is adapted to secure (a) and (b) by inhibiting the unrestricted movement of (a) or (b) in at least one direction; thereby preventing the unintentional upset, damage or loss of either (a) or (b), and optionally, providing a means to manufacture one pressure source to service both Mobile and Portable markets.
2. The system of item 1 where the Cradle is further adapted to at least partially hide the wound exudate collecting in the collection means from the public view, thereby preventing the nausea commonly felt by patients and laymen not accustomed to the sight of such bodily fluids.
3. The system of item 1 where the Cradle is further adapted to render the system collectively Portable even if the pressure source is independently Mobile.
4. The system of item 1 where the Cradle is further adapted to merge with a docking station removably fixable to a stable object including a bed, a stand, a pole, a piece of furniture or a wall, providing a secure base to rest the Cradle while conserving work space.
5. The system of item 1 where the Cradle is further composed of Bay inserts adapted to accommodate multiple pressure source sizes and collection means sizes.
6. The system of item 1 where the Cradle is comprised of bays in addition to the pressure source and collection means bays, thereby accommodating other devices such as excess tubing, spare dressings, spare batteries or other items.
7. The system of item 1 where the Cradle is further composed a floor compartment to house a battery power source or stabilizing ballast.
8. A docking station for the Cradle of items 1-7: (a) adapted to merge with the Cradle, (b) removably fixable to a stable object including a bed, a stand, a pole, a piece of furniture or a wall, and (c) providing a secure base to rest the Cradle while conserving work space.

Figure 42:
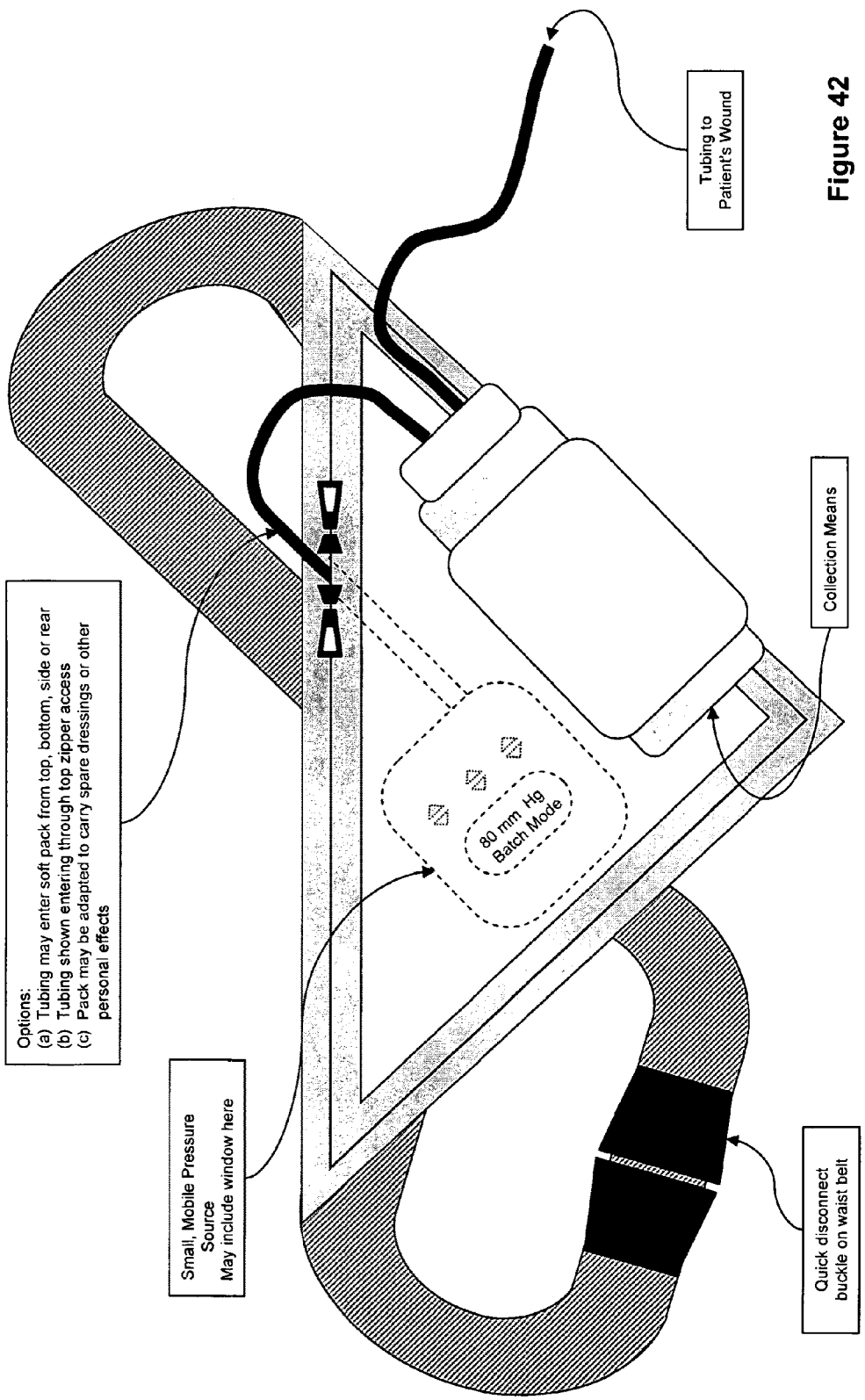
FIGS. 42-43 illustrate Mobile transport accessory configurations for hands-free waist transport of an Altered Pressure wound therapy system intended to aid transport, secure the system including biological fluids and allow the use of both hands during ambulation by patients.
Figure 43:
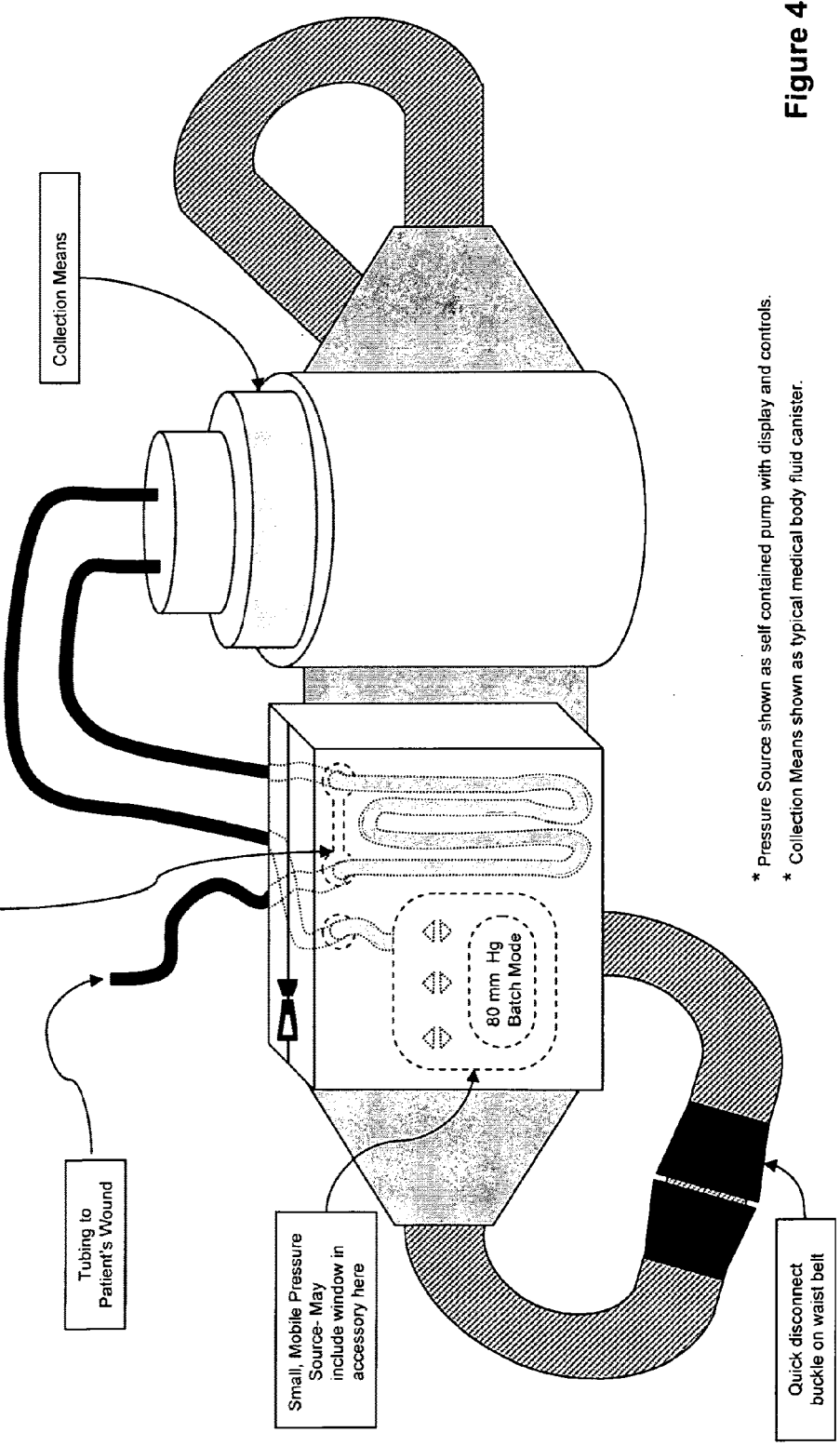

Referring to FIGS. 42-43, broadly a preferred system is disclosed to make Altered Pressure wound therapy devices and components readily transportable in an organized, Mobile and secure manner. The best mode of the invention involves the utility of a Mobile accessory configuration, as defined herein, that can be readily separated from the pressure source and collection means of the systems i.e. the accessory is not intended to be fixed to these devices. This accessory provides for the organization of the pressure source and collection means, including ancillary components, but the primary function of the accessory is to allow the pressure source and collection means to be transported by the patient without the use of his hands. The accessory allows a Mobile pressure source to be transported and utilized with the collection means with two free hands to aid balance and ambulation. Two free hands is a great advantage for many patients suffering from chronic wounds. Other than comfort and convenience, many of these patients require aids and prosthetics to be able to walk independently, most of which are greatly augmented by the use of both hands.

A second mode provides a means to at least partially hide the wound exudate from public view. While securing the collection means is the principle function, utilizing the pockets to at least partially hide the wound exudate provides a valuable function beyond elegance as previously outlined.

One method of the invention may be operated by securing the accessory around the patient's waist via a quick disconnect belt buckle. Another method is to employ an accessory adapted to merge with a docking station removably fixable to a stable object in the patient's residence, thereby providing a convenient means to store the system readily retrievable for ambulation and transport.

The embodiments are further described by the following aspects:

9. A system for Altered Pressure wound therapy comprising: (a) an Altered Pressure source to provide the Altered Pressure; (b) a collection means to hold wound drainage; and (c) a Mobile transport accessory which: (i) can be readily separated as a stand alone component physically independent of (a) and (b), (ii) is adapted for the organization of (a) and (b), (iii) is adapted to secure (a) and (b) by inhibiting the unrestricted movement of (a) or (b) in at least one direction and (iv) is adapted to be removably fixable around the patient's waist and worn hands-free; thereby providing the patient full use of both hands providing increased safety while preventing the unintentional upset, damage or loss of either (a) or (b).
10. The system of item 9 where the accessory is further adapted to at least partially hide the wound exudate collecting in the collection means from the public view, thereby preventing the nausea commonly felt by patients and laymen not accustomed to the sight of such fluids.
11. The system of item 9 where the accessory is further adapted to render the system collectively Mobile.
12. The system of item 9 where the accessory is further adapted to merge with a docking station removably fixable to a stable object including a bed, a stand, a pole, a piece of furniture or a wall, providing a secure base to rest the accessory when patient is not ambulatory.

13. The system of item 9 where the accessory is comprised of pockets or bays in addition to those of the pressure source and collection means, thereby accommodating other devices such as excess tubing, spare dressings, spare batteries or other items.
14. A docking station for the accessory of items 9-13: (a) adapted to merge with the accessory, (b) removably fixable to a stable object including a bed, a stand, a pole, a piece of furniture or a wall, and (c) providing a secure base to rest the accessory while patient is non-ambulatory.

XX. Ancillary Aspects

Broadly ancillary aspects and embodiments are disclosed which improve the performance of Altered Pressure wound therapy, make the treatments more comfortable for the patient and the delivery of the treatment more convenient for clinicians.

Many variations of the invention will occur to those skilled in the art. Some variations include:

The embodiments described by the following aspects:
1. The PAM disclosed herein, adapted for introducing liquid medication into the Encapsulated Space through the PAM Proximal end.
2. The wound covering disclosed herein whose permeability is limited enough to allow the system to maintain the desired pressure within the Encapsulated Space.
3. The wound covering of item 2 selected from a group of materials classified as impermeable, semi-permeable, permeable, non-occlusive, occlusive, partially occlusive or combinations thereof.
4. The Encapsulated Space disclosed herein accessed by a PAM via methods selected from the group of: under covering perimeter edge and sealing means, between covering perimeter, through covering and any combination thereof.
5. The PAM disclosed herein further comprising a non-planar interior to limit blockage due to the collapse of the PAM when exposed to negative pressures.
6. A method of inhibiting the collapse and partial blockage of a PAM utilized in an Altered Pressure Apparatus comprising: providing a non-planar interior to inhibit total collapse when exposed to negative pressures or external pressures including untended impingements or patient weight.
7. The Sealing means disclosed herein selected from the group of an adhesive, a vacuum seal, a sealant to assist a vacuum seal, a continuous tape seal over covering peripheral edge, a discontinuous tape seal adapted to prevent covering dislocation, ties adapted to prevent covering dislocation, straps adapted to prevent covering dislocating and any combination thereof.
8. The apparatus disclosed herein where the components of the dressing, PAM or the bulk collection means including containers, closures, liners, spill catches and shrouds, Intermediate Materials, Secondary Materials, covering means, sealing means, cushioning means and any combination thereof are sold in Kits.
9. An Altered Pressure dressing kit containing any semisolid of this application.
10. An Altered Pressure dressing kit containing any foam Rope or Raft.
11. An Altered Pressure dressing kit containing a semisolid and foam dressing.
12. The PAM disclosed herein consisting of a splitting means between the Medial section and Proximal end, adapted to add additional Medial and Proximal sections for the treatment of more than one wound.
13. The apparatus disclosed herein comprising a Primary Material inserted or otherwise located, between the wound tissue and Intermediate Material in contact with the terminating PAM.
14. The apparatus disclosed herein comprising a Secondary Material contacting portions of the wound tissue and at least a portion of an Intermediate Material located in between the terminating PAM and wound tissue.
15. The Altered Pressure Apparatus disclosed herein where the Altered Pressure source is comprised of a means to program regimens or batches for automated control of treatment cycles.
16. The PAM disclosed herein having a means of disconnection and replacement of the Proximal section and optionally Medial section of the PAM.
17. The Altered Pressure Apparatus disclosed herein further comprising injection or infusion port with a sealing means for the delivery of liquids to the Encapsulated Space, located upon the covering or PAM.
18. The Altered Pressure Apparatus of item 17 where the sealing means is a self sealing injection membrane or a valve.
19. The Altered Pressure Apparatus of item 17 where the liquid is driven by a peristaltic or piston pump.
20. The Altered Pressure Apparatus disclosed herein further comprising a one-way valve relief port, located upon the covering or PAM, thereby preventing the pressures in the Encapsulated Space from reaching an undesired value.
21. The Altered Pressure Apparatus of item 20 where the relief port is connected to tubing for direct the discharge of excess fluids.
22. A method of controlling peak pressures and providing a means for the removal of excess irrigation intended for use with an Altered Pressure Apparatus for wound therapy comprising: installing a one-way valve relief port, locating said port on covering means or with the PAM, and further connecting a conduit to said relief port to direct expelled liquids and gases away from patient.
23. An Altered Pressure Apparatus where the PAM is comprised of at least one means to control flow in one direction.
24. The Altered Pressure Apparatus of item 23 where the means to control flow direction is located in the PAM.
25. The Altered Pressure Apparatus of item 23 where the means to control flow direction is a one-way valve.
26. Any foam disclosed herein including proteinaceous foams, closed-cell foams, opened-cell foams, foams made at least partially non-porous by a sealing means where the foam is perforated or fenestrated purposefully to promote the transfer of bodily fluids through the said perforations or fenestrations when under negative pressure.
27. The foam of item 26 when used with a semisolid.
28. A method of at least partially selective transfer of substances through a foam Intermediate used with Altered Pressure therapy comprising: providing and utilizing perforations or fenestrations in the foam when used with a semisolid, thereby providing a least partially selective transfer of bodily fluids through the perforations or fenestrations while retaining most of the semisolid at the tissue/dressing interface.

All such variations are intended to be within the scope and spirit of the invention.

Although some embodiments are shown to include certain features, the applicant(s) specifically contemplate that any feature disclosed herein may be used together or in combination with any other feature on any embodiment of the invention. It is also contemplated that any feature may be specifically excluded from any embodiment of an invention.

Example 1

| | |
|---|---|
| Purified Water, USP | 7% |
| Glyceryl monooleate | 93% |

Purified water, USP was heated to approximately 40° C. Glyceryl Monooleate (GMO) was heated to melting. The purified water was combined with GMO. The resulting system was well mixed and allowed to return to ambient temperature undisturbed. The resulting mixture produced a hazy gel formulation with a relatively low viscosity.

Example 2

| | |
|---|---|
| Ethanol, USP | 3% |
| Purified Water, USP | 4% |
| Glyceryl monooleate | 93% |

Purified Water, USP was combined with Ethanol, USP and heated to approximately 40° C. Glyceryl Monooleate (GMO) was heated to melting. The solvents were combined with GMO. The resulting system was well mixed and allowed to return to ambient temperature undisturbed. The resulting mixture produced a hazy liquid-gel formulation with a relatively low viscosity.

Example 3

| | |
|---|---|
| Ethanol, USP | 3% |
| Purified Water, USP | 4% |
| Capric Acid | 0.5% |
| Lauric Acid | 0.5% |
| Glyceryl monooleate | 92% |

Purified Water, USP was combined with Ethanol, USP and heated to approximately 40° C. Glyceryl Monooleate (GMO) was heated to melting and the Capric Acid and Lauric Acid were dissolved therein. The solvents were combined with GMO-fatty acid mixture. The resulting system was well mixed and allowed to return to ambient temperature undisturbed. The resulting mixture produced a hazy liquid-gel formulation with a relatively low viscosity.

Example 4A

| | |
|---|---|
| Ethanol, USP | 4.7% |
| Purified Water, USP | 2.3% |
| Capric Acid | 3% |
| Lauric Acid | 3% |
| Glyceryl monooleate | 87% |

Example 4B

| | |
|---|---|
| Ethanol, USP | 4.7% |
| Purified Water, USP | 2.3% |
| Capric Acid | 1.5% |
| Lauric Acid | 1.5% |
| Monoerucin | 90% |

In both examples the Purified Water, USP was combined with Ethanol, USP and heated to approximately 40° C. Glyceryl Monooleate (GMO) or Monoerucin (GME) was heated to melting and the Capric Acid and Lauric Acid were dissolved therein. The solvents were combined with GMO or GME fatty acid mixture. The resulting system was well mixed and allowed to return to ambient temperature undisturbed. The resulting mixture produced a hazy liquid-gel formulation with a relatively low viscosity.

Example 5

| | |
|---|---|
| Propylene Glycol, USP | 5% |
| Glyceryl monooleate | 95% |

Propylene Glycol, USP, was heated to approximately 40° C. Glyceryl Monooleate (GMO) was heated to melting. The propylene glycol was combined with GMO. The resulting system was well mixed and allowed to return to ambient temperature undisturbed. The resulting mixture produced a clear liquid-gel formulation with a relatively low viscosity.

Example 6

| | |
|---|---|
| Polyethylene Glycol 300 | 20% |
| Ethanol, USP | 5% |
| Glyceryl monooleate | 75% |

PEG 300 was mixed with the Ethanol USP and heated to approximately 40° C. Glyceryl Monooleate (GMO) was heated to melting. The PEG-Ethanol was combined with GMO. The resulting system was well mixed and allowed to return to ambient temperature undisturbed. The resulting mixture produced a clear liquid-gel formulation with a relatively low viscosity.

Example 7A

| | |
|---|---|
| Lactoferrin | 1% |
| Purified Water, USP | 7% |
| Glyceryl monooleate | 92% |

Purified water, USP was heated to approximately 40° C. Glyceryl Monooleate (GMO) was heated to melting. Lactoferrin powder is added to GMO and well dispersed. The purified water was combined with GMO. The resulting system was well mixed and allowed to return to ambient temperature undisturbed. The resulting mixture produced a hazy gel formulation with a relatively low viscosity. Alternatively, lactoferrin may be dissolved in Water, USP prior to addition to GMO.

Example 7B

| | |
|---|---|
| Lactoferrin | 5% |
| Purified Water, USP | 7% |
| Glyceryl monooleate | 88% |

Purified water, USP was heated to approximately 40° C. Glyceryl Monooleate (GMO) was heated to melting. Lactoferrin powder is added to GMO and well dispersed. The purified water was combined with GMO. The resulting system was well mixed and allowed to return to ambient temperature undisturbed. The resulting mixture produced a hazy gel formulation with a relatively low viscosity. Alternatively, lactoferrin may be dissolved in Water, USP prior to addition to GMO.

Example 7C

| | |
|---|---|
| Lactoferrin | 10% |
| Purified Water, USP | 7% |
| Glyceryl monooleate | 83% |

Purified water, USP was heated to approximately 40° C. Glyceryl Monooleate (GMO) was heated to melting. Lactoferrin powder is added to GMO and well dispersed. The purified water was combined with GMO. The resulting system was well mixed and allowed to return to ambient temperature undisturbed. The resulting mixture produced a hazy gel formulation with a relatively low viscosity. Alternatively, lactoferrin may be dissolved in Water, USP prior to addition to GMO.

Example 8

| | |
|---|---|
| Lactoferrin | 1% |
| Ethanol, USP | 3.5% |
| Purified Water, USP | 3.5% |
| Glyceryl monooleate | 92% |

Purified water, USP was added to Ethanol, USP and the mixture was heated to approximately 40° C. Glyceryl Monooleate (GMO) was heated to melting. Lactoferrin powder is added to GMO and well dispersed. The purified water was combined with GMO. The resulting system was well mixed and allowed to return to ambient temperature undisturbed. The resulting mixture produced a hazy gel formulation with a relatively low viscosity.

Example 9

| | |
|---|---|
| Vancomycin | 1% |
| Lactoferrin | 1% |
| Purified Water, USP | 7% |
| Glyceryl monooleate | 91% |

Purified water, USP was heated to approximately 40° C. Glyceryl Monooleate (GMO) was heated to melting. Lactoferrin and vancomycin powder is added to GMO and well dispersed. The purified water was combined with GMO. The resulting system was well mixed and allowed to return to ambient temperature undisturbed. The resulting mixture produced a hazy gel formulation with a relatively low viscosity. Alternatively, lactoferrin and vancomycin may be dissolved in Water, USP prior to addition to GMO.

Example 10

| | |
|---|---|
| Ethanol, USP | 3% |
| Purified Water, USP | 4% |
| Capric Acid | 1% |
| Lauric Acid | 1% |
| Lactoferrin | 1% |
| Glyceryl monooleate | 90% |

Purified water, USP was heated to approximately 40° C. Glyceryl Monooleate (GMO) was heated to melting. The ethanol was added and dispersed in the GMO. Capric and Lauric acid were added to the molten GMO and allowed to dissolve. Lactoferrin powder is added to GMO mixture and well dispersed. The purified water was combined with GMO mixture. The resulting system was well mixed and allowed to return to ambient temperature undisturbed. The resulting mixture produced a hazy gel formulation with a relatively low viscosity. Alternatively, lactoferrin may be dissolved in Water, USP prior to addition to GMO.

Example 11

| | |
|---|---|
| Ethanol, USP | 3% |
| Purified Water, USP | 4% |
| Capric Acid | 0.5% |
| Lauric Acid | 0.5% |
| Witch Hazel Extract | 1% |
| Glyceryl monooleate | 91% |

Purified water, USP was heated to approximately 40° C. Glyceryl Monooleate (GMO) was heated to melting. The ethanol was added and dispersed in the GMO. Capric and Lauric acid were added to the molten GMO and allowed to dissolve. Witch Hazel Extract is added to GMO mixture and well dispersed. The purified water was combined with GMO mixture. The resulting system was well mixed and allowed to return to ambient temperature undisturbed. The resulting mixture produced a hazy gel formulation with a relatively low viscosity.

Example 12

| | |
|---|---|
| Ethanol, USP | 3% |
| Purified Water, USP | 4% |
| Capric Acid | 1% |
| Lauric Acid | 1% |
| Witch Hazel Extract | 1% |
| Glyceryl monooleate | 90% |

Purified water, USP was heated to approximately 40° C. Glyceryl Monooleate (GMO) was heated to melting. The ethanol was added and dispersed in the GMO. Capric and Lauric acid were added to the molten GMO and allowed to dissolve. Witch Hazel Extract is added to GMO mixture and well dispersed. The purified water was combined with GMO mixture. The resulting system was well mixed and allowed to return to ambient temperature undisturbed. The resulting mixture produced a hazy gel formulation with a relatively low viscosity.

Example 13

| Ethanol, USP | 3% |
| Purified Water, USP | 4% |
| Capric Acid | 1% |
| Lauric Acid | 1% |
| Xylitol | 3% |
| Glyceryl monooleate | 88% |

Purified water, USP was heated to approximately 40° C. Glyceryl Monooleate (GMO) was heated to melting. The ethanol was added and dispersed in the GMO. Capric and Lauric acid were added to the molten GMO and allowed to dissolve. Xylitol is added to GMO mixture and well dispersed. The purified water was combined with GMO mixture. The resulting system was well mixed and allowed to return to ambient temperature undisturbed. The resulting mixture produced a hazy gel formulation with a relatively low viscosity.

Example 14

| Ethanol, USP | 3.5% |
| Purified Water, USP | 3.5% |
| Doxycycline Hyclate, USP | 1% |
| Glyceryl monooleate | 92% |

Purified water, USP was heated to approximately 40° C. Glyceryl Monooleate (GMO) was heated to melting. The ethanol was added and dispersed in the GMO. Doxycycline powder is added to GMO mixture and well dispersed. The purified water was combined with GMO mixture. The resulting system was well mixed and allowed to return to ambient temperature undisturbed. The resulting mixture produced a hazy gel formulation with a relatively low viscosity. Alternatively, the doxycycline may be dissolved in Water, USP prior to incorporation into the GMO mixture.

Example 15

| Ethanol, USP | 3.5% |
| Purified Water, USP | 3.5% |
| Cefazolin, USP | 1% |
| Glyceryl monooleate | 92% |

Purified water, USP was heated to approximately 40° C. Glyceryl Monooleate (GMO) was heated to melting. The ethanol was added and dispersed in the GMO. Cefazolin Sodium, USP powder is added to GMO mixture and well dispersed. The purified water was combined with GMO mixture. The resulting system was well mixed and allowed to return to ambient temperature undisturbed. The resulting mixture produced a hazy gel formulation with a relatively low viscosity. Alternatively, the cefazolin may be dissolved in Water, USP prior to incorporation into the GMO mixture.

Example 16

| Ethanol, USP | 3.5% |
| Purified Water, USP | 3.5% |
| Triclosan | 1% |
| Glyceryl monooleate | 92% |

Purified water, USP was heated to approximately 40° C. Glyceryl Monooleate (GMO) was heated to melting. The ethanol was added and dispersed in the GMO. Triclosan crystals are added to GMO mixture and well dispersed. The purified water was combined with GMO mixture. The resulting system was well mixed and allowed to return to ambient temperature undisturbed. The resulting mixture produced a hazy gel formulation with a relatively low viscosity.

Example 17

| Ethanol, USP | 3.5% |
| Purified Water, USP | 3.5% |
| Colloidal Silver powder | 1% |
| Glyceryl monooleate | 92% |

Purified water, USP was heated to approximately 40° C. Glyceryl Monooleate (GMO) was heated to melting. The ethanol was added and dispersed in the GMO. Silver powder is added to GMO mixture and well dispersed. The purified water was combined with GMO mixture. The resulting system was well mixed and allowed to return to ambient temperature undisturbed. The resulting mixture produced a hazy gel formulation with a relatively low viscosity.

Example 18

| Ethanol, USP | 3.5% |
| Purified Water, USP | 3.5% |
| Gallium nitrate | 1% |
| Glyceryl monooleate | 92% |

Purified water, USP was heated to approximately 40° C. Glyceryl Monooleate (GMO) was heated to melting. The ethanol was added and dispersed in the GMO. Gallium nitrate is added to GMO mixture and well dispersed. The purified water was combined with GMO mixture. The resulting system was well mixed and allowed to return to ambient temperature undisturbed. The resulting mixture produced a hazy gel formulation with a relatively low viscosity.

Example 19

| Ethanol, USP | 17% |
| Glyceryl monooleate | 83% |

Glyceryl Monooleate (GMO) was added to Ethanol, USP. The mixture was allowed to dissolve at room temperature with intermittent agitation. The resulting mixture was a clear viscous liquid.

Example 20

| | |
|---|---|
| 0.05 M PBS (pH 7.4) | 7% |
| Bacterial phage 2 ml extract powder | 0.2 g (6 × $10^{10}$ PFU/ml) |
| Glyceryl monooleate | 93% |

Glyceryl Monooleate (GMO) was heated to melting. The Bacteriophage powder extract was dispersed in the molten GMO with gentle agitation. The PBS was combined with GMO mixture. The resulting system was well mixed and allowed to return to ambient temperature undisturbed. The resulting mixture produced a hazy gel formulation with a relatively low viscosity.

Example 21

| | |
|---|---|
| Polyethylene Glycol (PEG) 300, NF | 90% |
| Glyceryl monooleate | 10% |

Glyceryl Monooleate (GMO) was heated to melting. The PEG was combined with GMO mixture. The resulting system was well mixed and allowed to return to ambient temperature undisturbed. The resulting mixture produced a clear liquid formulation with a relatively low viscosity.

Example 22

| | |
|---|---|
| Polyethylene Glycol (PEG) 300, NF | 50% |
| Ethanol, USP | 20% |
| Glyceryl monooleate | 30% |

Glyceryl Monooleate (GMO) was heated to melting. The PEG was combined with the Ethanol, USP with mixing. The PEG/ethanol mixture was combined with GMO. The resulting system was well mixed and allowed to return to ambient temperature undisturbed. The resulting mixture produced a clear liquid formulation with a relatively low viscosity.

Example 23

| | |
|---|---|
| Polyethylene Glycol (PEG) 400, NF | 10% |
| Polyethylene Glycol (PEG 200, NF | 5% |
| Glyceryl monooleate | 85% |

PEG 400, NF and PEG 200, NF were mixed and heated to approximately 40° C. Glyceryl Monooleate (GMO) was heated to melting. The PEG mixture was combined with GMO. The resulting system was well mixed and allowed to return to ambient temperature undisturbed. The resulting mixture produced a clear liquid formulation with a viscosity in the approximate range of 80-200 centipoise. In the present embodiment, other MW PEGs may be useful as well and interchanged with those described above to produce alternative formulations having similar pRoperties making such formulations operable wound applications.

The present examples 1-23 possess characteristics making them operable as a Hemostatic, fluid-controlling, and/or wound healing formulations for delivery in combination with Altered Pressure therapy. The formulations may be applied to any acute or chronic wound directly prior to application of the Altered Pressure dressings, or impregnated into Intermediate Materials such as gauze, foams or fibrotic packings. These examples were evaluated by the inventors with open cell foams, closed cell foams, proteinaceous foam and gauze in various configurations as described herein. The formulations are biodegradable and particularly adapted to filling even small void spaces, directing fluid flow, providing a cushioning effect, delivering active agents for durations exceeding dressing change schedules, preventing tissue in growth into foreign materials and providing an anti-adherence function to the dressings. The examples containing antimicrobials or biofilm agents are provided as non-limiting examples of the inventions ability to provide sustained release of actives which augment wound healing.

We claim:

1. An altered pressure device for treating a wound, the device comprising:
a cover sized to fit over the wound and including an opening therein, the cover defining an encapsulated space surrounding the wound;
an intermediate material layer positionable in the encapsulated space;
an altered pressure source communicating with the encapsulated space via a length of tubing coupled with the source, the tubing having a proximal end;
a proximal end piece connected to the proximal end of the tubing and including a flange at a lower portion thereof, wherein a bottom of the flange is comprised of a substantially planar surface adapted to be engageable with the periphery of the opening in the cover to create a seal, and wherein the proximal end piece is attachable to the cover adjacent the opening without extending through the cover; and
a hydrophobic semi-solid insertable within the encapsulated space.

2. A device according to claim 1, wherein the hydrophobic semi-solid is comprised of at least one lipid.

3. A device according to claim 2, wherein the at least one lipid is a liquid crystal forming compound.

4. A device according to claim 2, wherein the at least one lipid is a fatty acid ester.

5. A device according to claim 1, wherein the hydrophobic semi-solid provides an anti-infective activity, including biofilm inhibition.

6. An altered pressure device for treating a wound, the device comprising:
a cover sized to fit over the wound and including an opening therein, the cover defining an encapsulated space surrounding the wound;
an intermediate material layer positionable in the encapsulated space;
an altered pressure source communicating with the encapsulated space via a length of tubing coupled with the source, the tubing having a proximal end;
a proximal end piece connected to the proximal end of the tubing and including a flange at a lower portion thereof, wherein a bottom of the flange is comprised of a substantially planar surface adapted to be engageable with the periphery of the opening in the cover to create a seal, and wherein the proximal end piece is attachable to the cover adjacent the opening without extending through the cover; and
a support washer that provides a reinforced base for fixation of the planar surface at the bottom of the flange to the cover.

7. A device according to claim 6, wherein the washer further comprises an adhesive on at least the top or bottom surface.

8. An altered pressure device for treating a wound, the device comprising:
- a cover sized to fit over the wound and including an opening therein, the cover defining an encapsulated space surrounding the wound;
- an intermediate material layer positionable in the encapsulated space;
- an altered pressure source communicating with the encapsulated space via a length of tubing coupled with the source, the tubing having a proximal end; and
- a proximal end piece connected to the proximal end of the tubing and including a flange at a lower portion thereof, wherein a bottom of the flange is comprised of a substantially planar surface adapted to be engageable with the periphery of the opening in the cover to create a seal, and wherein the proximal end piece is attachable to the cover adjacent the opening without extending through the cover,
- wherein the tubing comprises a partially capsulated union of pressure altering and pressure sensing conduits, located between the altered pressure source and the end piece providing a pressure monitoring site.

9. An altered pressure device for treating a wound, the device comprising:
- a cover sized to fit over the wound and including an opening therein, the cover defining an encapsulated space surrounding the wound;
- an intermediate material layer positionable in the encapsulated space;
- an altered pressure source communicating with the encapsulated space via a length of tubing coupled with the source, the tubing having a proximal end;
- a proximal end piece connected to the proximal end of the tubing and including a flange at a lower portion thereof, wherein a bottom of the flange is comprised of a substantially planar surface adapted to be engageable with the periphery of the opening in the cover to create a seal, and wherein the proximal end piece is attachable to the cover adjacent the opening without extending through the cover; and
- means for controlling multiple altered pressure cycles in sequence, each pressure cycle composed of a specified target non-atmospheric value for a specified target duration.

10. A device according to claim 9, further comprising at least one negative pressure cycle greater than 0 mm Hg but less than 60 mm Hg relative to atmospheric.

11. An altered pressure device for treating a wound, the device comprising:
- a cover sized to fit over the wound and including an opening therein, the cover defining an encapsulated space surrounding the wound;
- an intermediate material layer positionable in the encapsulated space;
- an altered pressure source communicating with the encapsulated space via a length of tubing coupled with the source, the tubing having a proximal end; and
- a proximal end piece connected to the proximal end of the tubing and including a flange at a lower portion thereof, wherein a bottom of the flange is comprised of a substantially planar surface adapted to be engageable with the periphery of the opening in the cover to create a seal, and wherein the proximal end piece is attachable to the cover adjacent the opening without extending through the cover,
- wherein the tubing communicating the altered pressure source with the encapsulated space is flush with the flange.

12. A method of treating a wound, wherein a perimeter of the wound delimits a wound bed, the method comprising:
(a) applying an altered pressure apparatus to the wound bed; and
(b) providing an altered pressure to the wound bed in multiple altered pressure cycles in sequence prior to a dressing change, each pressure cycle composed of a specified target non-atmospheric value for a specified duration.

13. A method according to claim 12, wherein the pressure is monitored via a partially capsulated union of pressure altering and pressure sensing conduits, located between an exudate collection device and the wound bed.

14. A method according to claim 12, wherein the multiple altered pressure cycles include at least one negative pressure cycle greater than 0 mm Hg but less than 60 mm Hg, thereby maintaining the encapsulated space at a pressure negative to atmospheric to prevent exudate leakage and contamination.

15. A method according to claim 12, wherein step (a) is practiced by defining an encapsulated space surrounding the wound bed with a cover, and wherein step (b) is practiced by communicating an altered pressure source with the encapsulated space and securing a proximal end piece to the cover without extending through the cover.

* * * * *